(12) United States Patent
Narjes et al.

(10) Patent No.: US 11,866,518 B2
(45) Date of Patent: Jan. 9, 2024

(54) BICYCLIC PEPTIDE LIGANDS SPECIFIC FOR TSLP

(71) Applicant: BicycleTx Limited, Cambridge (GB)

(72) Inventors: Frank Narjes, Sodertalje (SE); Tor Svensson, Sodertalje (SE); Pavol Zlatoidsky, Sodertalje (SE); Lotta Hidestal, Sodertalje (SE); Liuhong Chen, Cambridge (GB); Michael Skynner, Cambridge (GB); Sophie Watcham, Cambridge (GB)

(73) Assignee: BicycleTx Limited, Cambridge (GB)

( * ) Notice: Subject to any disclaimer, the term of this patent is extended or adjusted under 35 U.S.C. 154(b) by 0 days.

(21) Appl. No.: 17/223,244

(22) Filed: Apr. 6, 2021

(65) Prior Publication Data

US 2022/0363718 A1   Nov. 17, 2022

Related U.S. Application Data

(60) Provisional application No. 63/005,744, filed on Apr. 6, 2020.

(51) Int. Cl.
| | |
|---|---|
| *C07K 7/64* | (2006.01) |
| *A61K 47/54* | (2017.01) |
| *A61K 38/00* | (2006.01) |

(52) U.S. Cl.
CPC .............. *C07K 7/64* (2013.01); *A61K 47/545* (2017.08); *A61K 38/00* (2013.01)

(58) Field of Classification Search
None
See application file for complete search history.

(56) References Cited

U.S. PATENT DOCUMENTS

2017/0066823 A1   3/2017   Edwards et al.

FOREIGN PATENT DOCUMENTS

| WO | WO 2014/167122 | * 10/2014 |
|---|---|---|
| WO | WO-2014167122 A1 | 10/2014 |
| WO | WO-2021205161 A1 | 10/2021 |

OTHER PUBLICATIONS

International Search Report and Written Opinion for PCT/GB2021/050846 dated Jul. 6, 2021 (11 pages).

* cited by examiner

*Primary Examiner* — Sergio Coffa
(74) *Attorney, Agent, or Firm* — Dechert LLP; Andrea L. C. Reid; Matthew C. Stevens

(57) ABSTRACT

The present invention relates to polypeptides which are covalently bound to molecular scaffolds such that two or more peptide loops are subtended between attachment points to the scaffold. In particular, the invention describes peptides which are high affinity binders of thymic stromal lymphopoietin (TSLP). The invention also includes pharmaceutical compositions comprising said peptide ligands and to the use of said peptide ligands in preventing, suppressing or treating a disease or disorder mediated by TSLP.

19 Claims, 5 Drawing Sheets

Specification includes a Sequence Listing.

SEQUENCE LISTING

<160> NUMBER OF SEQ ID NOS: 165

<210> SEQ ID NO 1
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (3)..(3)
<223> OTHER INFORMATION: Xaa is TrpMe
<220> FEATURE:
<221> NAME/KEY: Xaa
<222> LOCATION: (4)..(4)
<223> OTHER INFORMATION: Xaa is tBuA
<220> FEATURE:
<221> NAME/KEY: Xaa
<222> LOCATION: (8)..(8)
<223> OTHER INFORMATION: Xaa is TrpMe
<220> FEATURE:
<221> NAME/KEY: Xaa
<222> LOCATION: (9)..(9)
<223> OTHER INFORMATION: Xaa is ADMA
<220> FEATURE:
<221> NAME/KEY: Xaa
<222> LOCATION: (11)..(11)
<223> OTHER INFORMATION: Xaa is 4F3ClPhe

<400> SEQUENCE: 1

Cys Gln Xaa Xaa Gln Asp Cys Xaa Xaa Gly Xaa Cys
1               5                   10

<210> SEQ ID NO 2
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (3)..(3)
<223> OTHER INFORMATION: Xaa is TrpMe
<220> FEATURE:
<221> NAME/KEY: Xaa
<222> LOCATION: (4)..(4)
<223> OTHER INFORMATION: Xaa is tBuA
<220> FEATURE:
<221> NAME/KEY: Xaa
<222> LOCATION: (8)..(8)
<223> OTHER INFORMATION: Xaa is TrpMe
<220> FEATURE:
<221> NAME/KEY: Xaa
<222> LOCATION: (9)..(9)
<223> OTHER INFORMATION: Xaa is ADMA
<220> FEATURE:
<221> NAME/KEY: Xaa
<222> LOCATION: (11)..(11)
<223> OTHER INFORMATION: Xaa is 4-FPhe

<400> SEQUENCE: 2

Cys Gln Xaa Xaa Gln Asp Cys Xaa Xaa Gly Xaa Cys
1               5                   10

<210> SEQ ID NO 3
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (3)..(3)
<223> OTHER INFORMATION: Xaa is TrpMe

```
<220> FEATURE:
<221> NAME/KEY: Xaa
<222> LOCATION: (4)..(4)
<223> OTHER INFORMATION: Xaa is tBuA
<220> FEATURE:
<221> NAME/KEY: Xaa
<222> LOCATION: (8)..(8)
<223> OTHER INFORMATION: Xaa is TrpMe
<220> FEATURE:
<221> NAME/KEY: Xaa
<222> LOCATION: (9)..(9)
<223> OTHER INFORMATION: Xaa is ADMA
<220> FEATURE:
<221> NAME/KEY: Xaa
<222> LOCATION: (11)..(11)
<223> OTHER INFORMATION: Xaa is 4-FPhe

<400> SEQUENCE: 3

Cys Gln Xaa Xaa Glu Asp Cys Xaa Xaa Gly Xaa Cys
1               5                   10

<210> SEQ ID NO 4
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (4)..(4)
<223> OTHER INFORMATION: Xaa is tBuA
<220> FEATURE:
<221> NAME/KEY: Xaa
<222> LOCATION: (11)..(11)
<223> OTHER INFORMATION: Xaa is 4-FPhe

<400> SEQUENCE: 4

Cys Gln Trp Xaa Glu Asp Cys Trp Arg Gly Xaa Cys
1               5                   10

<210> SEQ ID NO 5
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is AMe
<220> FEATURE:
<221> NAME/KEY: Xaa
<222> LOCATION: (3)..(3)
<223> OTHER INFORMATION: Xaa is TrpMe
<220> FEATURE:
<221> NAME/KEY: Xaa
<222> LOCATION: (4)..(4)
<223> OTHER INFORMATION: Xaa is tBuA
<220> FEATURE:
<221> NAME/KEY: Xaa
<222> LOCATION: (6)..(6)
<223> OTHER INFORMATION: Xaa is MeD
<220> FEATURE:
<221> NAME/KEY: Xaa
<222> LOCATION: (8)..(8)
<223> OTHER INFORMATION: Xaa is TrpMe
<220> FEATURE:
<221> NAME/KEY: Xaa
<222> LOCATION: (9)..(9)
<223> OTHER INFORMATION: Xaa is ADMA
<220> FEATURE:
<221> NAME/KEY: Xaa
<222> LOCATION: (11)..(11)
<223> OTHER INFORMATION: Xaa is 4-FPhe
```

```
<400> SEQUENCE: 5

Cys Xaa Xaa Xaa Gln Xaa Cys Xaa Xaa Gly Xaa Cys
1               5                   10

<210> SEQ ID NO 6
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (11)..(11)
<223> OTHER INFORMATION: Xaa is 4F3ClPhe

<400> SEQUENCE: 6

Cys Gln Trp Leu Glu Asp Cys Trp Arg Gly Xaa Cys
1               5                   10

<210> SEQ ID NO 7
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is AMe
<220> FEATURE:
<221> NAME/KEY: Xaa
<222> LOCATION: (3)..(3)
<223> OTHER INFORMATION: Xaa is TrpMe
<220> FEATURE:
<221> NAME/KEY: Xaa
<222> LOCATION: (4)..(4)
<223> OTHER INFORMATION: Xaa is tBuA
<220> FEATURE:
<221> NAME/KEY: Xaa
<222> LOCATION: (8)..(8)
<223> OTHER INFORMATION: Xaa is TrpMe
<220> FEATURE:
<221> NAME/KEY: Xaa
<222> LOCATION: (9)..(9)
<223> OTHER INFORMATION: Xaa is LysMe3
<220> FEATURE:
<221> NAME/KEY: Xaa
<222> LOCATION: (11)..(11)
<223> OTHER INFORMATION: Xaa is 4-FPhe

<400> SEQUENCE: 7

Cys Xaa Xaa Xaa Gln Asp Cys Xaa Xaa Gly Xaa Cys
1               5                   10

<210> SEQ ID NO 8
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (11)..(11)
<223> OTHER INFORMATION: Xaa is 4-FPhe

<400> SEQUENCE: 8

Cys Gln Trp Leu Glu Asp Cys Trp Arg Gly Xaa Cys
1               5                   10

<210> SEQ ID NO 9
<211> LENGTH: 12
```

```
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (11)..(11)
<223> OTHER INFORMATION: Xaa is 3,4diClPhe

<400> SEQUENCE: 9

Cys Gln Trp Leu Glu Asp Cys Trp Arg Gly Xaa Cys
1               5                   10

<210> SEQ ID NO 10
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is AMe
<220> FEATURE:
<221> NAME/KEY: Xaa
<222> LOCATION: (3)..(3)
<223> OTHER INFORMATION: Xaa is TrpMe
<220> FEATURE:
<221> NAME/KEY: Xaa
<222> LOCATION: (4)..(4)
<223> OTHER INFORMATION: Xaa is tBuA
<220> FEATURE:
<221> NAME/KEY: Xaa
<222> LOCATION: (8)..(8)
<223> OTHER INFORMATION: Xaa is TrpMe
<220> FEATURE:
<221> NAME/KEY: Xaa
<222> LOCATION: (9)..(9)
<223> OTHER INFORMATION: Xaa is ChMeA
<220> FEATURE:
<221> NAME/KEY: Xaa
<222> LOCATION: (11)..(11)
<223> OTHER INFORMATION: Xaa is 4-FPhe

<400> SEQUENCE: 10

Cys Xaa Xaa Xaa Gln Asp Cys Xaa Xaa Gly Xaa Cys
1               5                   10

<210> SEQ ID NO 11
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (3)..(3)
<223> OTHER INFORMATION: Xaa is TrpMe
<220> FEATURE:
<221> NAME/KEY: Xaa
<222> LOCATION: (8)..(8)
<223> OTHER INFORMATION: Xaa is TrpMe
<220> FEATURE:
<221> NAME/KEY: Xaa
<222> LOCATION: (9)..(9)
<223> OTHER INFORMATION: Xaa is ADMA
<220> FEATURE:
<221> NAME/KEY: Xaa
<222> LOCATION: (11)..(11)
<223> OTHER INFORMATION: Xaa is 4-FPhe

<400> SEQUENCE: 11

Cys Gln Xaa Leu Glu Asp Cys Xaa Xaa Gly Xaa Cys
1               5                   10
```

```
<210> SEQ ID NO 12
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (11)..(11)
<223> OTHER INFORMATION: Xaa is 4-ClPhe

<400> SEQUENCE: 12

Cys Gln Trp Leu Glu Asp Cys Trp Arg Gly Xaa Cys
1               5                   10

<210> SEQ ID NO 13
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is AMe
<220> FEATURE:
<221> NAME/KEY: Xaa
<222> LOCATION: (3)..(3)
<223> OTHER INFORMATION: Xaa is TrpMe
<220> FEATURE:
<221> NAME/KEY: Xaa
<222> LOCATION: (4)..(4)
<223> OTHER INFORMATION: Xaa is tBuA
<220> FEATURE:
<221> NAME/KEY: Xaa
<222> LOCATION: (8)..(8)
<223> OTHER INFORMATION: Xaa is TrpMe
<220> FEATURE:
<221> NAME/KEY: Xaa
<222> LOCATION: (9)..(9)
<223> OTHER INFORMATION: Xaa is ADMA
<220> FEATURE:
<221> NAME/KEY: Xaa
<222> LOCATION: (11)..(11)
<223> OTHER INFORMATION: Xaa is 4-FPhe

<400> SEQUENCE: 13

Cys Xaa Xaa Xaa Gln Asp Cys Xaa Xaa Gly Xaa Cys
1               5                   10

<210> SEQ ID NO 14
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (3)..(3)
<223> OTHER INFORMATION: Xaa is TrpMe
<220> FEATURE:
<221> NAME/KEY: Xaa
<222> LOCATION: (8)..(8)
<223> OTHER INFORMATION: Xaa is TrpMe
<220> FEATURE:
<221> NAME/KEY: Xaa
<222> LOCATION: (11)..(11)
<223> OTHER INFORMATION: Xaa is 4-FPhe

<400> SEQUENCE: 14

Cys Gln Xaa Leu Glu Asp Cys Xaa Arg Gly Xaa Cys
1               5                   10
```

```
<210> SEQ ID NO 15
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (11)..(11)
<223> OTHER INFORMATION: Xaa is 4-FPhe

<400> SEQUENCE: 15

Cys Gln Trp Leu Glu Asp Cys Trp Arg Gly Xaa Cys
1               5                   10

<210> SEQ ID NO 16
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is AMe
<220> FEATURE:
<221> NAME/KEY: Xaa
<222> LOCATION: (3)..(3)
<223> OTHER INFORMATION: Xaa is TrpMe
<220> FEATURE:
<221> NAME/KEY: Xaa
<222> LOCATION: (4)..(4)
<223> OTHER INFORMATION: Xaa is tBuA
<220> FEATURE:
<221> NAME/KEY: Xaa
<222> LOCATION: (8)..(8)
<223> OTHER INFORMATION: Xaa is TrpMe
<220> FEATURE:
<221> NAME/KEY: Xaa
<222> LOCATION: (9)..(9)
<223> OTHER INFORMATION: Xaa is ADMA
<220> FEATURE:
<221> NAME/KEY: Xaa
<222> LOCATION: (11)..(11)
<223> OTHER INFORMATION: Xaa is 4-FPhe

<400> SEQUENCE: 16

Cys Xaa Xaa Xaa Gln Asp Cys Xaa Xaa Gly Xaa Cys
1               5                   10

<210> SEQ ID NO 17
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (11)..(11)
<223> OTHER INFORMATION: Xaa is 4-FPhe

<400> SEQUENCE: 17

Cys His Trp Leu Glu Asp Cys Trp Arg Gly Xaa Cys
1               5                   10

<210> SEQ ID NO 18
<211> LENGTH: 12
<212> TYPE: PRT
<213> ORGANISM: Artificial
<220> FEATURE:
<223> OTHER INFORMATION: Synthetic Peptide
```

```
-continued

<220> FEATURE:
<221> NAME/KEY: Xaa
<222> LOCATION: (9)..(9)
<223> OTHER INFORMATION: Xaa is ADMA
<220> FEATURE:
<221> NAME/KEY: Xaa
<222> LOCATION: (11)..(11)
<223> OTHER INFORMATION: Xaa is 4-FPhe

<400> SEQUENCE: 18

Cys Gln Trp Leu Gln Asp Cys Trp Xaa Gly Xaa Cys
1               5                   10

<210> SEQ ID NO 19
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (3)..(3)
<223> OTHER INFORMATION: Xaa is 5FTrp
<220> FEATURE:
<221> NAME/KEY: Xaa
<222> LOCATION: (8)..(8)
<223> OTHER INFORMATION: Xaa is 5FTrp
<220> FEATURE:
<221> NAME/KEY: Xaa
<222> LOCATION: (11)..(11)
<223> OTHER INFORMATION: Xaa is 4-FPhe

<400> SEQUENCE: 19

Cys Gln Xaa Leu Glu Asp Cys Xaa Arg Gly Xaa Cys
1               5                   10

<210> SEQ ID NO 20
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (11)..(11)
<223> OTHER INFORMATION: Xaa is 3,4diFPhe

<400> SEQUENCE: 20

Cys Gln Trp Leu Glu Asp Cys Trp Arg Gly Xaa Cys
1               5                   10

<210> SEQ ID NO 21
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (11)..(11)
<223> OTHER INFORMATION: Xaa is 4-FPhe

<400> SEQUENCE: 21

Cys Gln Trp Leu Glu Asn Cys Trp Arg Gly Xaa Cys
1               5                   10

<210> SEQ ID NO 22
<211> LENGTH: 12
<212> TYPE: PRT
<213> ORGANISM: Artificial
<220> FEATURE:
```

```
<223> OTHER INFORMATION: Synthetic Peptide
<220> FEATURE:
<221> NAME/KEY: Xaa
<222> LOCATION: (2)..(2)
<223> OTHER INFORMATION: Xaa is AMe
<220> FEATURE:
<221> NAME/KEY: Xaa
<222> LOCATION: (3)..(3)
<223> OTHER INFORMATION: Xaa is TrpMe
<220> FEATURE:
<221> NAME/KEY: Xaa
<222> LOCATION: (4)..(4)
<223> OTHER INFORMATION: Xaa is tBuA
<220> FEATURE:
<221> NAME/KEY: Xaa
<222> LOCATION: (8)..(8)
<223> OTHER INFORMATION: Xaa is TrpMe
<220> FEATURE:
<221> NAME/KEY: Xaa
<222> LOCATION: (9)..(9)
<223> OTHER INFORMATION: Xaa is AcK
<220> FEATURE:
<221> NAME/KEY: Xaa
<222> LOCATION: (11)..(11)
<223> OTHER INFORMATION: Xaa is 4-FPhe

<400> SEQUENCE: 22

Cys Xaa Xaa Xaa Gln Asp Cys Xaa Xaa Gly Xaa Cys
1               5                   10

<210> SEQ ID NO 23
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is AMe
<220> FEATURE:
<221> NAME/KEY: Xaa
<222> LOCATION: (3)..(3)
<223> OTHER INFORMATION: Xaa is Nal1
<220> FEATURE:
<221> NAME/KEY: Xaa
<222> LOCATION: (4)..(4)
<223> OTHER INFORMATION: Xaa is tBuA
<220> FEATURE:
<221> NAME/KEY: Xaa
<222> LOCATION: (8)..(8)
<223> OTHER INFORMATION: Xaa is TrpMe
<220> FEATURE:
<221> NAME/KEY: Xaa
<222> LOCATION: (9)..(9)
<223> OTHER INFORMATION: Xaa is ADMA
<220> FEATURE:
<221> NAME/KEY: Xaa
<222> LOCATION: (11)..(11)
<223> OTHER INFORMATION: Xaa is 4-FPhe

<400> SEQUENCE: 23

Cys Xaa Xaa Xaa Gln Asp Cys Xaa Xaa Gly Xaa Cys
1               5                   10

<210> SEQ ID NO 24
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (11)..(11)
<223> OTHER INFORMATION: Xaa is 4-BrPhe
```

```
<400> SEQUENCE: 24

Cys Gln Trp Leu Glu Asp Cys Trp Arg Gly Xaa Cys
1               5                   10

<210> SEQ ID NO 25
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (3)..(3)
<223> OTHER INFORMATION: Xaa is Nal1
<220> FEATURE:
<221> NAME/KEY: Xaa
<222> LOCATION: (11)..(11)
<223> OTHER INFORMATION: Xaa is 4-FPhe

<400> SEQUENCE: 25

Cys Gln Xaa Leu Glu Asp Cys Trp Arg Gly Xaa Cys
1               5                   10

<210> SEQ ID NO 26
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (9)..(9)
<223> OTHER INFORMATION: Xaa is ADMA
<220> FEATURE:
<221> NAME/KEY: Xaa
<222> LOCATION: (11)..(11)
<223> OTHER INFORMATION: Xaa is 4-FPhe

<400> SEQUENCE: 26

Cys Trp Trp Leu Gln Asp Cys Trp Xaa Gly Xaa Cys
1               5                   10

<210> SEQ ID NO 27
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is AMe
<220> FEATURE:
<221> NAME/KEY: Xaa
<222> LOCATION: (9)..(9)
<223> OTHER INFORMATION: Xaa is ADMA
<220> FEATURE:
<221> NAME/KEY: Xaa
<222> LOCATION: (11)..(11)
<223> OTHER INFORMATION: Xaa is 4-FPhe

<400> SEQUENCE: 27

Cys Xaa Trp Leu Glu Asp Cys Trp Xaa Gly Xaa Cys
1               5                   10

<210> SEQ ID NO 28
<211> LENGTH: 12
<212> TYPE: PRT
<213> ORGANISM: Artificial
<220> FEATURE:
```

<223> OTHER INFORMATION: Synthetic Peptide
<220> FEATURE:
<221> NAME/KEY: Xaa
<222> LOCATION: (4)..(4)
<223> OTHER INFORMATION: Xaa is iPrMeA
<220> FEATURE:
<221> NAME/KEY: Xaa
<222> LOCATION: (11)..(11)
<223> OTHER INFORMATION: Xaa is 4-FPhe

<400> SEQUENCE: 28

Cys Gln Trp Xaa Glu Asp Cys Trp Arg Gly Xaa Cys
1               5                   10

<210> SEQ ID NO 29
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (11)..(11)
<223> OTHER INFORMATION: Xaa is 3-ClPhe

<400> SEQUENCE: 29

Cys Gln Trp Leu Glu Asp Cys Trp Arg Gly Xaa Cys
1               5                   10

<210> SEQ ID NO 30
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is AMe
<220> FEATURE:
<221> NAME/KEY: Xaa
<222> LOCATION: (3)..(3)
<223> OTHER INFORMATION: Xaa is TrpMe
<220> FEATURE:
<221> NAME/KEY: Xaa
<222> LOCATION: (4)..(4)
<223> OTHER INFORMATION: Xaa is tBuA
<220> FEATURE:
<221> NAME/KEY: Xaa
<222> LOCATION: (8)..(8)
<223> OTHER INFORMATION: Xaa is TrpMe
<220> FEATURE:
<221> NAME/KEY: Xaa
<222> LOCATION: (9)..(9)
<223> OTHER INFORMATION: Xaa is NeopentA
<220> FEATURE:
<221> NAME/KEY: Xaa
<222> LOCATION: (11)..(11)
<223> OTHER INFORMATION: Xaa is 4-FPhe

<400> SEQUENCE: 30

Cys Xaa Xaa Xaa Gln Asp Cys Xaa Xaa Gly Xaa Cys
1               5                   10

<210> SEQ ID NO 31
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)

```
<223> OTHER INFORMATION: Xaa is AMe
<220> FEATURE:
<221> NAME/KEY: Xaa
<222> LOCATION: (3)..(3)
<223> OTHER INFORMATION: Xaa is TrpMe
<220> FEATURE:
<221> NAME/KEY: Xaa
<222> LOCATION: (4)..(4)
<223> OTHER INFORMATION: Xaa is tBuA
<220> FEATURE:
<221> NAME/KEY: Xaa
<222> LOCATION: (8)..(8)
<223> OTHER INFORMATION: Xaa is TrpMe
<220> FEATURE:
<221> NAME/KEY: Xaa
<222> LOCATION: (9)..(9)
<223> OTHER INFORMATION: Xaa is Cha
<220> FEATURE:
<221> NAME/KEY: Xaa
<222> LOCATION: (11)..(11)
<223> OTHER INFORMATION: Xaa is 4-FPhe

<400> SEQUENCE: 31

Cys Xaa Xaa Xaa Gln Asp Cys Xaa Xaa Gly Xaa Cys
1               5                   10

<210> SEQ ID NO 32
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is AMe
<220> FEATURE:
<221> NAME/KEY: Xaa
<222> LOCATION: (3)..(3)
<223> OTHER INFORMATION: Xaa is Nal1
<220> FEATURE:
<221> NAME/KEY: Xaa
<222> LOCATION: (8)..(8)
<223> OTHER INFORMATION: Xaa is TrpMe
<220> FEATURE:
<221> NAME/KEY: Xaa
<222> LOCATION: (9)..(9)
<223> OTHER INFORMATION: Xaa is ADMA
<220> FEATURE:
<221> NAME/KEY: Xaa
<222> LOCATION: (11)..(11)
<223> OTHER INFORMATION: Xaa is 4-FPhe

<400> SEQUENCE: 32

Cys Xaa Xaa Leu Gln Asp Cys Xaa Xaa Gly Xaa Cys
1               5                   10

<210> SEQ ID NO 33
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (11)..(11)
<223> OTHER INFORMATION: Xaa is 3,4,5triFPhe

<400> SEQUENCE: 33

Cys Gln Trp Leu Glu Asp Cys Trp Arg Gly Xaa Cys
1               5                   10

<210> SEQ ID NO 34
```

```
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (3)..(3)
<223> OTHER INFORMATION: Xaa is Nal1
<220> FEATURE:
<221> NAME/KEY: Xaa
<222> LOCATION: (9)..(9)
<223> OTHER INFORMATION: Xaa is ADMA
<220> FEATURE:
<221> NAME/KEY: Xaa
<222> LOCATION: (11)..(11)
<223> OTHER INFORMATION: Xaa is 4-FPhe

<400> SEQUENCE: 34

Cys Gln Xaa Leu Glu Asp Cys Trp Xaa Gly Xaa Cys
1               5                   10

<210> SEQ ID NO 35
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (11)..(11)
<223> OTHER INFORMATION: Xaa is 4-FPhe

<400> SEQUENCE: 35

Cys Gln Trp Leu Phe Asp Cys Trp Arg Gly Xaa Cys
1               5                   10

<210> SEQ ID NO 36
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is AMe
<220> FEATURE:
<221> NAME/KEY: Xaa
<222> LOCATION: (3)..(3)
<223> OTHER INFORMATION: Xaa is TrpMe
<220> FEATURE:
<221> NAME/KEY: Xaa
<222> LOCATION: (4)..(4)
<223> OTHER INFORMATION: Xaa is tBuA
<220> FEATURE:
<221> NAME/KEY: Xaa
<222> LOCATION: (8)..(8)
<223> OTHER INFORMATION: Xaa is 5FTrp
<220> FEATURE:
<221> NAME/KEY: Xaa
<222> LOCATION: (11)..(11)
<223> OTHER INFORMATION: Xaa is 4-FPhe

<400> SEQUENCE: 36

Cys Xaa Xaa Xaa Gln Asp Cys Xaa Arg Gly Xaa Cys
1               5                   10

<210> SEQ ID NO 37
<211> LENGTH: 12
<212> TYPE: PRT
<213> ORGANISM: Artificial
<220> FEATURE:
```

```
<223> OTHER INFORMATION: Synthetic Peptide
<220> FEATURE:
<221> NAME/KEY: Xaa
<222> LOCATION: (11)..(11)
<223> OTHER INFORMATION: Xaa is 3-F,4-ClPhe

<400> SEQUENCE: 37

Cys Gln Trp Leu Glu Asp Cys Trp Arg Gly Xaa Cys
1               5                   10

<210> SEQ ID NO 38
<211> LENGTH: 12
<212> TYPE: PRT
<213> ORGANISM: Artificial
<220> FEATURE:
<223> OTHER INFORMATION: Synthetic Peptide

<400> SEQUENCE: 38

Cys Gln Trp Leu Glu Asp Cys Trp Arg Gly Phe Cys
1               5                   10

<210> SEQ ID NO 39
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (4)..(4)
<223> OTHER INFORMATION: Xaa is tBuA

<400> SEQUENCE: 39

Cys Gln Trp Xaa Glu Asp Cys Trp Arg Gly Phe Cys
1               5                   10

<210> SEQ ID NO 40
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is AMe
<220> FEATURE:
<221> NAME/KEY: Xaa
<222> LOCATION: (3)..(3)
<223> OTHER INFORMATION: Xaa is TrpMe
<220> FEATURE:
<221> NAME/KEY: Xaa
<222> LOCATION: (4)..(4)
<223> OTHER INFORMATION: Xaa is tBuA
<220> FEATURE:
<221> NAME/KEY: Xaa
<222> LOCATION: (8)..(8)
<223> OTHER INFORMATION: Xaa is TrpMe
<220> FEATURE:
<221> NAME/KEY: Xaa
<222> LOCATION: (9)..(9)
<223> OTHER INFORMATION: Xaa is BnA
<220> FEATURE:
<221> NAME/KEY: Xaa
<222> LOCATION: (11)..(11)
<223> OTHER INFORMATION: Xaa is 4-FPhe

<400> SEQUENCE: 40

Cys Xaa Xaa Xaa Gln Asp Cys Xaa Xaa Gly Xaa Cys
1               5                   10
```

```
<210> SEQ ID NO 41
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (11)..(11)
<223> OTHER INFORMATION: Xaa is Nal1

<400> SEQUENCE: 41

Cys Gln Trp Leu Glu Asp Cys Trp Arg Gly Xaa Cys
1               5                   10

<210> SEQ ID NO 42
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (11)..(11)
<223> OTHER INFORMATION: Xaa is Nal2

<400> SEQUENCE: 42

Cys Gln Trp Leu Glu Asp Cys Trp Arg Gly Xaa Cys
1               5                   10

<210> SEQ ID NO 43
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (11)..(11)
<223> OTHER INFORMATION: Xaa is 4-FPhe

<400> SEQUENCE: 43

Cys Gln Trp Met Glu Asp Cys Trp Arg Gly Xaa Cys
1               5                   10

<210> SEQ ID NO 44
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is AMe
<220> FEATURE:
<221> NAME/KEY: Xaa
<222> LOCATION: (3)..(3)
<223> OTHER INFORMATION: Xaa is TrpMe
<220> FEATURE:
<221> NAME/KEY: Xaa
<222> LOCATION: (4)..(4)
<223> OTHER INFORMATION: Xaa is tBuA
<220> FEATURE:
<221> NAME/KEY: Xaa
<222> LOCATION: (5)..(5)
<223> OTHER INFORMATION: Xaa is Aib
<220> FEATURE:
<221> NAME/KEY: Xaa
<222> LOCATION: (8)..(8)
<223> OTHER INFORMATION: Xaa is TrpMe
<220> FEATURE:
<221> NAME/KEY: Xaa
```

```
<222> LOCATION: (9)..(9)
<223> OTHER INFORMATION: Xaa is ADMA
<220> FEATURE:
<221> NAME/KEY: Xaa
<222> LOCATION: (11)..(11)
<223> OTHER INFORMATION: Xaa is 4-FPhe

<400> SEQUENCE: 44

Cys Xaa Xaa Xaa Xaa Asp Cys Xaa Xaa Gly Xaa Cys
1               5                   10

<210> SEQ ID NO 45
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (11)..(11)
<223> OTHER INFORMATION: Xaa is 4-FPhe

<400> SEQUENCE: 45

Cys Gln Trp Ile Glu Asp Cys Trp Arg Gly Xaa Cys
1               5                   10

<210> SEQ ID NO 46
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (11)..(11)
<223> OTHER INFORMATION: Xaa is 3,5diF,4ClPhe

<400> SEQUENCE: 46

Cys Gln Trp Leu Glu Asp Cys Trp Arg Gly Xaa Cys
1               5                   10

<210> SEQ ID NO 47
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (8)..(8)
<223> OTHER INFORMATION: Xaa is 4-ClNal
<220> FEATURE:
<221> NAME/KEY: Xaa
<222> LOCATION: (11)..(11)
<223> OTHER INFORMATION: Xaa is 4-FPhe

<400> SEQUENCE: 47

Cys Gln Trp Leu Glu Asp Cys Xaa Arg Gly Xaa Cys
1               5                   10

<210> SEQ ID NO 48
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (3)..(3)
<223> OTHER INFORMATION: Xaa is Nal1
<220> FEATURE:
```

```
<221> NAME/KEY: Xaa
<222> LOCATION: (9)..(9)
<223> OTHER INFORMATION: Xaa is Harg
<220> FEATURE:
<221> NAME/KEY: Xaa
<222> LOCATION: (11)..(11)
<223> OTHER INFORMATION: Xaa is 4-FPhe

<400> SEQUENCE: 48

Cys Ala Xaa Leu Glu Asp Cys Trp Xaa Gly Xaa Cys
1               5                   10

<210> SEQ ID NO 49
<211> LENGTH: 12
<212> TYPE: PRT
<213> ORGANISM: Artificial
<220> FEATURE:
<223> OTHER INFORMATION: Synthetic Peptide

<400> SEQUENCE: 49

Cys Thr Trp Leu Glu Asp Cys Trp Arg Gly Phe Cys
1               5                   10

<210> SEQ ID NO 50
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (4)..(4)
<223> OTHER INFORMATION: Xaa is CpentA

<400> SEQUENCE: 50

Cys Gln Trp Xaa Glu Asp Cys Trp Arg Gly Phe Cys
1               5                   10

<210> SEQ ID NO 51
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (8)..(8)
<223> OTHER INFORMATION: Xaa is Nal1
<220> FEATURE:
<221> NAME/KEY: Xaa
<222> LOCATION: (11)..(11)
<223> OTHER INFORMATION: Xaa is 4-FPhe

<400> SEQUENCE: 51

Cys Ala Trp Leu Glu Asp Cys Xaa Arg Gly Xaa Cys
1               5                   10

<210> SEQ ID NO 52
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (9)..(9)
<223> OTHER INFORMATION: Xaa is 4-PipA
<220> FEATURE:
<221> NAME/KEY: Xaa
<222> LOCATION: (11)..(11)
<223> OTHER INFORMATION: Xaa is 4-FPhe
```

```
<400> SEQUENCE: 52

Cys Gln Trp Leu Glu Asp Cys Trp Xaa Gly Xaa Cys
1               5                   10

<210> SEQ ID NO 53
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is AMe
<220> FEATURE:
<221> NAME/KEY: Xaa
<222> LOCATION: (3)..(3)
<223> OTHER INFORMATION: Xaa is TrpMe
<220> FEATURE:
<221> NAME/KEY: Xaa
<222> LOCATION: (4)..(4)
<223> OTHER INFORMATION: Xaa is tBuA
<220> FEATURE:
<221> NAME/KEY: Xaa
<222> LOCATION: (8)..(8)
<223> OTHER INFORMATION: Xaa is TrpMe
<220> FEATURE:
<221> NAME/KEY: Xaa
<222> LOCATION: (9)..(9)
<223> OTHER INFORMATION: Xaa is ADMA
<220> FEATURE:
<221> NAME/KEY: Xaa
<222> LOCATION: (11)..(11)
<223> OTHER INFORMATION: Xaa is 4-ClNal

<400> SEQUENCE: 53

Cys Xaa Xaa Xaa Gln Asp Cys Xaa Xaa Gly Xaa Cys
1               5                   10

<210> SEQ ID NO 54
<211> LENGTH: 12
<212> TYPE: PRT
<213> ORGANISM: Artificial
<220> FEATURE:
<223> OTHER INFORMATION: Synthetic Peptide

<400> SEQUENCE: 54

Cys Val Trp Leu Asp Asp Cys Trp Arg Gly Phe Cys
1               5                   10

<210> SEQ ID NO 55
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (11)..(11)
<223> OTHER INFORMATION: Xaa is 3-MePhe

<400> SEQUENCE: 55

Cys Gln Trp Leu Glu Asp Cys Trp Arg Gly Xaa Cys
1               5                   10

<210> SEQ ID NO 56
<211> LENGTH: 12
<212> TYPE: PRT
<213> ORGANISM: Artificial
<220> FEATURE:
```

```
<223> OTHER INFORMATION: Synthetic Peptide

<400> SEQUENCE: 56

Cys His Trp Leu Glu Asp Cys Trp Arg Gly Phe Cys
1               5                   10

<210> SEQ ID NO 57
<211> LENGTH: 12
<212> TYPE: PRT
<213> ORGANISM: Artificial
<220> FEATURE:
<223> OTHER INFORMATION: Synthetic Peptide

<400> SEQUENCE: 57

Cys Thr Trp Leu Asp Asp Cys Trp Arg Gly Phe Cys
1               5                   10

<210> SEQ ID NO 58
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (11)..(11)
<223> OTHER INFORMATION: Xaa is 4-CF3Phe

<400> SEQUENCE: 58

Cys Gln Trp Leu Glu Asp Cys Trp Arg Gly Xaa Cys
1               5                   10

<210> SEQ ID NO 59
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (11)..(11)
<223> OTHER INFORMATION: Xaa is 4-FPhe

<400> SEQUENCE: 59

Cys Gln Trp Leu Glu Asp Cys Trp Arg Ala Xaa Cys
1               5                   10

<210> SEQ ID NO 60
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (4)..(4)
<223> OTHER INFORMATION: Xaa is CproA

<400> SEQUENCE: 60

Cys Gln Trp Xaa Glu Asp Cys Trp Arg Gly Phe Cys
1               5                   10

<210> SEQ ID NO 61
<211> LENGTH: 12
<212> TYPE: PRT
<213> ORGANISM: Artificial
<220> FEATURE:
<223> OTHER INFORMATION: Synthetic Peptide
<220> FEATURE:
```

```
<221> NAME/KEY: Xaa
<222> LOCATION: (9)..(9)
<223> OTHER INFORMATION: Xaa is TriMeK

<400> SEQUENCE: 61

Cys Gln Trp Leu Glu Asp Cys Trp Xaa Gly Phe Cys
1               5                   10

<210> SEQ ID NO 62
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (9)..(9)
<223> OTHER INFORMATION: Xaa is ADMA

<400> SEQUENCE: 62

Cys Gln Trp Leu Glu Asp Cys Trp Xaa Gly Phe Cys
1               5                   10

<210> SEQ ID NO 63
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (4)..(4)
<223> OTHER INFORMATION: Xaa is Cha

<400> SEQUENCE: 63

Cys Gln Trp Xaa Glu Asp Cys Trp Arg Gly Phe Cys
1               5                   10

<210> SEQ ID NO 64
<211> LENGTH: 12
<212> TYPE: PRT
<213> ORGANISM: Artificial
<220> FEATURE:
<223> OTHER INFORMATION: Synthetic Peptide

<400> SEQUENCE: 64

Cys His Trp Leu Glu Asn Cys Trp Arg Gly Phe Cys
1               5                   10

<210> SEQ ID NO 65
<211> LENGTH: 12
<212> TYPE: PRT
<213> ORGANISM: Artificial
<220> FEATURE:
<223> OTHER INFORMATION: Synthetic Peptide

<400> SEQUENCE: 65

Cys Leu Trp Leu Asp Asp Cys Trp Arg Gly Phe Cys
1               5                   10

<210> SEQ ID NO 66
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
```

```
<223> OTHER INFORMATION: Xaa is AMe
<220> FEATURE:
<221> NAME/KEY: Xaa
<222> LOCATION: (3)..(3)
<223> OTHER INFORMATION: Xaa is TrpMe
<220> FEATURE:
<221> NAME/KEY: Xaa
<222> LOCATION: (4)..(4)
<223> OTHER INFORMATION: Xaa is tBuA
<220> FEATURE:
<221> NAME/KEY: Xaa
<222> LOCATION: (8)..(8)
<223> OTHER INFORMATION: Xaa is TrpMe
<220> FEATURE:
<221> NAME/KEY: Xaa
<222> LOCATION: (9)..(9)
<223> OTHER INFORMATION: Xaa is ADMA
<220> FEATURE:
<221> NAME/KEY: Xaa
<222> LOCATION: (11)..(11)
<223> OTHER INFORMATION: Xaa is 3AcNH4ClPhe

<400> SEQUENCE: 66

Cys Xaa Xaa Xaa Gln Asp Cys Xaa Xaa Gly Xaa Cys
1               5                   10

<210> SEQ ID NO 67
<211> LENGTH: 12
<212> TYPE: PRT
<213> ORGANISM: Artificial
<220> FEATURE:
<223> OTHER INFORMATION: Synthetic Peptide

<400> SEQUENCE: 67

Cys Thr Trp Leu Glu Asp Cys Trp His Gly Phe Cys
1               5                   10

<210> SEQ ID NO 68
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (4)..(4)
<223> OTHER INFORMATION: Xaa is Nva

<400> SEQUENCE: 68

Cys Gln Trp Xaa Glu Asp Cys Trp Arg Gly Phe Cys
1               5                   10

<210> SEQ ID NO 69
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (11)..(11)
<223> OTHER INFORMATION: Xaa is 3-FPhe

<400> SEQUENCE: 69

Cys Gln Trp Leu Glu Asp Cys Trp Arg Gly Xaa Cys
1               5                   10

<210> SEQ ID NO 70
<211> LENGTH: 12
<212> TYPE: PRT
<213> ORGANISM: Artificial
```

```
<220> FEATURE:
<223> OTHER INFORMATION: Synthetic Peptide
<220> FEATURE:
<221> NAME/KEY: Xaa
<222> LOCATION: (11)..(11)
<223> OTHER INFORMATION: Xaa is 4-MePhe

<400> SEQUENCE: 70

Cys Gln Trp Leu Glu Asp Cys Trp Arg Gly Xaa Cys
1               5                   10

<210> SEQ ID NO 71
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (4)..(4)
<223> OTHER INFORMATION: Xaa is ChMeA

<400> SEQUENCE: 71

Cys Gln Trp Xaa Glu Asp Cys Trp Arg Gly Phe Cys
1               5                   10

<210> SEQ ID NO 72
<211> LENGTH: 12
<212> TYPE: PRT
<213> ORGANISM: Artificial
<220> FEATURE:
<223> OTHER INFORMATION: Synthetic Peptide

<400> SEQUENCE: 72

Cys His Trp Leu Asp Asp Cys Trp Arg Gly Phe Cys
1               5                   10

<210> SEQ ID NO 73
<211> LENGTH: 12
<212> TYPE: PRT
<213> ORGANISM: Artificial
<220> FEATURE:
<223> OTHER INFORMATION: Synthetic Peptide

<400> SEQUENCE: 73

Cys Asp Trp Leu Asp Asp Cys Trp Arg Gly Phe Cys
1               5                   10

<210> SEQ ID NO 74
<211> LENGTH: 12
<212> TYPE: PRT
<213> ORGANISM: Artificial
<220> FEATURE:
<223> OTHER INFORMATION: Synthetic Peptide

<400> SEQUENCE: 74

Cys Asp Trp Leu Glu Asp Cys Trp Arg Gly Phe Cys
1               5                   10

<210> SEQ ID NO 75
<211> LENGTH: 12
<212> TYPE: PRT
<213> ORGANISM: Artificial
<220> FEATURE:
<223> OTHER INFORMATION: Synthetic Peptide

<400> SEQUENCE: 75

Cys Glu Trp Leu Glu Asp Cys Trp Arg Gly Phe Cys
```

<210> SEQ ID NO 76
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (9)..(9)
<223> OTHER INFORMATION: Xaa is Cit

<400> SEQUENCE: 76

Cys Gln Trp Leu Glu Asp Cys Trp Xaa Gly Phe Cys
1               5                   10

<210> SEQ ID NO 77
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (5)..(5)
<223> OTHER INFORMATION: Xaa is 3-ClPhe
<220> FEATURE:
<221> NAME/KEY: Xaa
<222> LOCATION: (11)..(11)
<223> OTHER INFORMATION: Xaa is 4-FPhe

<400> SEQUENCE: 77

Cys Gln Trp Leu Xaa Asp Cys Trp Arg Gly Xaa Cys
1               5                   10

<210> SEQ ID NO 78
<211> LENGTH: 12
<212> TYPE: PRT
<213> ORGANISM: Artificial
<220> FEATURE:
<223> OTHER INFORMATION: Synthetic Peptide

<400> SEQUENCE: 78

Cys Ala Trp Leu Thr Asp Cys Trp Arg Gly Phe Cys
1               5                   10

<210> SEQ ID NO 79
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (8)..(8)
<223> OTHER INFORMATION: Xaa is 7-OMeTrp
<220> FEATURE:
<221> NAME/KEY: Xaa
<222> LOCATION: (11)..(11)
<223> OTHER INFORMATION: Xaa is 4-FPhe

<400> SEQUENCE: 79

Cys Gln Trp Leu Glu Asp Cys Xaa Arg Gly Xaa Cys
1               5                   10

<210> SEQ ID NO 80
<211> LENGTH: 12
<212> TYPE: PRT
<213> ORGANISM: Artificial

```
<220> FEATURE:
<223> OTHER INFORMATION: Synthetic Peptide
<220> FEATURE:
<221> NAME/KEY: Xaa
<222> LOCATION: (4)..(4)
<223> OTHER INFORMATION: Xaa is Nle

<400> SEQUENCE: 80

Cys Gln Trp Xaa Glu Asp Cys Trp Arg Gly Phe Cys
1               5                   10

<210> SEQ ID NO 81
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (11)..(11)
<223> OTHER INFORMATION: Xaa is 2-FPhe

<400> SEQUENCE: 81

Cys Gln Trp Leu Glu Asp Cys Trp Arg Gly Xaa Cys
1               5                   10

<210> SEQ ID NO 82
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (4)..(4)
<223> OTHER INFORMATION: Xaa is TriFMeA

<400> SEQUENCE: 82

Cys Gln Trp Xaa Glu Asp Cys Trp Arg Gly Phe Cys
1               5                   10

<210> SEQ ID NO 83
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (9)..(9)
<223> OTHER INFORMATION: Xaa is HArg

<400> SEQUENCE: 83

Cys Gln Trp Leu Glu Asp Cys Trp Xaa Gly Phe Cys
1               5                   10

<210> SEQ ID NO 84
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (11)..(11)
<223> OTHER INFORMATION: Xaa is Cha

<400> SEQUENCE: 84

Cys Gln Trp Leu Glu Asp Cys Trp Arg Gly Xaa Cys
1               5                   10
```

```
<210> SEQ ID NO 85
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (3)..(3)
<223> OTHER INFORMATION: Xaa is Nal1
<220> FEATURE:
<221> NAME/KEY: Xaa
<222> LOCATION: (8)..(8)
<223> OTHER INFORMATION: Xaa is Nal1
<220> FEATURE:
<221> NAME/KEY: Xaa
<222> LOCATION: (9)..(9)
<223> OTHER INFORMATION: Xaa is HArg
<220> FEATURE:
<221> NAME/KEY: Xaa
<222> LOCATION: (11)..(11)
<223> OTHER INFORMATION: Xaa is 4-FPhe

<400> SEQUENCE: 85

Cys Ala Xaa Leu Glu Asp Cys Xaa Xaa Gly Xaa Cys
1               5                   10

<210> SEQ ID NO 86
<211> LENGTH: 12
<212> TYPE: PRT
<213> ORGANISM: Artificial
<220> FEATURE:
<223> OTHER INFORMATION: Synthetic Peptide

<400> SEQUENCE: 86

Cys Arg Trp Leu Asp Asp Cys Trp Gln Gly Phe Cys
1               5                   10

<210> SEQ ID NO 87
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (11)..(11)
<223> OTHER INFORMATION: Xaa is 4-FPhe

<400> SEQUENCE: 87

Cys Gln Trp Leu Gln Asp Cys Phe Arg Gly Xaa Cys
1               5                   10

<210> SEQ ID NO 88
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (11)..(11)
<223> OTHER INFORMATION: Xaa is 4-CNPhe

<400> SEQUENCE: 88

Cys Gln Trp Leu Glu Asp Cys Trp Arg Gly Xaa Cys
1               5                   10

<210> SEQ ID NO 89
```

```
<211> LENGTH: 12
<212> TYPE: PRT
<213> ORGANISM: Artificial
<220> FEATURE:
<223> OTHER INFORMATION: Synthetic Peptide

<400> SEQUENCE: 89

Cys Asn Trp Leu Glu Asp Cys Trp His Gly Phe Cys
1               5                   10

<210> SEQ ID NO 90
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (11)..(11)
<223> OTHER INFORMATION: Xaa is 4-FPhe

<400> SEQUENCE: 90

Cys Ala Trp Leu Glu Asp Cys Trp Arg Gly Xaa Cys
1               5                   10

<210> SEQ ID NO 91
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (11)..(11)
<223> OTHER INFORMATION: Xaa is 3-CNPhe

<400> SEQUENCE: 91

Cys Gln Trp Leu Glu Asp Cys Trp Arg Gly Xaa Cys
1               5                   10

<210> SEQ ID NO 92
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (9)..(9)
<223> OTHER INFORMATION: Xaa is Can

<400> SEQUENCE: 92

Cys Gln Trp Leu Glu Asp Cys Trp Xaa Gly Phe Cys
1               5                   10

<210> SEQ ID NO 93
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (11)..(11)
<223> OTHER INFORMATION: Xaa is 3-ThienylA

<400> SEQUENCE: 93

Cys Gln Trp Leu Glu Asp Cys Trp Arg Gly Xaa Cys
1               5                   10
```

<210> SEQ ID NO 94
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (9)..(9)
<223> OTHER INFORMATION: Xaa is Agb

<400> SEQUENCE: 94

Cys Gln Trp Leu Glu Asp Cys Trp Xaa Gly Phe Cys
1               5                   10

<210> SEQ ID NO 95
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (9)..(9)
<223> OTHER INFORMATION: Xaa is ADMA
<220> FEATURE:
<221> NAME/KEY: Xaa
<222> LOCATION: (11)..(11)
<223> OTHER INFORMATION: Xaa is 4-FPhe

<400> SEQUENCE: 95

Cys Ala Trp Leu Glu Asp Cys Trp Xaa Gly Xaa Cys
1               5                   10

<210> SEQ ID NO 96
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (11)..(11)
<223> OTHER INFORMATION: Xaa is 2ThienylA

<400> SEQUENCE: 96

Cys Gln Trp Leu Glu Asp Cys Trp Arg Gly Xaa Cys
1               5                   10

<210> SEQ ID NO 97
<211> LENGTH: 12
<212> TYPE: PRT
<213> ORGANISM: Artificial
<220> FEATURE:
<223> OTHER INFORMATION: Synthetic Peptide

<400> SEQUENCE: 97

Cys Glu Trp Leu Glu Asp Cys Trp Lys Gly Phe Cys
1               5                   10

<210> SEQ ID NO 98
<211> LENGTH: 12
<212> TYPE: PRT
<213> ORGANISM: Artificial
<220> FEATURE:
<223> OTHER INFORMATION: Synthetic Peptide

<400> SEQUENCE: 98

Cys Phe Trp Leu Glu Asp Cys Trp Arg Gly Tyr Cys

<210> SEQ ID NO 99
<211> LENGTH: 12
<212> TYPE: PRT
<213> ORGANISM: Artificial
<220> FEATURE:
<223> OTHER INFORMATION: Synthetic Peptide

<400> SEQUENCE: 99

Cys Gln Trp Leu Glu Asp Cys Trp Arg Gly Trp Cys
1               5                   10

<210> SEQ ID NO 100
<211> LENGTH: 12
<212> TYPE: PRT
<213> ORGANISM: Artificial
<220> FEATURE:
<223> OTHER INFORMATION: Synthetic Peptide

<400> SEQUENCE: 100

Cys Asp Trp Leu Asp Asp Cys Trp Lys Gly Phe Cys
1               5                   10

<210> SEQ ID NO 101
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (11)..(11)
<223> OTHER INFORMATION: Xaa is 4-MeOPhe

<400> SEQUENCE: 101

Cys Gln Trp Leu Glu Asp Cys Trp Arg Gly Xaa Cys
1               5                   10

<210> SEQ ID NO 102
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (11)..(11)
<223> OTHER INFORMATION: Xaa is 3-BrPhe

<400> SEQUENCE: 102

Cys Gln Trp Leu Glu Asp Cys Trp Arg Gly Xaa Cys
1               5                   10

<210> SEQ ID NO 103
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (5)..(5)
<223> OTHER INFORMATION: Xaa is 3-ClPhe
<220> FEATURE:
<221> NAME/KEY: Xaa
<222> LOCATION: (11)..(11)
<223> OTHER INFORMATION: Xaa is 4-FPhe

<400> SEQUENCE: 103

Cys Trp Trp Leu Xaa Asp Cys Trp Arg Gly Xaa Cys
1               5                   10

<210> SEQ ID NO 104
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (3)..(3)
<223> OTHER INFORMATION: Xaa is ButG
<220> FEATURE:
<221> NAME/KEY: Xaa
<222> LOCATION: (9)..(9)
<223> OTHER INFORMATION: Xaa is ButG
<220> FEATURE:
<221> NAME/KEY: Xaa
<222> LOCATION: (11)..(11)
<223> OTHER INFORMATION: Xaa is 4-FPhe

<400> SEQUENCE: 104

Cys Gln Xaa Leu Glu Asp Cys Trp Xaa Gly Xaa Cys
1               5                   10

<210> SEQ ID NO 105
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (11)..(11)
<223> OTHER INFORMATION: Xaa is 2PyrA

<400> SEQUENCE: 105

Cys Gln Trp Leu Glu Asp Cys Trp Arg Gly Xaa Cys
1               5                   10

<210> SEQ ID NO 106
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (4)..(4)
<223> OTHER INFORMATION: Xaa is M(O)

<400> SEQUENCE: 106

Cys Gln Trp Xaa Glu Asp Cys Trp Arg Gly Phe Cys
1               5                   10

<210> SEQ ID NO 107
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (11)..(11)
<223> OTHER INFORMATION: Xaa is BnA

<400> SEQUENCE: 107

Cys Gln Trp Leu Glu Asp Cys Trp Arg Gly Xaa Cys
1               5                   10

<210> SEQ ID NO 108
<211> LENGTH: 12
<212> TYPE: PRT
<213> ORGANISM: Artificial
<220> FEATURE:
<223> OTHER INFORMATION: Synthetic Peptide

<400> SEQUENCE: 108

Cys Gln Trp Leu Glu Asp Cys Trp Ala Gly Phe Cys
1               5                   10

<210> SEQ ID NO 109
<211> LENGTH: 12
<212> TYPE: PRT
<213> ORGANISM: Artificial
<220> FEATURE:
<223> OTHER INFORMATION: Synthetic Peptide

<400> SEQUENCE: 109

Cys Thr Ile Leu Glu Asp Cys Trp Met Gly Phe Cys
1               5                   10

<210> SEQ ID NO 110
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (4)..(4)
<223> OTHER INFORMATION: Xaa is Abu

<400> SEQUENCE: 110

Cys Gln Trp Xaa Glu Asp Cys Trp Arg Gly Phe Cys
1               5                   10

<210> SEQ ID NO 111
<211> LENGTH: 12
<212> TYPE: PRT
<213> ORGANISM: Artificial
<220> FEATURE:
<223> OTHER INFORMATION: Synthetic Peptide

<400> SEQUENCE: 111

Cys His Trp Leu Glu Asn Cys Trp Ala Gly Phe Cys
1               5                   10

<210> SEQ ID NO 112
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (11)..(11)
<223> OTHER INFORMATION: Xaa is PentFPhe

<400> SEQUENCE: 112

Cys Gln Trp Leu Glu Asp Cys Trp Arg Gly Xaa Cys
1               5                   10

<210> SEQ ID NO 113
<211> LENGTH: 12
<212> TYPE: PRT
<213> ORGANISM: Artificial

```
<220> FEATURE:
<223> OTHER INFORMATION: Synthetic Peptide
<220> FEATURE:
<221> NAME/KEY: Xaa
<222> LOCATION: (4)..(4)
<223> OTHER INFORMATION: Xaa is LMe
<220> FEATURE:
<221> NAME/KEY: Xaa
<222> LOCATION: (11)..(11)
<223> OTHER INFORMATION: Xaa is 4-FPhe

<400> SEQUENCE: 113

Cys Gln Trp Xaa Glu Asp Cys Trp Arg Gly Xaa Cys
1               5                   10

<210> SEQ ID NO 114
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (9)..(9)
<223> OTHER INFORMATION: Xaa is Dap

<400> SEQUENCE: 114

Cys Gln Trp Leu Glu Asp Cys Trp Xaa Gly Phe Cys
1               5                   10

<210> SEQ ID NO 115
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (11)..(11)
<223> OTHER INFORMATION: Xaa is 4-PyrA

<400> SEQUENCE: 115

Cys Gln Trp Leu Glu Asp Cys Trp Arg Gly Xaa Cys
1               5                   10

<210> SEQ ID NO 116
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (11)..(11)
<223> OTHER INFORMATION: Xaa is 3-PyrA

<400> SEQUENCE: 116

Cys Gln Trp Leu Glu Asp Cys Trp Arg Gly Xaa Cys
1               5                   10

<210> SEQ ID NO 117
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (9)..(9)
<223> OTHER INFORMATION: Xaa is Dap
```

```
<400> SEQUENCE: 117

Cys His Trp Leu Glu Asn Cys Trp Xaa Gly Phe Cys
1               5                   10

<210> SEQ ID NO 118
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (4)..(4)
<223> OTHER INFORMATION: Xaa is 4-MenL
<220> FEATURE:
<221> NAME/KEY: Xaa
<222> LOCATION: (11)..(11)
<223> OTHER INFORMATION: Xaa is 4-FPhe

<400> SEQUENCE: 118

Cys Gln Trp Xaa Glu Asp Cys Trp Arg Gly Xaa Cys
1               5                   10

<210> SEQ ID NO 119
<211> LENGTH: 15
<212> TYPE: PRT
<213> ORGANISM: Artificial
<220> FEATURE:
<223> OTHER INFORMATION: Synthetic Peptide

<400> SEQUENCE: 119

Cys Glu Ser Leu Asp Pro Trp Ser Cys Pro Val Trp Trp Arg Cys
1               5                   10                  15

<210> SEQ ID NO 120
<211> LENGTH: 15
<212> TYPE: PRT
<213> ORGANISM: Artificial
<220> FEATURE:
<223> OTHER INFORMATION: Synthetic Peptide

<400> SEQUENCE: 120

Cys Pro Ser Leu Asp Pro Trp Thr Cys Gln Ser Trp Tyr Glu Cys
1               5                   10                  15

<210> SEQ ID NO 121
<211> LENGTH: 15
<212> TYPE: PRT
<213> ORGANISM: Artificial
<220> FEATURE:
<223> OTHER INFORMATION: Synthetic Peptide

<400> SEQUENCE: 121

Cys Thr Glu Leu Asp Pro Trp Thr Cys Glu Thr Trp Trp Leu Cys
1               5                   10                  15

<210> SEQ ID NO 122
<211> LENGTH: 15
<212> TYPE: PRT
<213> ORGANISM: Artificial
<220> FEATURE:
<223> OTHER INFORMATION: Synthetic Peptide

<400> SEQUENCE: 122

Cys Arg Asp Leu Asp Pro Trp Thr Cys Ser Ser Trp Trp Leu Cys
1               5                   10                  15
```

```
<210> SEQ ID NO 123
<211> LENGTH: 15
<212> TYPE: PRT
<213> ORGANISM: Artificial
<220> FEATURE:
<223> OTHER INFORMATION: Synthetic Peptide

<400> SEQUENCE: 123

Cys Ala Asp Leu Asp Pro Trp Thr Cys Pro Asn Trp Trp Leu Cys
1               5                   10                  15

<210> SEQ ID NO 124
<211> LENGTH: 15
<212> TYPE: PRT
<213> ORGANISM: Artificial
<220> FEATURE:
<223> OTHER INFORMATION: Synthetic Peptide

<400> SEQUENCE: 124

Cys Val Asp Leu Asp Pro Trp Thr Cys Glu Gln Trp Trp Leu Cys
1               5                   10                  15

<210> SEQ ID NO 125
<211> LENGTH: 15
<212> TYPE: PRT
<213> ORGANISM: Artificial
<220> FEATURE:
<223> OTHER INFORMATION: Synthetic Peptide

<400> SEQUENCE: 125

Cys Lys Asp Leu Asp Pro Trp Thr Cys Ser Ser Trp Trp Glu Cys
1               5                   10                  15

<210> SEQ ID NO 126
<211> LENGTH: 15
<212> TYPE: PRT
<213> ORGANISM: Artificial
<220> FEATURE:
<223> OTHER INFORMATION: Synthetic Peptide

<400> SEQUENCE: 126

Cys Arg Asp Leu Asp Pro Trp Thr Cys Pro Thr Trp Trp Thr Cys
1               5                   10                  15

<210> SEQ ID NO 127
<211> LENGTH: 15
<212> TYPE: PRT
<213> ORGANISM: Artificial
<220> FEATURE:
<223> OTHER INFORMATION: Synthetic Peptide

<400> SEQUENCE: 127

Cys Thr Asp Leu Asp Pro Trp Thr Cys Asn Ser Trp Trp Leu Cys
1               5                   10                  15

<210> SEQ ID NO 128
<211> LENGTH: 15
<212> TYPE: PRT
<213> ORGANISM: Artificial
<220> FEATURE:
<223> OTHER INFORMATION: Synthetic Peptide

<400> SEQUENCE: 128

Cys Arg Asp Leu Asp Pro Trp Thr Cys Glu Glu Trp Trp Leu Cys
1               5                   10                  15

<210> SEQ ID NO 129
```

```
<211> LENGTH: 15
<212> TYPE: PRT
<213> ORGANISM: Artificial
<220> FEATURE:
<223> OTHER INFORMATION: Synthetic Peptide

<400> SEQUENCE: 129

Cys Arg Glu Leu Asp Pro Trp Thr Cys Glu Thr Trp Trp Leu Cys
1               5                   10                  15

<210> SEQ ID NO 130
<211> LENGTH: 15
<212> TYPE: PRT
<213> ORGANISM: Artificial
<220> FEATURE:
<223> OTHER INFORMATION: Synthetic Peptide

<400> SEQUENCE: 130

Cys Lys Glu Leu Asp Pro Trp Thr Cys Glu Thr Trp Trp Leu Cys
1               5                   10                  15

<210> SEQ ID NO 131
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is Orn

<400> SEQUENCE: 131

Cys Xaa Glu Leu Asp Pro Trp Thr Cys Glu Thr Trp Trp Leu Cys
1               5                   10                  15

<210> SEQ ID NO 132
<211> LENGTH: 15
<212> TYPE: PRT
<213> ORGANISM: Artificial
<220> FEATURE:
<223> OTHER INFORMATION: Synthetic Peptide

<400> SEQUENCE: 132

Cys Gln Glu Leu Asp Pro Trp Thr Cys Glu Thr Trp Trp Leu Cys
1               5                   10                  15

<210> SEQ ID NO 133
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (6)..(6)
<223> OTHER INFORMATION: Xaa is diF-P

<400> SEQUENCE: 133

Cys Thr Glu Leu Asp Xaa Trp Thr Cys Glu Thr Trp Trp Leu Cys
1               5                   10                  15

<210> SEQ ID NO 134
<211> LENGTH: 15
<212> TYPE: PRT
<213> ORGANISM: Artificial
<220> FEATURE:
<223> OTHER INFORMATION: Synthetic Peptide
```

```
<400> SEQUENCE: 134

Cys Val Asp Leu Asp Pro Trp Ser Cys Glu Asp Trp Trp Leu Cys
1               5                   10                  15

<210> SEQ ID NO 135
<211> LENGTH: 15
<212> TYPE: PRT
<213> ORGANISM: Artificial
<220> FEATURE:
<223> OTHER INFORMATION: Synthetic Peptide

<400> SEQUENCE: 135

Cys Pro Asp Leu Asp Pro Trp Thr Cys Pro Leu Trp Trp Thr Cys
1               5                   10                  15

<210> SEQ ID NO 136
<211> LENGTH: 15
<212> TYPE: PRT
<213> ORGANISM: Artificial
<220> FEATURE:
<223> OTHER INFORMATION: Synthetic Peptide

<400> SEQUENCE: 136

Cys Pro Asp Leu Asp Pro Trp Thr Cys Ser Asp Trp Trp Leu Cys
1               5                   10                  15

<210> SEQ ID NO 137
<211> LENGTH: 15
<212> TYPE: PRT
<213> ORGANISM: Artificial
<220> FEATURE:
<223> OTHER INFORMATION: Synthetic Peptide

<400> SEQUENCE: 137

Cys Arg Asp Leu Asp Pro Trp Thr Cys Asp Ser Trp Trp Leu Cys
1               5                   10                  15

<210> SEQ ID NO 138
<211> LENGTH: 15
<212> TYPE: PRT
<213> ORGANISM: Artificial
<220> FEATURE:
<223> OTHER INFORMATION: Synthetic Peptide

<400> SEQUENCE: 138

Cys Thr Asp Leu Asp Pro Trp Thr Cys Pro Asp Trp Trp Leu Cys
1               5                   10                  15

<210> SEQ ID NO 139
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (6)..(6)
<223> OTHER INFORMATION: Xaa is 5-Ph-P

<400> SEQUENCE: 139

Cys Thr Glu Leu Asp Xaa Trp Thr Cys Glu Thr Trp Trp Leu Cys
1               5                   10                  15

<210> SEQ ID NO 140
<211> LENGTH: 15
<212> TYPE: PRT
<213> ORGANISM: Artificial
```

```
<220> FEATURE:
<223> OTHER INFORMATION: Synthetic Peptide
<220> FEATURE:
<221> NAME/KEY: Xaa
<222> LOCATION: (6)..(6)
<223> OTHER INFORMATION: Xaa is Chx-P

<400> SEQUENCE: 140

Cys Thr Glu Leu Asp Xaa Trp Thr Cys Glu Thr Trp Trp Leu Cys
1               5                   10                  15

<210> SEQ ID NO 141
<211> LENGTH: 13
<212> TYPE: PRT
<213> ORGANISM: Artificial
<220> FEATURE:
<223> OTHER INFORMATION: Synthetic Peptide

<400> SEQUENCE: 141

Cys Asp Trp Gln Trp Ser Tyr Asp Cys Trp Leu Pro Cys
1               5                   10

<210> SEQ ID NO 142
<211> LENGTH: 13
<212> TYPE: PRT
<213> ORGANISM: Artificial
<220> FEATURE:
<223> OTHER INFORMATION: Synthetic Peptide

<400> SEQUENCE: 142

Cys Asp Trp Val Trp Glu Tyr Asp Cys Trp Leu Pro Cys
1               5                   10

<210> SEQ ID NO 143
<211> LENGTH: 13
<212> TYPE: PRT
<213> ORGANISM: Artificial
<220> FEATURE:
<223> OTHER INFORMATION: Synthetic Peptide

<400> SEQUENCE: 143

Cys Asp Trp Asp Trp Glu Tyr Asp Cys Trp Leu His Cys
1               5                   10

<210> SEQ ID NO 144
<211> LENGTH: 13
<212> TYPE: PRT
<213> ORGANISM: Artificial
<220> FEATURE:
<223> OTHER INFORMATION: Synthetic Peptide

<400> SEQUENCE: 144

Cys Asp Trp His Trp Glu Tyr Asp Cys Trp Leu Ser Cys
1               5                   10

<210> SEQ ID NO 145
<211> LENGTH: 13
<212> TYPE: PRT
<213> ORGANISM: Artificial
<220> FEATURE:
<223> OTHER INFORMATION: Synthetic Peptide

<400> SEQUENCE: 145

Cys Thr Trp Asn Trp Glu Tyr Asp Cys Trp Leu Asp Cys
1               5                   10

<210> SEQ ID NO 146
```

```
<211> LENGTH: 13
<212> TYPE: PRT
<213> ORGANISM: Artificial
<220> FEATURE:
<223> OTHER INFORMATION: Synthetic Peptide

<400> SEQUENCE: 146

Cys Glu Trp Asn Trp Ala Tyr Asp Cys Trp Leu Gly Cys
1               5                   10

<210> SEQ ID NO 147
<211> LENGTH: 13
<212> TYPE: PRT
<213> ORGANISM: Artificial
<220> FEATURE:
<223> OTHER INFORMATION: Synthetic Peptide

<400> SEQUENCE: 147

Cys Glu Trp Asn Trp Glu Tyr Asp Cys Trp Leu Asp Cys
1               5                   10

<210> SEQ ID NO 148
<211> LENGTH: 13
<212> TYPE: PRT
<213> ORGANISM: Artificial
<220> FEATURE:
<223> OTHER INFORMATION: Synthetic Peptide

<400> SEQUENCE: 148

Cys Gln Trp Asn Trp Thr Tyr Asp Cys Trp Leu Gly Cys
1               5                   10

<210> SEQ ID NO 149
<211> LENGTH: 13
<212> TYPE: PRT
<213> ORGANISM: Artificial
<220> FEATURE:
<223> OTHER INFORMATION: Synthetic Peptide

<400> SEQUENCE: 149

Cys Lys Trp Met Trp Glu Tyr Asp Cys Trp Leu Ser Cys
1               5                   10

<210> SEQ ID NO 150
<211> LENGTH: 13
<212> TYPE: PRT
<213> ORGANISM: Artificial
<220> FEATURE:
<223> OTHER INFORMATION: Synthetic Peptide

<400> SEQUENCE: 150

Cys Asp Trp Gln Trp Glu Tyr Asp Cys Trp Leu Ser Cys
1               5                   10

<210> SEQ ID NO 151
<211> LENGTH: 13
<212> TYPE: PRT
<213> ORGANISM: Artificial
<220> FEATURE:
<223> OTHER INFORMATION: Synthetic Peptide

<400> SEQUENCE: 151

Cys Asp Trp Asn Trp Thr Tyr Asp Cys Trp Leu Asp Cys
1               5                   10

<210> SEQ ID NO 152
<211> LENGTH: 13
```

```
<212> TYPE: PRT
<213> ORGANISM: Artificial
<220> FEATURE:
<223> OTHER INFORMATION: Synthetic Peptide

<400> SEQUENCE: 152

Cys Asp Trp Asn Trp Ser Tyr Asp Cys Trp Leu Pro Cys
1               5                   10

<210> SEQ ID NO 153
<211> LENGTH: 13
<212> TYPE: PRT
<213> ORGANISM: Artificial
<220> FEATURE:
<223> OTHER INFORMATION: Synthetic Peptide

<400> SEQUENCE: 153

Cys Asp Trp Asp Trp Asp Tyr Asp Cys Trp Leu Pro Cys
1               5                   10

<210> SEQ ID NO 154
<211> LENGTH: 13
<212> TYPE: PRT
<213> ORGANISM: Artificial
<220> FEATURE:
<223> OTHER INFORMATION: Synthetic Peptide

<400> SEQUENCE: 154

Cys Val Trp His Trp Glu Tyr Asp Cys Trp Leu Asp Cys
1               5                   10

<210> SEQ ID NO 155
<211> LENGTH: 13
<212> TYPE: PRT
<213> ORGANISM: Artificial
<220> FEATURE:
<223> OTHER INFORMATION: Synthetic Peptide

<400> SEQUENCE: 155

Cys Ile Trp Asp Trp Lys Tyr Asp Cys Trp Leu Gly Cys
1               5                   10

<210> SEQ ID NO 156
<211> LENGTH: 14
<212> TYPE: PRT
<213> ORGANISM: Artificial
<220> FEATURE:
<223> OTHER INFORMATION: Synthetic Peptide

<400> SEQUENCE: 156

Cys Ser Leu Asp Pro Trp Ser Cys His Asn Trp Trp Thr Cys
1               5                   10

<210> SEQ ID NO 157
<211> LENGTH: 14
<212> TYPE: PRT
<213> ORGANISM: Artificial
<220> FEATURE:
<223> OTHER INFORMATION: Synthetic Peptide

<400> SEQUENCE: 157

Cys Ala Leu Asp Pro Trp Val Cys Pro Gln Trp Trp Asp Cys
1               5                   10

<210> SEQ ID NO 158
<211> LENGTH: 15
<212> TYPE: PRT
```

```
<213> ORGANISM: Artificial
<220> FEATURE:
<223> OTHER INFORMATION: Synthetic Peptide

<400> SEQUENCE: 158

Cys Gln Glu His Asp Trp Tyr Cys Leu Leu Tyr Gln Pro Glu Cys
1               5                   10                  15

<210> SEQ ID NO 159
<211> LENGTH: 15
<212> TYPE: PRT
<213> ORGANISM: Artificial
<220> FEATURE:
<223> OTHER INFORMATION: Synthetic Peptide

<400> SEQUENCE: 159

Cys Asp Glu Leu Asp Ile Pro Cys Trp Ile Phe Lys Thr Leu Cys
1               5                   10                  15

<210> SEQ ID NO 160

<400> SEQUENCE: 160

000

<210> SEQ ID NO 161
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (3)..(3)
<223> OTHER INFORMATION: Xaa is modG
<220> FEATURE:
<221> NAME/KEY: Xaa
<222> LOCATION: (4)..(4)
<223> OTHER INFORMATION: Xaa is tBuA
<220> FEATURE:
<221> NAME/KEY: Xaa
<222> LOCATION: (8)..(8)
<223> OTHER INFORMATION: Xaa is TrpMe
<220> FEATURE:
<221> NAME/KEY: Xaa
<222> LOCATION: (9)..(9)
<223> OTHER INFORMATION: Xaa is modG
<220> FEATURE:
<221> NAME/KEY: Xaa
<222> LOCATION: (11)..(11)
<223> OTHER INFORMATION: Xaa is 4-FPhe

<400> SEQUENCE: 161

Cys Gln Xaa Xaa Glu Asp Cys Xaa Xaa Gly Xaa Cys
1               5                   10

<210> SEQ ID NO 162
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (3)..(3)
<223> OTHER INFORMATION: Xaa is modG
<220> FEATURE:
<221> NAME/KEY: Xaa
<222> LOCATION: (4)..(4)
<223> OTHER INFORMATION: Xaa is tBuA
<220> FEATURE:
<221> NAME/KEY: Xaa
```

```
<222> LOCATION: (8)..(8)
<223> OTHER INFORMATION: Xaa is TrpMe
<220> FEATURE:
<221> NAME/KEY: Xaa
<222> LOCATION: (9)..(9)
<223> OTHER INFORMATION: Xaa is modG
<220> FEATURE:
<221> NAME/KEY: Xaa
<222> LOCATION: (11)..(11)
<223> OTHER INFORMATION: Xaa is 4-FPhe

<400> SEQUENCE: 162

Cys Gln Xaa Xaa Gln Asp Cys Xaa Xaa Gly Xaa Cys
1               5                   10

<210> SEQ ID NO 163
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is NMeA
<220> FEATURE:
<221> NAME/KEY: Xaa
<222> LOCATION: (3)..(3)
<223> OTHER INFORMATION: Xaa is modG
<220> FEATURE:
<221> NAME/KEY: Xaa
<222> LOCATION: (4)..(4)
<223> OTHER INFORMATION: Xaa is tBuA
<220> FEATURE:
<221> NAME/KEY: Xaa
<222> LOCATION: (8)..(8)
<223> OTHER INFORMATION: Xaa is TrpMe
<220> FEATURE:
<221> NAME/KEY: Xaa
<222> LOCATION: (9)..(9)
<223> OTHER INFORMATION: Xaa is modG
<220> FEATURE:
<221> NAME/KEY: Xaa
<222> LOCATION: (11)..(11)
<223> OTHER INFORMATION: Xaa is 4-FPhe

<400> SEQUENCE: 163

Cys Xaa Xaa Xaa Gln Asp Cys Xaa Xaa Gly Xaa Cys
1               5                   10

<210> SEQ ID NO 164
<211> LENGTH: 183
<212> TYPE: PRT
<213> ORGANISM: Human

<400> SEQUENCE: 164

Met Pro Leu Leu Leu Leu Leu Pro Leu Leu Trp Ala Gly Ala Leu Ala
1               5                   10                  15

His Asn His Asn His Asn His Asn His Asn His Asn Ala Ala Glu Asn
                20                  25                  30

Leu Tyr Phe Gln Tyr Asp Phe Thr Asn Cys Asp Phe Glu Lys Ile Lys
            35                  40                  45

Ala Ala Tyr Leu Ser Thr Ile Ser Lys Asp Leu Ile Thr Tyr Met Ser
        50                  55                  60

Gly Thr Lys Ser Thr Glu Phe Asn Asn Thr Val Ser Cys Ser Asn Arg
65                  70                  75                  80

Pro His Cys Leu Thr Glu Ile Gln Ser Leu Thr Phe Asn Pro Thr Ala
                85                  90                  95
```

Gly Cys Ala Ser Leu Ala Lys Glu Met Phe Ala Met Lys Thr Lys Ala
            100                 105                 110

Ala Leu Ala Ile Trp Cys Pro Gly Tyr Ser Glu Thr Gln Ile Asn Ala
            115                 120                 125

Thr Gln Ala Met Lys Lys Arg Arg Lys Arg Lys Val Thr Thr Asn Lys
            130                 135                 140

Cys Leu Glu Gln Val Ser Gln Leu Gln Gly Leu Trp Arg Arg Phe Asn
145                 150                 155                 160

Arg Pro Leu Leu Lys Gln Gln Gly Leu Asn Asp Ile Phe Glu Ala
            165                 170                 175

Gln Lys Ile Glu Trp His Glu
            180

<210> SEQ ID NO 165
<211> LENGTH: 247
<212> TYPE: PRT
<213> ORGANISM: Human

<400> SEQUENCE: 165

Met Glu Thr Asp Thr Leu Leu Leu Trp Val Leu Leu Leu Trp Val Pro
1               5                   10                  15

Gly Ser Thr Gly His Asn His Asn His Asn His Asn His Asn His Asn
            20                  25                  30

Ala Ala Glu Asn Leu Tyr Phe Gln Gly Ala Ala Glu Gly Val Gln Ile
            35                  40                  45

Gln Ile Ile Tyr Phe Asn Leu Glu Thr Val Gln Val Thr Trp Asn Ala
            50                  55                  60

Ser Lys Tyr Ser Arg Thr Asn Leu Thr Phe His Tyr Arg Phe Asn Gly
65                  70                  75                  80

Asp Glu Ala Tyr Asp Gln Cys Thr Asn Tyr Leu Leu Gln Glu Gly His
            85                  90                  95

Thr Ser Gly Cys Leu Leu Asp Ala Glu Gln Arg Asp Asp Ile Leu Tyr
            100                 105                 110

Phe Ser Ile Arg Asn Gly Thr His Pro Val Phe Thr Ala Ser Arg Trp
            115                 120                 125

Met Val Tyr Tyr Leu Lys Pro Ser Ser Pro Lys His Val Arg Phe Ser
            130                 135                 140

Trp His Gln Asp Ala Val Thr Val Thr Cys Ser Asp Leu Ser Tyr Gly
145                 150                 155                 160

Asp Leu Leu Tyr Glu Val Gln Tyr Arg Ser Pro Phe Asp Thr Glu Trp
            165                 170                 175

Gln Ser Lys Gln Glu Asn Thr Cys Asn Val Thr Ile Glu Gly Leu Asp
            180                 185                 190

Ala Glu Lys Cys Tyr Ser Phe Trp Val Arg Val Lys Ala Met Glu Asp
            195                 200                 205

Val Tyr Gly Pro Asp Thr Tyr Pro Ser Asp Trp Ser Glu Val Thr Cys
            210                 215                 220

Trp Gln Arg Gly Glu Ile Arg Asp Ala Cys Ala Glu Thr Pro Thr Pro
225                 230                 235                 240

Pro Lys Pro Lys Leu Ser Lys
            245

US 11,866,518 B2

BICYCLIC PEPTIDE LIGANDS SPECIFIC FOR TSLP

SEQUENCE LISTING

The instant application contains a Sequence Listing which has been submitted electronically in ASCII format and is hereby incorporated by reference in its entirety. The ASCII copy, created on Apr. 6, 2020, is named "182895_SL.txt" and is 51 kilobytes in size.

FIELD OF THE INVENTION

The present invention relates to polypeptides which are covalently bound to molecular scaffolds such that two or more peptide loops are subtended between attachment points to the scaffold. In particular, the invention describes peptides which are high affinity binders of thymic stromal lymphopoietin (TSLP). The invention also includes pharmaceutical compositions comprising said peptide ligands and to the use of said peptide ligands in preventing, suppressing or treating a disease or disorder mediated by TSLP.

BACKGROUND OF THE INVENTION

Asthma is a common long-term inflammatory disease of the airways of the lungs. It is characterized by variable and recurring symptoms, reversible airflow obstruction, and easily triggered bronchospasms. Symptoms include episodes of wheezing, coughing, chest tightness, and shortness of breath. These may occur a few times a day or a few times per week. Depending on the person, asthma symptoms may become worse at night or with exercise.

Asthma is thought to be caused by a combination of genetic and environmental factors. Environmental factors include exposure to air pollution and allergens. Other potential triggers include medications such as aspirin and beta blockers. Diagnosis is usually based on the pattern of symptoms, response to therapy over time, and spirometry lung function testing. Asthma is classified according to the frequency of symptoms, forced expiratory, volume in one second (FEV1), and peak expiratory flow rate. It may also be classified as atopic or non-atopic, where atopy refers to a predisposition towards developing a type 1 hypersensitivity reaction.

In allergic asthma, inflammation of the airways is a key component resulting in airway remodeling and damage. Immunity mediated by T helper 2 cells and the cytokines produced by them, including IL-3, IL-4, IL-5, IL-9, IL-13, and GM-CSF, have been shown to play a major role in this disease (Holgate (2012) Nat. Riled, 18, 73-83).

Thymic stromallymphopoletin (TSLP) is a cytokine that is released by epithelial cells in response to proinflammatory stimuli. It signals through a heterodimeric receptor consisting of the IL-7Rα subunit and the unique TSLP receptor (West et al. (2012) Drug Discovery Today: Disease Mechanisms 9, e83-e88). The cytokine acts on a number of different immune cells, initiating inflammatory responses and differentiation of naïve T cells into TH2 cells expressing high levels of IL-4, IL-5 and IL-13, all involved in the pathogenesis of asthma.

There is no cure for asthma, therefore, there is a great need for therapeutic agents capable of ameliorating or eliminating the symptoms of respiratory disorders, such as asthma.

SUMMARY OF THE INVENTION

According to a first aspect of the invention, there is provided a peptide ligand specific for TSLP comprising a polypeptide comprising at least three cysteine residues, separated by at least two loop sequences, and a molecular scaffold which forms covalent bonds with the cysteine residues of the polypeptide such that at least two polypeptide loops are formed on the molecular scaffold.

According to a further aspect of the invention, there is provided a pharmaceutical composition comprising a peptide ligand as defined herein in combination with one or more pharmaceutically acceptable excipients.

According to a yet further aspect of the invention, there is provided a peptide ligand as defined herein for use in preventing, suppressing or treating a disease or disorder mediated by TSLP.

DETAILED DESCRIPTION OF THE INVENTION

Figure 1:
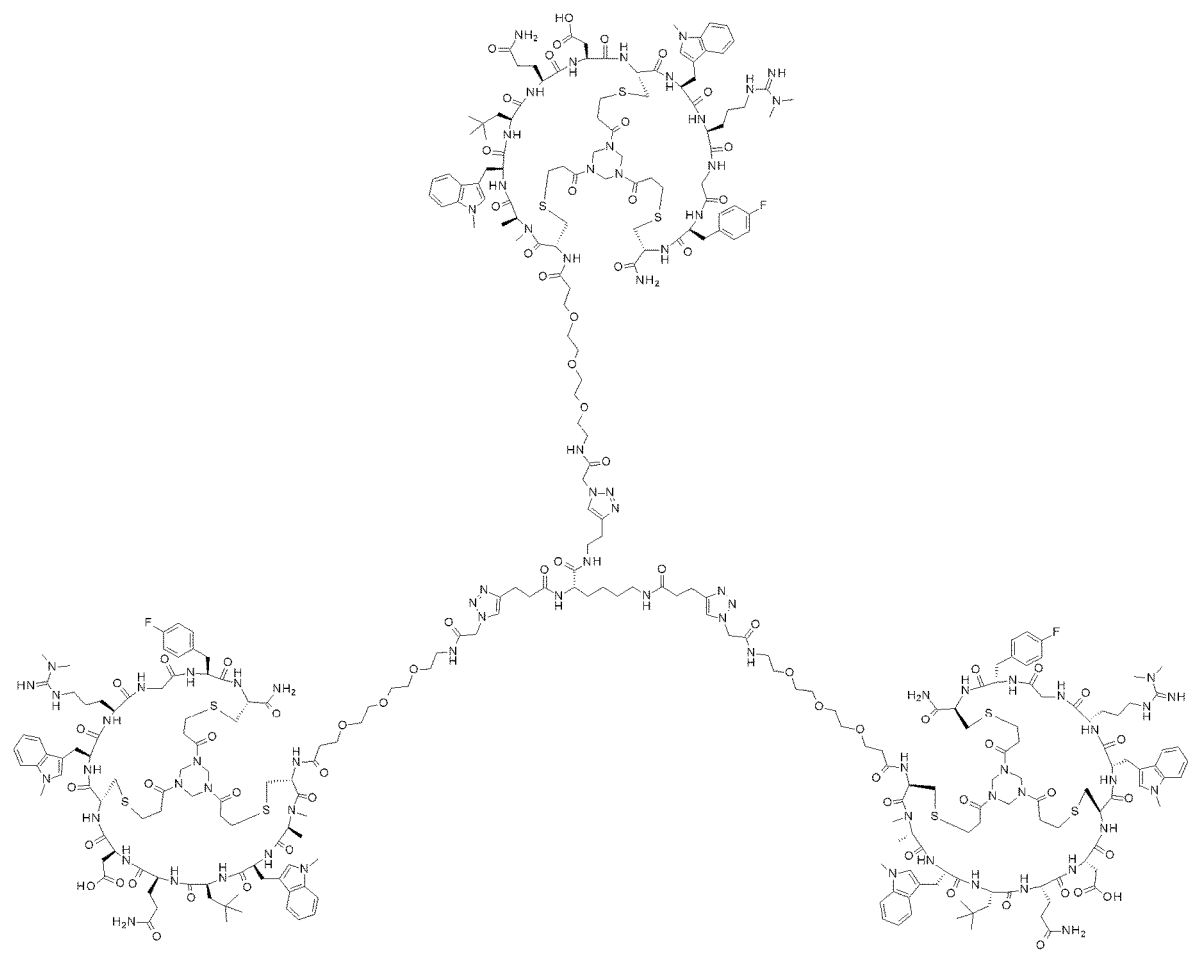
FIG. 1 depicts the structure of the title compound of Example 250.

According to a first aspect of the invention, there is provided a peptide ligand specific for TSLP comprising a polypeptide comprising at least three cysteine residues, separated by at least two loop sequences, and a molecular scaffold which forms covalent bonds with the cysteine residues of the polypeptide such that at least two polypeptide loops are formed on the molecular scaffold.

In one embodiment, said loop sequences comprise 3, 4, 5, 6 or 7 amino acid acids.

In a further embodiment, said peptide ligand comprises three cysteine residues separated by two loop sequences, the first of which consists of 5 amino acids and the second of which consists of 4 amino acids.

In one embodiment, said peptide ligand comprises three cysteine residues separated by two loop sequences, the first of which consists of 5 amino acids and the second of which consists of 4 amino acids and said peptide ligand comprises an amino acid sequence of:

(SEQ ID NO: 1)
CQ[TrpMe][tBuA]QDC[TrpMe][ADMA]G[4F3ClPhe]C;

(SEQ ID NO: 2)
CQ[TrpMe][tBuA]QDC[TrpMe]ADMA]G[4-FPhe]C;

(SEQ ID NO: 3)
CQ[TrpMe][tBuA]EDC[TrpMe][ADMA]G[4-FPhe]C;

(SEQ ID NO: 4)
CQW[tBuA]EDCWRG[4-FPhe]C;

(SEQ ID NO: 5)
C[AMe][TrpMe][tBuA]Q[MeD]C[TrpMe][ADMA]G[4-FPhe]C;

(SEQ ID NO: 6)
CQWLEDCWRG[4F3ClPhe]C;

-continued (SEQ ID NO: 7)
C[AMe][TrpMe][tBuA]QDC[TrpMe][LysMe3]G[4-FPhe]C;

(SEQ ID NO: 8)
CQWLQDCWRG[4-FPhe]C;

(SEQ ID NO: 9)
CQWLEDCWRG[3,4diClPhe]C;

(SEQ ID NO: 10)
C[AMe][TrpMe][tBuA]QDC[TrpMe][ChMeA]G[4-FPhe]C;

(SEQ ID NO: 11)
CQ[TrpMe]LEDC[TrpMe][ADMA]G[4-FPhe]C;

(SEQ ID NO: 12)
CQWLEDCWRG[4-ClPhe]C;

(SEQ ID NO: 13)
C[AMe][TrpMe][tBuA]QDC[TrpMe][ADMA]G[4-FPhe]C;

(SEQ ID NO: 14)
CQ[TrpMe]LEDC[TrpMe]RG[4-FPhe]C;

(SEQ ID NO: 15)
CQWLEDCWRG[4-FPhe]C;

(SEQ ID NO: 16)
C[AMe][TrpMe][tBuA]QDC[TrpMe][ADMA]G[4-FPhe]C;

(SEQ ID NO: 17)
CHWLEDCWRG[4-FPhe]C;

(SEQ ID NO: 18)
CQWLQDCW[ADMA]G[4-FPhe]C;

(SEQ ID NO: 19)
CQ[5FTrp]LEDC[5FTrp]RG[4-FPhe]C;

(SEQ ID NO: 20)
CQWLEDCWRG[3,4diFPhe]C;

(SEQ ID NO: 21)
CQWLENCWRG[4-FPhe]C;

(SEQ ID NO: 22)
C[AMe][TrpMe][tBuA]QDC[TrpMe][AcK]G[4-FPhe]C;

(SEQ ID NO: 23)
C[AMe][Nal1][tBuA]QDC[TrpMe][ADMA]G[4-FPhe]C;

(SEQ ID NO: 24)
CQWLEDCWRG[4-BrPhe]C;

(SEQ ID NO: 25)
CQ[Nal1]LEDCWRG[4-FPhe]C;

(SEQ ID NO: 26)
CWWLQDCW[ADMA]G[4-FPhe]C;

(SEQ ID NO: 27)
C[AMe]WLEDCW[ADMA]G[4-FPhe]C;

(SEQ ID NO: 28)
CQW[iPrMeA]EDCWRG[4-FPhe]C;

(SEQ ID NO: 29)
CQWLEDCWRG[3-ClPhe]C;

(SEQ ID NO: 30)
C[AMe][TrpMe][tBuA]QDC[TrpMe][NeopentA]G[4-FPhe]C;

(SEQ ID NO: 31)
C[AMe][TrpMe][tBuA]QDC[TrpMe][Cha]G[4-FPhe]C;

(SEQ ID NO: 32)
C[AMe][Nal1]LQDC[TrpMe][ADMA]G[4-FPhe]C;

(SEQ ID NO: 33)
CQWLEDCWRG[3,4,5triFPhe]C;

(SEQ ID NO: 34)
CQ[Nal1]LEDCW[ADMA]G[4-FPhe]C;

(SEQ ID NO: 35)
CQWLFDCWRG[4-FPhe]C;

(SEQ ID NO: 36)
C[AMe][TrpMe][tBuA]QDC[5FTrp]RG[4-FPhe]C;

(SEQ ID NO: 37)
CQWLEDCWRG[3-F,4-ClPhe]C;

(SEQ ID NO: 38)
CQWLEDCWRGFC;

(SEQ ID NO: 39)
CQW[tBuA]EDCWRGFC;

(SEQ ID NO: 40)
C[AMe][TrpMe][tBuA]QDC[TrpMe][BnA]G[4-FPhe]C;

(SEQ ID NO: 41)
CQWLEDCWRG[Nal1]C;

(SEQ ID NO: 42)
CQWLEDCWRG[Nal2]C;

(SEQ ID NO: 43)
CQWMEDCWRG[4-FPhe]C;

(SEQ ID NO: 44)
C[AMe][TrpMe][tBuA][Aib]DC[TrpMe][ADMA]G[4-FPhe]C;

(SEQ ID NO: 45)
CQWIEDCWRG[4-FPhe]C;

(SEQ ID NO: 46)
CQWLEDCWRG[3,5diF, 4ClPhe]C;

(SEQ ID NO: 47)
CQWLEDC[4-ClNal]RG[4-FPhe]C;

(SEQ ID NO: 48)
CA[Nal1]LEDCW[Harg]G[4-FPhe]C;

(SEQ ID NO: 49)
CTWLEDCWRGFC;

(SEQ ID NO: 50)
CQW[CpentA]EDCWRGFC;

(SEQ ID NO: 51)
CAWLEDC[Nal1]RG[4-FPhe]C;

(SEQ ID NO: 52)
CQWLEDCW[4-PipA]G[4-FPhe]C;

(SEQ ID NO: 53)
C[AMe][TrpMe][tBuA]QDC[TrpMe][ADMA]G[4-ClNal]C;

(SEQ ID NO: 54)
CVWLDDCWRGFC;

(SEQ ID NO: 55)
CQWLEDCWRG[3-MePhe]C;

(SEQ ID NO: 56)
CHWLEDCWRGFC;

(SEQ ID NO: 57)
CTWLDDCWRGFC;

(SEQ ID NO: 58)
CQWLEDCWRG[4-CF3Phe]C;

(SEQ ID NO: 59)
CQWLEDCWRa[4-FPhe]C;

(SEQ ID NO: 60)
CQW[CproA]EDCWRGFC;

CQWLEDCW[TriMeK]GFC; (SEQ ID NO: 61)

CQWLEDCW[ADMA]GFC; (SEQ ID NO: 62)

CQW[Cha]EDCWRGFC; (SEQ ID NO: 63)

CHWLENCWRGFC; (SEQ ID NO: 64)

CLWLDDCWRGFC; (SEQ ID NO: 65)

C[AMe][TrpMe][tBuA]QDC[TrpMe][ADMA]G[3AcNH4ClPhe]C; (SEQ ID NO: 66)

CTWLEDCWHGFC; (SEQ ID NO: 67)

CQW[Nva]EDCWRGFC; (SEQ ID NO: 68)

CQWLEDCWRG[3-FPhe]C; (SEQ ID NO: 69)

CQWLEDCWRG[4-MePhe]C; (SEQ ID NO: 70)

CQW[ChMeA]EDCWRGFC; (SEQ ID NO: 71)

CHWLDDCWRGFC; (SEQ ID NO: 72)

CDWLDDCWRGFC; (SEQ ID NO: 73)

CDWLEDCWRGFC; (SEQ ID NO: 74)

CEWLEDCWRGFC; (SEQ ID NO: 75)

CQWLEDCW[Cit]GFC; (SEQ ID NO: 76)

CQWL[3-ClPhe]DCWRG[4-FPhe]C; (SEQ ID NO: 77)

CAWLTDCWRGFC; (SEQ ID NO: 78)

CQWLEDC[7-OMeTrp]RG[4-FPhe]C; (SEQ ID NO: 79)

CQW[Nle]EDCWRGFC; (SEQ ID NO: 80)

CQWLEDCWRG[2-FPhe]C; (SEQ ID NO: 81)

CQW[TriFMeA]EDCWRGFC; (SEQ ID NO: 82)

CQWLEDCW[HArg]GFC; (SEQ ID NO: 83)

CQWLEDCWRG[Cha]C; (SEQ ID NO: 84)

CA[Nal1]LEDC[Nal1][HArg]G[4-FPhe]C; (SEQ ID NO: 85)

CRWLDDCWQGFC; (SEQ ID NO: 86)

CQWLQDCFRG[4-FPhe]C; (SEQ ID NO: 87)

CQWLEDCWRG[4-CNPhe]C; (SEQ ID NO: 88)

CNWLEDCWHGFC; (SEQ ID NO: 89)

C[dA]WLEDCWRG[4-FPhe]C; (SEQ ID NO: 90)

CQWLEDCWRG[3-CNPhe]C; (SEQ ID NO: 91)

CQWLEDCW[Can]GFC; (SEQ ID NO: 92)

CQWLEDCWRG[3-ThienylA]C; (SEQ ID NO: 93)

CQWLEDCW[Agb]GFC; (SEQ ID NO: 94)

C[dA]WLEDCW[ADMA]G[4-FPhe]C; (SEQ ID NO: 95)

CQWLEDCWRG[2ThienylA]C; (SEQ ID NO: 96)

CEWLEDCWKGFC; (SEQ ID NO: 97)

CFWLEDCWRGYC; (SEQ ID NO: 98)

CQWLEDCWRGWC; (SEQ ID NO: 99)

CDWLDDCWKGFC; (SEQ ID NO: 100)

CQWLEDCWRG[4-MeOPhe]C; (SEQ ID NO: 101)

CQWLEDCWRG[3-BrPhe]C; (SEQ ID NO: 102)

CWWL[3-ClPhe]DCWRG[4-FPhe]C; (SEQ ID NO: 103)

CQ[ButG]LEDCW[ButG]G[4-FPhe]C; (SEQ ID NO: 104)

CQWLEDCWRG[2PyrA]C; (SEQ ID NO: 105)

CQW[M(O)]EDCWRGFC; (SEQ ID NO: 106)

CQWLEDCWRG[BnA]C; (SEQ ID NO: 107)

CQWLEDCWAGFC; (SEQ ID NO: 108)

CTILEDCWMGFC; (SEQ ID NO: 109)

CQW[Abu]EDCWRGFC; (SEQ ID NO: 110)

CHWLENCWAGFC; (SEQ ID NO: 111)

CQWLEDCWRG[PentFPhe]C; (SEQ ID NO: 112)

CQW[LMe]EDCWRG[4-FPhe]C; (SEQ ID NO: 113)

-continued

CQWLEDCW[Dap]GFC; (SEQ ID NO: 114)

CQWLEDCWRG[4-PyrA]C; (SEQ ID NO: 115)

CQWLEDCWRG[3-PyrA]C; (SEQ ID NO: 116)

CHWLENCW[Dap]GFC; (SEQ ID NO: 117)
and

CQW[4-MenL]EDCWRG[4-FPhe]C; (SEQ ID NO: 118)

or a pharmaceutically acceptable salt thereof.

In a further embodiment, said peptide ligand comprises three cysteine residues separated by two loop sequences, the first of which consists of 5 amino acids and the second of which consists of 4 amino acids and said peptide ligand optionally comprises N- and/or C-terminal modifications and is selected from:

Ac-(SEQ ID NO: 1) (hereinafter referred to as Example 1);
Ac-(SEQ ID NO: 2) (hereinafter referred to as Example 2);
Ac-(SEQ ID NO: 3) (hereinafter referred to as Example 3);
tertBuCO-(SEQ ID NO: 3) (hereinafter referred to as Example 6);
R$^1$-(SEQ ID NO: 3) (hereinafter referred to as Example 7);
Ac-(SEQ ID NO: 4) (hereinafter referred to as Example 4);
Ac-(SEQ ID NO: 5) (hereinafter referred to as Example 5);
Ac-(SEQ ID NO: 6) (hereinafter referred to as Example 8);
Ac-(SEQ ID NO: 7) (hereinafter referred to as Example 9);
Ac-(SEQ ID NO: 8) (hereinafter referred to as Example 10);
Ac-(SEQ ID NO: 9) (hereinafter referred to as Example 11);
Ac-(SEQ ID NO: 10) (hereinafter referred to as Example 12);
Ac-(SEQ ID NO: 11) (hereinafter referred to as Example 13);
Ac-(SEQ ID NO: 12) (hereinafter referred to as Example 14);
Octanoyl-(SEQ ID NO: 13) (hereinafter referred to as Example 15);
Ac-(SEQ ID NO: 14) (hereinafter referred to as Example 16);
Ac-(SEQ ID NO: 15) (hereinafter referred to as Example 17);
Ac-(SEQ ID NO: 15)-[dA] (hereinafter referred to as Example 33);
(SEQ ID NO: 15)-COOH (hereinafter referred to as Example 48);
Ac-(SEQ ID NO: 16) (hereinafter referred to as Example 18);
Ac-(SEQ ID NO: 17) (hereinafter referred to as Example 19);
Ac-(SEQ ID NO: 18) (hereinafter referred to as Example 20);
Ac-(SEQ ID NO: 19) (hereinafter referred to as Example 21);
Ac-(SEQ ID NO: 20) (hereinafter referred to as Example 22);
Ac-(SEQ ID NO: 21) (hereinafter referred to as Example 23);
Ac-(SEQ ID NO: 22) (hereinafter referred to as Example 24);
(SEQ ID NO: 23) (hereinafter referred to as Example 252);
Ac-(SEQ ID NO: 23) (hereinafter referred to as Example 25);
Ac-(SEQ ID NO: 23)-[dA] (hereinafter referred to as Example 29);
Ac-(SEQ ID NO: 24) (hereinafter referred to as Example 26);
Ac-(SEQ ID NO: 25) (hereinafter referred to as Example 27);
Ac-(SEQ ID NO: 26) (hereinafter referred to as Example 28);
Ac-(SEQ ID NO: 27) (hereinafter referred to as Example 30);
Ac-(SEQ ID NO: 28) (hereinafter referred to as Example 31);
Ac-(SEQ ID NO: 29) (hereinafter referred to as Example 32);
Ac-(SEQ ID NO: 30) (hereinafter referred to as Example 34);
Ac-(SEQ ID NO: 31) (hereinafter referred to as Example 35);
Ac-(SEQ ID NO: 32) (hereinafter referred to as Example 36);
Ac-(SEQ ID NO: 33) (hereinafter referred to as Example 37);
Ac-(SEQ ID NO: 34) (hereinafter referred to as Example 38);
Ac-(SEQ ID NO: 34)-[dA] (hereinafter referred to as Example 49);
Ac-(SEQ ID NO: 34)-COOH (hereinafter referred to as Example 69);
Ac-(SEQ ID NO: 35) (hereinafter referred to as Example 43);
Ac-(SEQ ID NO: 35)-COOH (hereinafter referred to as Example 39);
Ac-(SEQ ID NO: 36) (hereinafter referred to as Example 40);
Ac-(SEQ ID NO: 37) (hereinafter referred to as Example 41);
A-(SEQ ID NO: 38)-ADGDML (hereinafter referred to as Example 42);
GTDSAE-(SEQ ID NO: 38)-A (hereinafter referred to as Example 45);
Ac-A-(SEQ ID NO: 38)-PLD (hereinafter referred to as Example 53);
Ac-(SEQ ID NO: 38)-APDERD (hereinafter referred to as Example 54);
A-(SEQ ID NO: 38)-DDAHAP (hereinafter referred to as Example 55);
TMEYRD-(SEQ ID NO: 38)-A (hereinafter referred to as Example 56);
A-(SEQ ID NO: 38)-SSSDQS (hereinafter referred to as Example 59);
SDEQRT-(SEQ ID NO: 38)-A (hereinafter referred to as Example 61);
DDEIMQ-(SEQ ID NO: 38)-A (hereinafter referred to as Example 64);

RTDETG-(SEQ ID NO: 38)-A (hereinafter referred to as Example 67);
A-(SEQ ID NO: 38)-A (hereinafter referred to as Example 68);
ETNNLE-(SEQ ID NO: 38)-A (hereinafter referred to as Example 71);
Ac-(SEQ ID NO: 38) (hereinafter referred to as Example 79);
DPPKPR-(SEQ ID NO: 38)-A (hereinafter referred to as Example 87);
(SEQ ID NO: 38)-DTSTHS (hereinafter referred to as Example 128);
Ac-(SEQ ID NO: 39) (hereinafter referred to as Example 44);
Ac-(SEQ ID NO: 40) (hereinafter referred to as Example 46);
Ac-(SEQ ID NO: 41) (hereinafter referred to as Example 47);
Ac-(SEQ ID NO: 42) (hereinafter referred to as Example 50);
Ac-(SEQ ID NO: 43) (hereinafter referred to as Example 51);
Ac-(SEQ ID NO: 44) (hereinafter referred to as Example 52);
Ac-(SEQ ID NO: 45) (hereinafter referred to as Example 57);
Ac-(SEQ ID NO: 46) (hereinafter referred to as Example 58);
Ac-(SEQ ID NO: 47) (hereinafter referred to as Example 60);
Ac-(SEQ ID NO: 48) (hereinafter referred to as Example 62);
A-(SEQ ID NO: 49)-ADS (hereinafter referred to as Example 63);
Ac-(SEQ ID NO: 50) (hereinafter referred to as Example 65);
Ac-(SEQ ID NO: 51) (hereinafter referred to as Example 66);
Ac-(SEQ ID NO: 52) (hereinafter referred to as Example 70);
Ac-(SEQ ID NO: 53) (hereinafter referred to as Example 72);
SPP-(SEQ ID NO: 54)-A (hereinafter referred to as Example 73);
Ac-(SEQ ID NO: 55) (hereinafter referred to as Example 74);
A-(SEQ ID NO: 56)-HLE (hereinafter referred to as Example 75);
A-(SEQ ID NO: 57)-A (hereinafter referred to as Example 76);
Ac-(SEQ ID NO: 58) (hereinafter referred to as Example 77);
Ac-(SEQ ID NO: 59) (hereinafter referred to as Example 78);
Ac-(SEQ ID NO: 60) (hereinafter referred to as Example 80);
Ac-(SEQ ID NO: 61) (hereinafter referred to as Example 81);
Ac-(SEQ ID NO: 62) (hereinafter referred to as Example 82);
Ac-(SEQ ID NO: 63) (hereinafter referred to as Example 83);
tertBuCO-(SEQ ID NO: 64) (hereinafter referred to as Example 84);
$R^1$-(SEQ ID NO: 64) (hereinafter referred to as Example 89);
$R^2$-(SEQ ID NO: 64) (hereinafter referred to as Example 95);
Benzyl-(SEQ ID NO: 64) (hereinafter referred to as Example 93);
Ac-(SEQ ID NO: 64)-[N-phenethylamide] (hereinafter referred to as Example 96);
$R^3$-(SEQ ID NO: 64) (hereinafter referred to as Example 99);
$R^4$-(SEQ ID NO: 64) (hereinafter referred to as Example 103);
Ac-(SEQ ID NO: 64)-[N-benzylamide] (hereinafter referred to as Example 109);
A-(SEQ ID NO: 64)-A (hereinafter referred to as Example 115);
Benzoyl-(SEQ ID NO: 64) (hereinafter referred to as Example 116);
Ac-(SEQ ID NO: 64)-$R^5$ (hereinafter referred to as Example 120);
Succinyl-(SEQ ID NO: 64) (hereinafter referred to as Example 121);
Ac-(SEQ ID NO: 64)-[N-octylamide] (hereinafter referred to as Example 122);
Ac-(SEQ ID NO: 64)-[N-pentylamide] (hereinafter referred to as Example 123);
Ac-(SEQ ID NO: 64) (hereinafter referred to as Example 124);
Ac-(SEQ ID NO: 64)-$R^6$ (hereinafter referred to as Example 127);
(SEQ ID NO: 64) (hereinafter referred to as Example 129);
Decanoyl-(SEQ ID NO: 64) (hereinafter referred to as Example 137);
Hexanoyl-(SEQ ID NO: 64) (hereinafter referred to as Example 139);
SPT-(SEQ ID NO: 65)-A (hereinafter referred to as Example 85);
Ac-(SEQ ID NO: 66) (hereinafter referred to as Example 86);
TIK-(SEQ ID NO: 67)-A (hereinafter referred to as Example 88);
Ac-(SEQ ID NO: 68) (hereinafter referred to as Example 90);
Ac-(SEQ ID NO: 69) (hereinafter referred to as Example 91);
Ac-(SEQ ID NO: 70) (hereinafter referred to as Example 92);
Ac-(SEQ ID NO: 71) (hereinafter referred to as Example 94);
DNH-(SEQ ID NO: 72)-A (hereinafter referred to as Example 97);
HPN-(SEQ ID NO: 73)-A (hereinafter referred to as Example 98);
Ac-(SEQ ID NO: 74)-TTS (hereinafter referred to as Example 100);
A-(SEQ ID NO: 75)-A (hereinafter referred to as Example 101);
(SEQ ID NO: 76) (hereinafter referred to as Example 102);
Ac-(SEQ ID NO: 76) (hereinafter referred to as Example 104);
Ac-(SEQ ID NO: 77) (hereinafter referred to as Example 105);
DQD-(SEQ ID NO: 78)-A (hereinafter referred to as Example 106);
Ac-(SEQ ID NO: 79) (hereinafter referred to as Example 107);

Ac-(SEQ ID NO: 80) (hereinafter referred to as Example 108);
Ac-(SEQ ID NO: 81) (hereinafter referred to as Example 110);
Ac-(SEQ ID NO: 82) (hereinafter referred to as Example 111);
Ac-(SEQ ID NO: 83) (hereinafter referred to as Example 112);
Ac-(SEQ ID NO: 84) (hereinafter referred to as Example 113);
Ac-(SEQ ID NO: 85) (hereinafter referred to as Example 114);
REN-(SEQ ID NO: 86)-A (hereinafter referred to as Example 117);
Ac-(SEQ ID NO: 87) (hereinafter referred to as Example 118);
Ac-(SEQ ID NO: 88) (hereinafter referred to as Example 119);
A-(SEQ ID NO: 89)-HEE (hereinafter referred to as Example 125);
Ac-(SEQ ID NO: 90) (hereinafter referred to as Example 126);
Ac-(SEQ ID NO: 91) (hereinafter referred to as Example 130);
Ac-(SEQ ID NO: 92) (hereinafter referred to as Example 131);
Ac-(SEQ ID NO: 93) (hereinafter referred to as Example 132);
Ac-(SEQ ID NO: 94) (hereinafter referred to as Example 133);
Ac-(SEQ ID NO: 95) (hereinafter referred to as Example 134);
Ac-(SEQ ID NO: 96) (hereinafter referred to as Example 135);
A-(SEQ ID NO: 97)-HSE (hereinafter referred to as Example 136);
A-(SEQ ID NO: 98)-ETA (hereinafter referred to as Example 138);
Ac-(SEQ ID NO: 99) (hereinafter referred to as Example 140);
A-(SEQ ID NO: 100)-A (hereinafter referred to as Example 141);
Ac-(SEQ ID NO: 101) (hereinafter referred to as Example 142);
Ac-(SEQ ID NO: 102) (hereinafter referred to as Example 143);
Ac-(SEQ ID NO: 103) (hereinafter referred to as Example 144);
Ac-(SEQ ID NO: 104) (hereinafter referred to as Example 145);
Ac-(SEQ ID NO: 105) (hereinafter referred to as Example 146);
Ac-(SEQ ID NO: 106) (hereinafter referred to as Example 147);
Ac-(SEQ ID NO: 107) (hereinafter referred to as Example 148);
Ac-(SEQ ID NO: 108) (hereinafter referred to as Example 149);
A-(SEQ ID NO: 109)-A (hereinafter referred to as Example 150);
Ac-(SEQ ID NO: 110) (hereinafter referred to as Example 151);
Ac-(SEQ ID NO: 111) (hereinafter referred to as Example 152);
Ac-(SEQ ID NO: 112) (hereinafter referred to as Example 153);
Ac-(SEQ ID NO: 113) (hereinafter referred to as Example 154);
Ac-(SEQ ID NO: 114) (hereinafter referred to as Example 155);
(SEQ ID NO: 114) (hereinafter referred to as Example 156);
Ac-(SEQ ID NO: 115) (hereinafter referred to as Example 157);
Ac-(SEQ ID NO: 116) (hereinafter referred to as Example 158);
Ac-(SEQ ID NO: 117) (hereinafter referred to as Example 159); and
Ac-(SEQ ID NO: 118) (hereinafter referred to as Example 160);

wherein Ac represents acetyl, tertBuCO represents

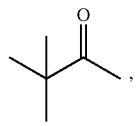

$R^1$ represents:

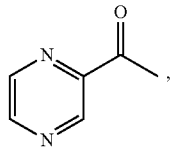

$R^2$ represents:

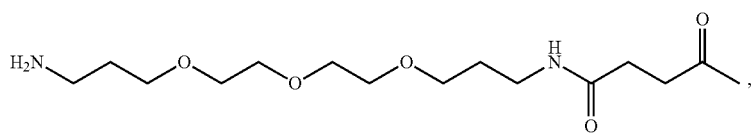 [SMILES: CC(=O)CCC(=O)NCCCOCCOCCOCCCN]

$R^3$ represents:

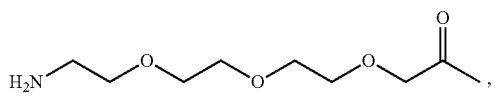

R⁴ represents:

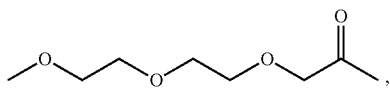

R⁵ represents:

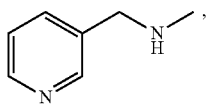

and

R⁶ represents:

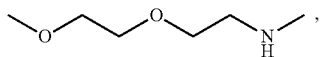

or a pharmaceutically acceptable salt thereof.

In a further embodiment, said peptide ligand comprises three cysteine residues separated by two loop sequences, the first of which consists of 7 amino acids and the second of which consists of 5 amino acids.

In one embodiment, said peptide ligand comprises three cysteine residues separated by two loop sequences, the first of which consists of 7 amino acids and the second of which consists of 5 amino acids and said peptide ligand comprises an amino acid sequence of:

CESLDPWSCPVWWRC; (SEQ ID NO: 119)

CPSLDPWTCQSWYEC; (SEQ ID NO: 120)

CTELDPWTCETWWLC; (SEQ ID NO: 121)

CRDLDPWTCSSWWLC; (SEQ ID NO: 122)

CADLDPWTCPNWWLC; (SEQ ID NO: 123)

CVDLDPWTCEQWWLC; (SEQ ID NO: 124)

CKDLDPWTCSSWWEC; (SEQ ID NO: 125)

CRDLDPWTCPTWWTC; (SEQ ID NO: 126)

CTDLDPWTCNSWWLC; (SEQ ID NO: 127)

CRDLDPWTCEEWWLC; (SEQ ID NO: 128)

CRELDPWTCETWWLC; (SEQ ID NO: 129)

CKELDPWTCETWWLC; (SEQ ID NO: 130)

C[Orn]ELDPWTCETWWLC; (SEQ ID NO: 131)

CQELDPWTCETWWLC; (SEQ ID NO: 132)

CTELD[diF-P]WTCETWWLC; (SEQ ID NO: 133)

CVDLDPWSCEDWWLC; (SEQ ID NO: 134)

CPDLDPWTCPLWWTC; (SEQ ID NO: 135)

CPDLDPWTCSDWWLC; (SEQ ID NO: 136)

CRDLDPWTCDSWWLC; (SEQ ID NO: 137)

CTDLDPWTCPDWWLC; (SEQ ID NO: 138)

CTELD[5-Ph-P]WTCETWWLC; (SEQ ID NO: 139)
and

CTELD[Chx-P]WTCETWWLC; (SEQ ID NO: 140)

or a pharmaceutically acceptable salt thereof.

In a further embodiment, said peptide ligand comprises three cysteine residues separated by two loop sequences, the first of which consists of 7 amino acids and the second of which consists of 5 amino acids and said peptide ligand optionally comprises N- and/or C-terminal modifications and is selected from:

A-(SEQ ID NO: 119)-A (hereinafter referred to as Example 161);

A-(SEQ ID NO: 120)-A (hereinafter referred to as Example 162);

A-(SEQ ID NO: 121)-A (hereinafter referred to as Example 163);

(SEQ ID NO: 121) (hereinafter referred to as Example 185);

A-(SEQ ID NO: 122)-A (hereinafter referred to as Example 164);

YATTQV-(SEQ ID NO: 122)-A (hereinafter referred to as Example 171);

KDNRVD-(SEQ ID NO: 122)-A (hereinafter referred to as Example 172);

EYQRDV-(SEQ ID NO: 122)-A (hereinafter referred to as Example 173);

A-(SEQ ID NO: 122)-SNSYDMA (hereinafter referred to as Example 174);

A-(SEQ ID NO: 122)-SESVHTA (hereinafter referred to as Example 175);

A-(SEQ ID NO: 122)-SSDTTDA (hereinafter referred to as Example 176);

A-(SEQ ID NO: 122)-KPDHVDA (hereinafter referred to as Example 177);

A-(SEQ ID NO: 122)-ANV (hereinafter referred to as Example 186);

RVNTHQ-(SEQ ID NO: 122)-A (hereinafter referred to as Example 190);

YDRDFT-(SEQ ID NO: 122)-A (hereinafter referred to as Example 191);

EVDTYP-(SEQ ID NO: 122)-A (hereinafter referred to as Example 192);

A-(SEQ ID NO: 122)-ADGLYDA (hereinafter referred to as Example 193);
AHP-(SEQ ID NO: 123)-A (hereinafter referred to as Example 165);
YGA-(SEQ ID NO: 124)-A (hereinafter referred to as Example 166);
A-(SEQ ID NO: 125)-APN (hereinafter referred to as Example 167);
A-(SEQ ID NO: 126)-YDE (hereinafter referred to as Example 168);
A-(SEQ ID NO: 127)-AGD (hereinafter referred to as Example 169);
A-(SEQ ID NO: 128)-AHP (hereinafter referred to as Example 170);
(SEQ ID NO: 129) (hereinafter referred to as Example 178);
(SEQ ID NO: 130) (hereinafter referred to as Example 179);
(SEQ ID NO: 131) (hereinafter referred to as Example 180);
(SEQ ID NO: 132) (hereinafter referred to as Example 181);
(SEQ ID NO: 133) (hereinafter referred to as Example 182);
A-(SEQ ID NO: 134)-A (hereinafter referred to as Example 183);
A-(SEQ ID NO: 135)-A (hereinafter referred to as Example 184);
RAP-(SEQ ID NO: 136)-A (hereinafter referred to as Example 187);
SHV-(SEQ ID NO: 137)-A (hereinafter referred to as Example 188);
RDL-(SEQ ID NO: 138)-A (hereinafter referred to as Example 189);
(SEQ ID NO: 139) (hereinafter referred to as Example 194); and
(SEQ ID NO: 140) (hereinafter referred to as Example 195);

or a pharmaceutically acceptable salt thereof.

In a further embodiment, said peptide ligand comprises three cysteine residues separated by two loop sequences, the first of which consists of 7 amino acids and the second of which consists of 3 amino acids.

In one embodiment, said peptide ligand comprises three cysteine residues separated by two loop sequences, the first of which consists of 7 amino acids and the second of which consists of 3 amino acids and said peptide ligand comprises an amino acid sequence of:

```
                              (SEQ ID NO: 141)
CDWQWSYDCWLPC;

(SEQ ID NO: 142)
CDWVWEYDCWLPC;

(SEQ ID NO: 143)
CDWDWEYDCWLHC;

(SEQ ID NO: 144)
CDWHWEYDCWLSC;

(SEQ ID NO: 145)
CTWNWEYDCWLDC;

(SEQ ID NO: 146)
CEWNWAYDCWLGC;

(SEQ ID NO: 147)
CEWNWEYDCWLDC;

(SEQ ID NO: 148)
CQWNWTYDCWLGC;

(SEQ ID NO: 149)
CKWMWEYDCWLSC;

(SEQ ID NO: 150)
CDWQWEYDCWLSC;

(SEQ ID NO: 151)
CDWNWTYDCWLDC;

(SEQ ID NO: 152)
CDWNWSYDCWLPC;

(SEQ ID NO: 153)
CDWDWDYDCWLPC;

(SEQ ID NO: 154)
CVWHWEYDCWLDC;
and
                              (SEQ ID NO: 155)
CIWDWKYDCWLGC;
``` or a pharmaceutically acceptable salt thereof.

In a further embodiment, said peptide ligand comprises three cysteine residues separated by two loop sequences, the first of which consists of 7 amino acids and the second of which consists of 3 amino acids and said peptide ligand optionally comprises N- and/or C-terminal modifications and is selected from:
A-(SEQ ID NO: 141)-A (hereinafter referred to as Example 196);
A-(SEQ ID NO: 142)-A (hereinafter referred to as Example 197);
A-(SEQ ID NO: 143)-A (hereinafter referred to as Example 198);
A-(SEQ ID NO: 144)-A (hereinafter referred to as Example 199);
DEQHHE-(SEQ ID NO: 144)-A (hereinafter referred to as Example 209);
SNATKQ-(SEQ ID NO: 144)-A (hereinafter referred to as Example 210);
GNIKKS-(SEQ ID NO: 144)-A (hereinafter referred to as Example 211);
A-(SEQ ID NO: 144)-DPSSKQA (hereinafter referred to as Example 212);
A-(SEQ ID NO: 144)-YDNEMSA (hereinafter referred to as Example 213);
SEAQET-(SEQ ID NO: 144) (hereinafter referred to as Example 214);
SPTEPP-(SEQ ID NO: 144) (hereinafter referred to as Example 215);
(SEQ ID NO: 144)-EPETGQ (hereinafter referred to as Example 216);
NRSPSE-(SEQ ID NO: 144) (hereinafter referred to as Example 217);
Ac-(SEQ ID NO: 144) (hereinafter referred to as Example 218);
$R^7$-(SEQ ID NO: 144) (hereinafter referred to as Example 219);
A-(SEQ ID NO: 144)-EPETGQA (hereinafter referred to as Example 221);
(SEQ ID NO: 144)-GDMSVS (hereinafter referred to as Example 222);
(SEQ ID NO: 144)-YDNEMS (hereinafter referred to as Example 223);
(SEQ ID NO: 144)-APDHLP (hereinafter referred to as Example 224);

(SEQ ID NO: 144)-DPSSKQ (hereinafter referred to as Example 226);
(SEQ ID NO: 144)-ANSEFE (hereinafter referred to as Example 227);
(SEQ ID NO: 144)-GAGESS (hereinafter referred to as Example 228);
DHD-(SEQ ID NO: 145)-A (hereinafter referred to as Example 200);
ADG-(SEQ ID NO: 146)-A (hereinafter referred to as Example 201);
TLP-(SEQ ID NO: 147)-A (hereinafter referred to as Example 202);
SQE-(SEQ ID NO: 148)-A (hereinafter referred to as Example 203);
AET-(SEQ ID NO: 149)-A (hereinafter referred to as Example 204);
A-(SEQ ID NO: 150)-DPN (hereinafter referred to as Example 205);
A-(SEQ ID NO: 151)-API (hereinafter referred to as Example 206);
A-(SEQ ID NO: 152)-ANT (hereinafter referred to as Example 207);
A-(SEQ ID NO: 153)-FAE (hereinafter referred to as Example 208);
AND-(SEQ ID NO: 154)-A (hereinafter referred to as Example 220); and
ERN-(SEQ ID NO: 155)-A (hereinafter referred to as Example 225);
wherein $R^7$ represents

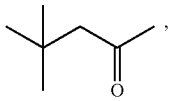

or a pharmaceutically acceptable salt thereof.

In a further embodiment, said peptide ligand comprises three cysteine residues separated by two loop sequences, the first of which consists of 6 amino acids and the second of which consists of 5 amino acids.

In one embodiment, said peptide ligand comprises three cysteine residues separated by two loop sequences, the first of which consists of 6 amino acids and the second of which consists of 5 amino acids and said peptide ligand comprises an amino acid sequence of:

```
                                      (SEQ ID NO: 156)
CSLDPWSCHNWWTC;
and (SEQ ID NO: 157)
CALDPWVCPQWWDC;
``` or a pharmaceutically acceptable salt thereof.

In a further embodiment, said peptide ligand comprises three cysteine residues separated by two loop sequences, the first of which consists of 6 amino acids and the second of which consists of 5 amino acids and said peptide ligand optionally comprises N- and/or C-terminal modifications and is selected from:
A-(SEQ ID NO: 156)-A (hereinafter referred to as Example 229); and
A-(SEQ ID NO: 157)-A (hereinafter referred to as Example 230);
or a pharmaceutically acceptable salt thereof.

In a further embodiment, said peptide ligand comprises three cysteine residues separated by two loop sequences, the first of which consists of 6 amino acids and the second of which consists of 6 amino acids.

In one embodiment, said peptide ligand comprises three cysteine residues separated by two loop sequences, the first of which consists of 6 amino acids and the second of which consists of 6 amino acids and said peptide ligand comprises an amino acid sequence of:

```
                                      (SEQ ID NO: 158)
CQEHDWYCLLYQPEC;
and (SEQ ID NO: 159)
CDELDIPCWIFKTLC;
``` or a pharmaceutically acceptable salt thereof.

In a further embodiment, said peptide ligand comprises three cysteine residues separated by two loop sequences, the first of which consists of 6 amino acids and the second of which consists of 6 amino acids and said peptide ligand optionally comprises N- and/or C-terminal modifications and is selected from:
A-(SEQ ID NO: 158)-A (hereinafter referred to as Example 231); and
A-(SEQ ID NO: 159)-A (hereinafter referred to as Example 232);
or a pharmaceutically acceptable salt thereof.

In one embodiment, the peptide ligand comprises an additional loop formed by the linking of two modified amino acid residues. In a further embodiment, the two modified amino acid residues are modified glycine residues (referred to herein as modG) separated by a linker moiety.

In one embodiment, the linker comprises a —(CH$_2$)$_{2-10}$— linker (such as a —(CH$_2$)$_{3-9}$— linker) optionally incorporating a double bond or a triazinyl ring (such as a 1,2,3 triazinyl ring).

Specific examples of the linker between said two modG residues include:
—CH$_2$—CH$_2$—CH$_2$—CH=CH—CH$_2$—CH$_2$—CH$_2$—CH$_2$—;
—CH$_2$—CH$_2$—CH$_2$—CH=CH—CH$_2$—CH$_2$—;
—CH$_2$—CH$_2$—CH$_2$—CH=CH—CH$_2$—CH$_2$—;
—CH$_2$—CH$_2$—CH$_2$—CH=CH—CH$_2$—CH$_2$—;
—CH$_2$—CH$_2$—CH$_2$=CH—CH—CH$_2$—CH$_2$—;
—CH$_2$—CH$_2$—CH$_2$—CH=CH—CH$_2$—CH$_2$—CH$_2$—;
—CH$_2$—CH$_2$—CH$_2$=CH—CH—CH$_2$—;
—CH$_2$—CH=CH—;
—CH$_2$—CH=CH—; and

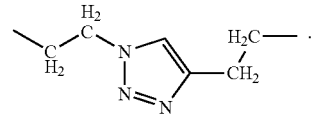

Suitable examples of the peptide ligands comprising the additional loop include:

```
                                      (SEQ ID NO: 160)
CQ[modG]LEDCW[modG]G[4-FPhe]C;

(SEQ ID NO: 161)
CQ[modG][tBuA]EDC[TrpMe][modG]G[4-FPhe]C;
```

-continued (SEQ ID NO: 162)
CQ[modG][tBuA]QDC[TrpMe][modG]G[4-FPhe]C;
and (SEQ ID NO: 163)
C[NMeA][modG][tBuA]QDC[TrpMe][modG]G[4-FPhe]C;

or a pharmaceutically acceptable salt thereof.

Specific examples of said additional loop containing peptide ligands include Examples 233 to 249.

In one embodiment, said peptide ligand comprises a multimeric binding complex which comprises at least two (such as three) bicyclic peptide ligands, wherein said peptide ligands may be the same or different, each of which comprises a polypeptide comprising at least three reactive groups, separated by at least two loop sequences, and a molecular scaffold which forms covalent bonds with the reactive groups of the polypeptide such that at least two polypeptide loops are formed on the molecular scaffold.

In a further embodiment, the multimeric binding complex comprises a trimeric moiety (i.e. three bicyclic peptides). In a further embodiment, the multimeric binding complex comprises a trimeric moiety (i.e. three identical bicyclic peptides). In a yet further embodiment, the peptide ligand comprises a trimeric moiety selected from Examples 250 and 251.

Unless defined otherwise, all technical and scientific terms used herein have the same meaning as commonly understood by those of ordinary skill in the art, such as in the arts of peptide chemistry, cell culture and phage display, nucleic acid chemistry and biochemistry. Standard techniques are used for molecular biology, genetic and biochemical methods (see Sambrook et al., Molecular Cloning: A Laboratory Manual, 3rd ed., 2001, Cold Spring Harbor Laboratory Press, Cold Spring Harbor, N.Y.; Ausubel et al., Short Protocols in Molecular Biology (1999) 4$^{th}$ ed., John Wiley & Sons, Inc.), which are incorporated herein by reference.

Nomenclature

Numbering

When referring to amino acid residue positions within the peptides of the invention, reactive groups (e.g. cysteine residues) are omitted from the numbering as they are invariant, therefore, the numbering of amino acid residues within the peptides of the invention is referred to as below:

(SEQ ID NO: 1)
-C-Q$_1$-TrpMe$_2$-tBuA$_3$-Q$_4$-D$_5$-C-TrpMe$_6$-ADMA$_7$-G$_8$-

4F3ClPhe$_9$-C-.

For the purpose of this description, all bicyclic peptides are assumed to be cyclised with 1,1',1"-(1,3,5-triazinane-1, 3,5-triyl)triprop-2-en-1-one (TATA) and yielding a tri-substituted structure. Cyclisation with TATA occurs on each of the three cysteine residues.

Molecular Format

N- or C-terminal extensions to the bicycle core sequence are added to the left or right side of the sequence, separated by a hyphen. For example, an N-terminal βAla-Sar10-Ala tail would be denoted as:

(SEQ ID NO: X)
βAla-Sar10-A-.

Inversed Peptide Sequences

In light of the disclosure in Nair et al (2003) J Immunol 170(3), 1362-1373, it is envisaged that the peptide sequences disclosed herein would also find utility in their retro-inverso form. For example, the sequence is reversed (i.e. N-terminus becomes C-terminus and vice versa) and their stereochemistry is likewise also reversed (i.e. D-amino acids become L-amino acids and vice versa).

Peptide Ligands

A peptide ligand, as referred to herein, refers to a peptide covalently bound to a molecular scaffold. Typically, such peptides comprise two or more reactive groups (i.e. cysteine residues) which are capable of forming covalent bonds to the scaffold, and a sequence subtended between said reactive groups which is referred to as the loop sequence, since it forms a loop when the peptide is bound to the scaffold. In the present case, the peptides comprise at least three cysteine residues, and form at least two loops on the scaffold.

Advantages of the Peptide Ligands

Certain bicyclic peptides of the present invention have a number of advantageous properties which enable them to be considered as suitable drug-like molecules for injection, inhalation, nasal, ocular, oral or topical administration. Such advantageous properties include:

Species cross-reactivity. This is a typical requirement for preclinical pharmacodynamics and pharmacokinetic evaluation;

Protease stability. Bicyclic peptide ligands should ideally demonstrate stability to plasma proteases, epithelial ("membrane-anchored") proteases, gastric and intestinal proteases, lung surface proteases, intracellular proteases and the like. Protease stability should be maintained between different species such that a bicycle lead candidate can be developed in animal models as well as administered with confidence to humans;

Desirable solubility profile. This is a function of the proportion of charged and hydrophilic versus hydrophobic residues and intra/inter-molecular H-bonding, which is important for formulation and absorption purposes; and An optimal plasma half-life in the circulation. Depending upon the clinical indication and treatment regimen, it may be required to develop a bicyclic peptide for short exposure in an acute illness management setting, or develop a bicyclic peptide with enhanced retention in the circulation, and is therefore optimal for the management of more chronic disease states. Other factors driving the desirable plasma half-life are requirements of sustained exposure for maximal therapeutic efficiency versus the accompanying toxicology due to sustained exposure of the agent.

Selectivity. Certain peptide ligands of the invention demonstrate good selectivity over other cytokines.

Pharmaceutically Acceptable Salts

It will be appreciated that salt forms are within the scope of this invention, and references to peptide ligands include the salt forms of said ligands.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, sulfuric, methanesulfonic (mesylate), ethanesulfonic, naphthalenesulfonic, valeric, propanoic, butanoic, malonic, glucuronic and lactobionic acids. One particular salt is the hydrochloride salt. Another particular salt is the acetate salt.

If the compound is anionic, or has a functional group which may be anionic (e.g., —COOH may be —COO), then a salt may be formed with an organic or inorganic base, generating a suitable cation. Examples of suitable inorganic cations include, but are not limited to, alkali metal ions such as $Li^+$, $Na^+$ and $K^+$, alkaline earth metal cations such as $Ca^{2+}$ and $Mg^{2+}$, and other cations such as $Al^{3+}$ or $Zn^+$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: methylamine, ethylamine, diethylamine, propylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the peptides of the invention contain an amine function, these may form quaternary ammonium salts, for example by reaction with an alkylating agent according to methods well known to the skilled person. Such quaternary ammonium compounds are within the scope of the peptides of the invention.

Modified Derivatives

It will be appreciated that modified derivatives of the peptide ligands as defined herein are within the scope of the present invention. Examples of such suitable modified derivatives include one or more modifications selected from: N-terminal and/or C-terminal modifications; replacement of one or more amino acid residues with one or more non-natural amino acid residues (such as replacement of one or more polar amino acid residues with one or more isosteric or isoelectronic amino acids; replacement of one or more non-polar amino acid residues with other non-natural isosteric or isoelectronic amino acids); addition of a spacer group; replacement of one or more oxidation sensitive amino acid residues with one or more oxidation resistant amino acid residues; replacement of one or more amino acid residues with an alanine, replacement of one or more L-amino acid residues with one or more D-amino acid residues; N-alkylation of one or more amide bonds within the bicyclic peptide ligand; replacement of one or more peptide bonds with a surrogate bond; peptide backbone length modification; substitution of the hydrogen on the alpha-carbon of one or more amino acid residues with another chemical group, modification of amino acids such as cysteine, lysine, glutamate/aspartate and tyrosine with suitable amine, thiol, carboxylic acid and phenol-reactive reagents so as to functionalise said amino acids, and introduction or replacement of amino acids that introduce orthogonal reactivities that are suitable for functionalisation, for example azide or alkyne-group bearing amino acids that allow functionalisation with alkyne or azide-bearing moieties, respectively.

In one embodiment, the modified derivative comprises an N-terminal and/or C-terminal modification. In a further embodiment, wherein the modified derivative comprises an N-terminal modification using suitable amino-reactive chemistry, and/or C-terminal modification using suitable carboxy-reactive chemistry. In a further embodiment, said N-terminal or C-terminal modification comprises addition of an effector group, including but not limited to a cytotoxic agent, a radiochelator or a chromophore.

In a further embodiment, the modified derivative comprises an N-terminal modification. In a further embodiment, the N-terminal modification comprises an N-terminal acetyl group. In this embodiment, the N-terminal cysteine group is capped with acetic anhydride or other appropriate reagents during peptide synthesis leading to a molecule which is N-terminally acetylated. This embodiment provides the advantage of removing a potential recognition point for aminopeptidases and avoids the potential for degradation of the bicyclic peptide.

In an alternative embodiment, the N-terminal modification comprises the addition of a molecular spacer group which facilitates the conjugation of effector groups and retention of potency of the bicyclic peptide to its target.

In a further embodiment, the modified derivative comprises a C-terminal modification. In a further embodiment, the C-terminal modification comprises an amide group. In this embodiment, the C-terminal cysteine group is synthesized as an amide during peptide synthesis leading to a molecule which is C-terminally amidated. This embodiment provides the advantage of removing a potential recognition point for carboxypeptidase and reduces the potential for proteolytic degradation of the bicyclic peptide.

In one embodiment, the modified derivative comprises replacement of one or more amino acid residues with one or more non-natural amino acid residues. In this embodiment, non-natural amino acids may be selected having isosteric/isoelectronic side chains which are neither recognised by degradative proteases nor have any adverse effect upon target potency.

Alternatively, non-natural amino acids may be used having constrained amino acid side chains, such that proteolytic hydrolysis of the nearby peptide bond is conformationally and sterically impeded. In particular, these concern proline analogues, bulky sidechains, Ca-disubstituted derivatives (for example, aminoisobutyric acid, Aib), and cyclo amino acids, a simple derivative being amino-cyclopropylcarboxylic acid.

In one embodiment, the modified derivative comprises the addition of a spacer group. In a further embodiment, the modified derivative comprises the addition of a spacer group to the N-terminal cysteine and/or the C-terminal cysteine.

In one embodiment, the modified derivative comprises replacement of one or more oxidation sensitive amino acid residues with one or more oxidation resistant amino acid residues. In a further embodiment, the modified derivative comprises replacement of a tryptophan residue with a naphthylalanine or alanine residue. This embodiment provides the advantage of improving the pharmaceutical stability profile of the resultant bicyclic peptide ligand.

In one embodiment, the modified derivative comprises replacement of one or more charged amino acid residues with one or more hydrophobic amino acid residues. In an alternative embodiment, the modified derivative comprises replacement of one or more hydrophobic amino acid residues with one or more charged amino acid residues. The correct balance of charged versus hydrophobic amino acid residues is an important characteristic of the bicyclic peptide ligands. For example, hydrophobic amino acid residues influence the degree of plasma protein binding and thus the concentration of the free available fraction in plasma, while charged amino acid residues (in particular arginine) may influence the interaction of the peptide with the phospholipid membranes on cell surfaces. The two in combination may influence half-life, volume of distribution and exposure of the peptide drug, and can be tailored according to the clinical endpoint. In addition, the correct combination and number of charged versus hydrophobic amino acid residues may reduce irritation at the injection site (if the peptide drug has been administered subcutaneously).

In one embodiment, the modified derivative comprises replacement of one or more L-amino acid residues with one or more D-amino acid residues. This embodiment is believed to increase proteolytic stability by steric hindrance and by a propensity of D-amino acids to stabilise β-turn conformations (Tugyi et al. (2005) PNAS, 102(2), 413-418).

In one embodiment, the modified derivative comprises removal of any amino acid residues and substitution with alanines. This embodiment provides the advantage of removing potential proteolytic attack site(s).

It should be noted that each of the above mentioned modifications serve to deliberately improve the potency or stability of the peptide. Further potency improvements based on modifications may be achieved through the following mechanisms:

Incorporating hydrophobic moieties that exploit the hydrophobic effect and lead to lower off rates, such that higher affinities are achieved;

Incorporating charged groups that exploit long-range ionic interactions, leading to faster on rates and to higher affinities (see for example Schreiber et al. (1996) Rapid, electrostatically assisted association of proteins, Nature Struct. Biol. 3, 427-31); and Incorporating additional constraint into the peptide, by for example constraining side chains of amino acids correctly such that loss in entropy is minimal upon target binding, constraining the torsional angles of the backbone such that loss in entropy is minimal upon target binding and introducing additional cyclisations in the molecule for identical reasons.

(for reviews see Gentilucci et al., Curr. Pharmaceutical Design, (2010), 16, 3185-203, and Nestor et al, Curr. Medicinal Chem (2009), 16, 4399-418).

Isotopic Variations

The present invention includes all pharmaceutically acceptable (radio)isotope-labeled peptide ligands of the invention, wherein one or more atoms are replaced by atoms having the same atomic number, but an atomic mass or mass number different from the atomic mass or mass number usually found in nature, and peptide ligands of the invention, wherein metal chelating groups are attached (termed "effector") that are capable of holding relevant (radio)isotopes, and peptide ligands of the invention, wherein certain functional groups are covalently replaced with relevant (radio)isotopes or isotopically labelled functional groups.

Examples of isotopes suitable for inclusion in the peptide ligands of the invention comprise isotopes of hydrogen, such as $^2$H (D) and $^3$H (T), carbon, such as $^{11}$C, $^{13}$C and $^{14}$C, chlorine, such as $^{36}$Cl, fluorine, such as $^{18}$F, iodine, such as $^{123}$I, $^{125}$I and $^{131}$I, nitrogen, such as $^{13}$N and $^{15}$N, oxygen, such as $^{15}$O, $^{17}$O and $^{18}$O, phosphorus, such as $^{32}$P, sulfur, such as $^{35}$S, copper, such as $^{64}$Cu, gallium, such as $^{67}$Ga or $^{68}$Ga, yttrium, such as $^{90}$Y and lutetium, such as $^{177}$Lu, and Bismuth, such as $^{213}$Bi.

Certain isotopically-labelled peptide ligands of the invention, for example, those incorporating a radioactive isotope, are useful in drug and/or substrate tissue distribution studies, and to clinically assess the presence and/or absence of the TSLP target on diseased tissues. The peptide ligands of the invention can further have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^3$H (T), and carbon-14, i.e. $^{14}$C, are particularly useful for this purpose in view of their ease of incorporation and ready means of detection.

Substitution with heavier isotopes such as deuterium, i.e. $^2$H (D), may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining target occupancy.

Isotopically-labeled compounds of peptide ligands of the invention can generally be prepared by conventional techniques known to those skilled in the art or by processes analogous to those described in the accompanying Examples using an appropriate isotopically-labeled reagent in place of the non-labeled reagent previously employed.

Molecular Scaffold

Molecular scaffolds are described in, for example, WO 2009/098450 and references cited therein, particularly WO 2004/077062 and WO 2006/078161.

In one embodiment, the molecular scaffold is a non-aromatic scaffold. References herein to "non-aromatic molecular scaffold" refer to any molecular scaffold as defined herein which does not contain an aromatic (i.e. unsaturated) carbocyclic or heterocyclic ring system.

Suitable examples of non-aromatic molecular scaffolds are described in Heinis et al (2014) Angewandte Chemie, International Edition 53(6) 1602-1606.

As noted in the foregoing documents, the molecular scaffold may be a small molecule, such as a small organic molecule.

In one embodiment the molecular scaffold may be a macromolecule. In one embodiment the molecular scaffold is a macromolecule composed of amino acids, nucleotides or carbohydrates.

In one embodiment the molecular scaffold comprises reactive groups that are capable of reacting with functional group(s) of the polypeptide to form covalent bonds.

The molecular scaffold may comprise chemical groups which form the linkage with a peptide, such as amines, thiols, alcohols, ketones, aldehydes, nitriles, carboxylic acids, esters, alkenes, alkynes, azides, anhydrides, succinimides, maleimides, alkyl halides and acyl halides.

An example of an αβ unsaturated carbonyl containing compound is 1,1',1"-(1,3,5-triazinane-1,3,5-triyl)triprop-2-en-1-one (TATA) (Angewandte Chemie, International Edition (2014), 53(6), 1602-1606).

Binding Activity

Specificity, in the context herein, refers to the ability of a ligand to bind or otherwise interact with its cognate target to the exclusion of entities which are similar to the target. For example, specificity can refer to the ability of a ligand to inhibit the interaction of a human enzyme, but not a homologous enzyme from a different species. Using the approach described herein, specificity can be modulated, that is increased or decreased, so as to make the ligands more or less able to interact with homologues or paralogues of the intended target. Specificity is not intended to be synonymous with activity, affinity or avidity, and the potency of the action of a ligand on its target (such as, for example, binding affinity or level of inhibition) are not necessarily related to its specificity.

Binding activity, as used herein, refers to quantitative binding measurements taken from binding assays, for example as described herein. Therefore, binding activity refers to the amount of peptide ligand which is bound at a given target concentration.

Multispecificity is the ability to bind to two or more targets. Typically, binding peptides are capable of binding to a single target, such as an epitope in the case of an antibody, due to their conformational properties. However, peptides can be developed which can bind to two or more targets; dual specific antibodies, for example, as known in the art as referred to above. In the present invention, the peptide ligands can be capable of binding to two or more targets and are therefore multispecific. Suitably, they bind to two targets, and are dual specific. The binding may be independent, which would mean that the binding sites for the targets on the peptide are not structurally hindered by the binding of one or other of the targets. In this case, both targets can be bound independently. More generally, it is expected that the binding of one target will at least partially impede the binding of the other.

There is a fundamental difference between a dual specific ligand and a ligand with specificity which encompasses two related targets. In the first case, the ligand is specific for both targets individually, and interacts with each in a specific manner. For example, a first loop in the ligand may bind to a first target, and a second loop to a second target. In the second case, the ligand is non-specific because it does not differentiate between the two targets, for example by interacting with an epitope of the targets which is common to both.

In the context of the present invention, it is possible that a ligand which has activity in respect of, for example, a target and an orthologue, could be a bispecific ligand. However, in one embodiment the ligand is not bispecific, but has a less precise specificity such that it binds both the target and one or more orthologues. In general, a ligand which has not been selected against both a target and its orthologue is less likely to be bispecific due to the absence of selective pressure towards bispecificity. The loop length in the bicyclic peptide may be decisive in providing a tailored binding surface such that good target and orthologue cross-reactivity can be obtained, while maintaining high selectivity towards less related homologues.

If the ligands are truly bispecific, in one embodiment at least one of the target specificities of the ligands will be common amongst the ligands selected, and the level of that specificity can be modulated by the methods disclosed herein. Second or further specificities need not be shared and need not be the subject of the procedures set forth herein.

A target is a molecule or part thereof to which the peptide ligands bind or otherwise interact with. Although binding is seen as a prerequisite to activity of most kinds, and may be an activity in itself, other activities are envisaged. Thus, the present invention does not require the measurement of binding directly or indirectly.

The molecular scaffold is any molecule which is able to connect the peptide at multiple points to impart one or more structural features to the peptide. Preferably, the molecular scaffold comprises at least three attachment points for the peptide, referred to as scaffold reactive groups. These groups are capable of reacting with the cysteine residues on the peptide to form a covalent bond. They do not merely form a disulphide bond, which is subject to reductive cleavage and concomitant disintegration of the molecule, but form stable, covalent thioether linkages. Preferred structures for molecular scaffolds are described below.

Synthesis

The peptides of the present invention may be manufactured synthetically by standard techniques followed by reaction with a molecular scaffold in vitro. When this is performed, standard chemistry may be used. This enables the rapid large scale preparation of soluble material for further downstream experiments or validation. Such methods could be accomplished using conventional chemistry such as that disclosed in Timmerman et al (supra).

Thus, the invention also relates to manufacture of polypeptides selected as set out herein, wherein the manufacture comprises optional further steps as explained below. In one embodiment, these steps are carried out on the end product polypeptide made by chemical synthesis.

Optionally amino acid residues in the polypeptide of interest may be substituted when manufacturing a conjugate or complex.

Peptides can also be extended, to incorporate for example another loop and therefore introduce multiple specificities.

To extend the peptide, it may simply be extended chemically at its N-terminus or C-terminus or within the loops using orthogonally protected lysines (and analogues) using standard solid phase or solution phase chemistry. Standard (bio)conjugation techniques may be used to introduce an activated or activatable N- or C-terminus. Alternatively additions may be made by fragment condensation or native chemical ligation e.g. as described in (Dawson et al. 1994. Synthesis of Proteins by Native Chemical Ligation. Science 266:776-779), or by enzymes, for example using subtiligase as described in (Chang et al Proc Natl Acad Sci USA. 1994 Dec. 20; 91(26):12544-8 or in Hikari et al Bioorganic & Medicinal Chemistry Letters Volume 18, Issue 22, 15 Nov. 2008, Pages 6000-6003).

Alternatively, the peptides may be extended or modified by further conjugation through disulphide bonds. This has the additional advantage of allowing the first and second peptide to dissociate from each other once within the reducing environment of the cell. In this case, the molecular scaffold (e.g. TATA) could be added during the chemical synthesis of the first peptide so as to react with the three cysteine groups; a further cysteine or thiol could then be appended to the N or C-terminus of the first peptide, so that this cysteine or thiol only reacted with a free cysteine or thiol of the second peptide, forming a disulphide-linked bicyclic peptide-peptide conjugate.

Similar techniques apply equally to the synthesis/coupling of two bicyclic and bispecific macrocycles, potentially creating a tetraspecific molecule.

Furthermore, addition of other functional groups or effector groups may be accomplished in the same manner, using appropriate chemistry, coupling at the N- or C-termini or via side chains. In one embodiment, the coupling is conducted in such a manner that it does not block the activity of either entity.

Pharmaceutical Compositions

According to a further aspect of the invention, there is provided a pharmaceutical composition comprising a peptide ligand as defined herein in combination with one or more pharmaceutically acceptable excipients.

Generally, the present peptide ligands will be utilised in purified form together with pharmacologically appropriate excipients or carriers. Typically, these excipients or carriers include aqueous or alcoholic/aqueous solutions, emulsions or suspensions, including saline and/or buffered media. Parenteral vehicles include sodium chloride solution, Ringers dextrose, dextrose and sodium chloride and lactated Ringers. Suitable physiologically-acceptable adjuvants, if necessary to keep a polypeptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringer's dextrose. Preservatives and other additives, such as antimicrobials, antioxidants, chelating agents and inert gases, may also be present (Mack (1982) Remington's Pharmaceutical Sciences, 16th Edition).

The peptide ligands of the present invention may be used as separately administered compositions or in conjunction with other agents. These can include antibodies, antibody fragments and various immunotherapeutic drugs, such as cyclosporine, methotrexate, adriamycin or cisplatinum and immunotoxins. Pharmaceutical compositions can include "cocktails" of various cytotoxic or other agents in conjunction with the protein ligands of the present invention, or even combinations of selected polypeptides according to the present invention having different specificities, such as polypeptides selected using different target ligands, whether or not they are pooled prior to administration.

The route of administration of pharmaceutical compositions according to the invention may be any of those commonly known to those of ordinary skill in the art. For therapy, the peptide ligands of the invention can be administered to any patient in accordance with standard techniques. The administration can be by any appropriate mode, including parenterally, intravenously, intramuscularly, intraperitoneally, transdermally, via the pulmonary route, or also, appropriately, by direct infusion with a catheter. Preferably, the pharmaceutical compositions according to the invention will be administered by inhalation. The dosage and frequency of administration will depend on the age, sex and condition of the patient, concurrent administration of other drugs, counterindications and other parameters to be taken into account by the clinician.

The peptide ligands of this invention can be lyophilised for storage and reconstituted in a suitable carrier prior to use. This technique has been shown to be effective and art-known lyophilisation and reconstitution techniques can be employed. It will be appreciated by those skilled in the art that lyophilisation and reconstitution can lead to varying degrees of activity loss and that levels may have to be adjusted upward to compensate.

The compositions containing the present peptide ligands or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease and the general state of the patient's own immune system, but generally range from 0.005 to 5.0 mg of selected peptide ligand per kilogram of body weight, with doses of 0.05 to 2.0 mg/kg/dose being more commonly used. For prophylactic applications, compositions containing the present peptide ligands or cocktails thereof may also be administered in similar or slightly lower dosages.

A composition containing a peptide ligand according to the present invention may be utilised in prophylactic and therapeutic settings to aid in the alteration, inactivation, killing or removal of a select target cell population in a mammal. In addition, the peptide ligands described herein may be used extracorporeally or in vitro selectively to kill, deplete or otherwise effectively remove a target cell population from a heterogeneous collection of cells. Blood from a mammal may be combined extracorporeally with the selected peptide ligands whereby the undesired cells are killed or otherwise removed from the blood for return to the mammal in accordance with standard techniques.

Therapeutic Uses

The bicyclic peptides of the invention have specific utility as TSLP binding agents. Thymic stromal lymphopoietin (TSLP) is a protein belonging to the cytokine family. It is known to play an important role in the maturation of T cell populations through activation of antigen presenting cells. TSLP is produced mainly by non-hematopoietic cells such as fibroblasts, epithelial cells and different types of stromal or stromal-like cells. These cells are located in regions where TSLP activity is required. TSLP ainly impacts myeloid cells and induces the release of T cell-attracting chemokines from monocytes and enhances the maturation of myeloid (CD11c+) dendritic cells. TSLP has also been shown to activate the maturation of a specific subset of dendritic cells located within the epidermis, called Langerhans cells. Within the thymus TSLP activation of both myeloid and plasmacytoid (CD123+) dendritic cells results in the production of regulatory T cells, TSLP signals through a heterodimeric receptor complex composed of the thymic stromal lymphopoietin receptor CRLF2 and the IL-7R alpha chain. After binding STATS phosphorylation is induced resulting in the expression of upstream transcription factors.

Polypeptide ligands selected according to the method of the present invention may be employed in in vivo therapeutic and prophylactic applications, in vitro and in vivo diagnostic applications, in vitro assay and reagent applications, and the like. Ligands having selected levels of specificity are useful in applications which involve testing in non-human animals, where cross-reactivity is desirable, or in diagnostic applications, where cross-reactivity with homologues or paralogues needs to be carefully controlled. In some applications, such as vaccine applications, the ability to elicit an immune response to predetermined ranges of antigens can be exploited to tailor a vaccine to specific diseases and pathogens.

Substantially pure peptide ligands of at least 90 to 95% homogeneity are preferred for administration to a mammal, and 98 to 99% or more homogeneity is most preferred for pharmaceutical uses, especially when the mammal is a human. Once purified, partially or to homogeneity as desired, the selected polypeptides may be used diagnostically or therapeutically (including extracorporeally) or in developing and performing assay procedures, immunofluorescent stainings and the like (Lefkovite and Pernis, (1979 and 1981) Immunological Methods, Volumes I and II, Academic Press, NY).

According to a further aspect of the invention, there is provided a peptide ligand as defined herein, for use in preventing, suppressing or treating a disease or disorder mediated by TSLP.

According to a further aspect of the invention, there is provided a method of preventing, suppressing or treating a disease or disorder mediated by TSLP, which comprises administering to a patient in need thereof the peptide ligand as defined herein.

In one embodiment, the TSLP is mammalian TSLP. In a further embodiment, the mammalian TSLP is human TSLP.

In one embodiment, the disease or disorder mediated by TSLP is selected from: respiratory disorders, inflammatory disorders, skin disorders and allergic disorders.

In a further embodiment, the disease or disorder mediated by TSLP is selected from: respiratory disorders (such as asthma), inflammatory disorders (such as inflammatory arthritis and eosinophilic esophagitis), skin disorders (such as atopic dermatitis and eczema) and allergic disorders.

In a yet further embodiment, the disease or disorder mediated by TSLP is selected from: respiratory disorders (such as asthma and COPD).

In a yet further embodiment, the disease or disorder mediated by TSLP is selected from: asthma, inflammatory arthritis, atopic dermatitis, eczema and eosinophilic esophagitis.

In a yet further embodiment, the disease or disorder mediated by TSLP is asthma.

References herein to the term "prevention" involves administration of the protective composition prior to the induction of the disease. "Suppression" refers to administration of the composition after an inductive event, but prior to the clinical appearance of the disease. "Treatment" involves administration of the protective composition after disease symptoms become manifest.

Animal model systems which can be used to screen the effectiveness of the peptide ligands in protecting against or treating the disease are available. The use of animal model systems is facilitated by the present invention, which allows the development of polypeptide ligands which can cross react with human and animal targets, to allow the use of animal models.

The invention is further described below with reference to the following examples.

EXAMPLES

Abbreviations
Anbu 3-(n-butyl)-alanine
Ac acetate
ACN acetonitrile
3-AcNH4ClPhe 3-(acetylamino)-4-chloro-phenylalanine
ADMA assymetric dimethylargine
Agb 2-amino-4-guanidinobutyric acid
AMe N-methyl alanine
Bn benzyl
BnA 3-benzyl-alanine
Boc$_2$O di-tert-butyl dicarbonate
3-BrPhe 3-bromo-phenylalanine
4-BrPhe 4-bromo-phenylalanine
ButG n-butyl-glycine
Bz benzoyl
Can canavanine
CDI 1,1'-carbonyldiimidazole
4-CF3Phe 4-trifluoromethyl-phenylalanine
Cha 3-cyclohexyl alanine
ChMeA 3-cyclohexylmethyl alanine
Chx-P L-octahydro-1H-indole-2-carboxylic acid (cyclohexyl) proline
Cit citrulline
4-ClNal 4-chloro-1-naphthylalanine
3-ClPhe 3-chloro-phenylalanine
4-ClPhe 4-chloro-phenylalanine
3-CNPhe 3-cyano-phenylalanine
4-CNPhe 4-cyano-phenylalanine
CpentA 3-cyclopentyl-alanine
CproA 3-cyclopropyl-alanine
Dap diaminopropionic acid
DCM dichloromethane
DIC N,N-diisopropylcarbodiimide
diF-P 4,4 difluoro proline
3,4diFPhe 3,4-difluoromethyl-phenylalanine
3,4diClPhe 3,4-dichloromethyl-phenylalanine
3,5diF,4ClPhe 3,5-difluoromethyl-4-chloro-phenylalanine
DIPEA diisopropylethylamine
DMAP 4-N,N-dimethylamino pyridine
DMF dimethylformamide
DMSO dimethylsulfoxide
DODT 3,6-dioxa-1,8-octanedithiol
dppf 1,1'-bis(diphenylphosphino)ferrocene
EDC $N^1$-((ethylimino)methylene)-$N^3$,$N^3$-dimethylpropane-1,3-diamine hydrochloride
ES/ESI electrospray ionization
EtOH ethanol
EtOAc ethyl acetate
2-FPhe 2-fluoro-phenylalanine
3-FPhe 3-fluoro-phenylalanine
4-FPhe 4-fluoro-phenylalanine
3-F,4-ClPhe 3-fluoro-4-chloro-phenylalanine
4-F3C3ClPhe 4-trifluoromethyl-3-chloro-phenylalanine
Fmoc-Cl 9-fluorenylmethyl chloroformate
5-FTrp 5-fluoro-tryptophan
h hour
HArg homoarginine
HATU 1-[bis(dimethylamino)methylene]-1H-1,2,3-triazolo[4,5-b]pyridinium 3-oxid hexafluorophosphate
HOBt 1H-benzo[d][1,2,3]triazol-1-ol hydrate
HPLC high performance liquid chromatography
iPrMeA 3-isopropylmethyl alanine
LHMDS lithium bis(trimethylsilyl)amide
LMe Na-methyl leucine
LysMe3 ω,ω,ω-trimethyl lysine
mCPBA 3-chloroperoxybenzoic acid
MeD N-methyl aspartic acid
4-MenL 4-methyl norleucine
MeOH methanol
3-MePhe 3-methyl-phenylalanine
4-MePhe 4-methyl-phenylalanine
4-MeOPhe 4-methoxy-phenylalanine M(O) methionine oxide
MTBE methyl-tert-butylether
Nal1 1-naphthylalanine
Nal2 2-naphthylalanine
NeopentA 3-neopentyl-alanine
Nle norleucine
NMP N-methyl pyrrolidinone
NMeA N-methylalanine
Nva nor-valine
7-OMeTrp 7-methoxy-tryptophan
Orn ornithine
Oxyma ethyl cyano(hydroxyimino)acetate
PentFPhe pentafluoro-phenylalanine
5-Ph-P 5-phenyl proline
4-PipA 3-(4-piperidyl)-alanine
Piv pivaloyl
2-PyrA 3-(2-pyridyl)-alanine
3-PyrA 3-(3-pyridyl)-alanine
4-PyrA 3-(4-pyridyl)-alanine
rt room temperature
RT retention time
RP-HPLC reverse phase HPLC
SFC supercritical fluid chromatography
SPPS solid phase peptide synthesis
TATA 1,3,5-triacryloyl-1,3,5-triazinane
TEA triethylamine
T3P 2,4,6-tripropyl-1,3,5,2,4,6-trioxatriphosphinane 2,4,6-trioxide
TBAF tetra-n-butylammonium fluoride
TBDMSCl tert-butyldimethylsilyl chloride
TBDMSOTf tert-butyldimethylsilyl trifluoromethanesulfonate
TBTU 2-(1H-benzo[d][1,2,3]triazol-1-yl)-1,1,3,3-tetramethylisouronium tetrafluoroborate
tBuA t-butyl-alanine
TFA trifluoroacetic acid
TFAA trifluoroacetic anhydride
THF tetrahydrofuran
2-ThienylA 3-(2-thienyl)-alanine
3-ThienylA 3-(3-thienyl)-alanine
TIS triisopropylsilane
TriFMeA 3-trifluoromethyl alanine
TriMeK ω,ω,ω-trimethyl lysine
TrpMe 1-methyl-tryptophan
3,4,5triFPhe 3,4,5-trifluoromethyl-phenylalanine General Methods NMR spectra were recorded on a Bruker Avance, Avance II or Avance III spectrometer at a proton frequency of 300, 400, 500 or 600 MHz. The central peaks of chloroform-δ (H 7.26 ppm), $CD_3OD$ (H 3.30 ppm) or DMSO-$d_6$ (H 2.50 ppm) were used as internal references. LCMS experiments were performed using a Waters Acquity system combined with a Waters Xevo Q-ToF Mass in ESI mode. LC was run in two set ups: 1) BEH C18 column (1.7 μm 2.1×50 mm) in combination with a gradient (2-95% B in 5 minutes) of aqueous 46 mM ammonium carbonate/ammonia buffer at pH 10 (A) and MeCN (B) at a flow rate of 1.0 mL/min or in combination with a gradient (5-95% B in 2 minutes) of water and TFA (0.05%) (A) and $CH_3CN$ and TFA (0.05%) at a flow rate of 1.0 mL/min (B). HRMS (High Resolution Mass Spectrometry) was run on a high resolution (R=9000 fwhm) LCMS system (Waters Acquity-Xevo Q-ToF) with electrospray ionization (ESI). Preparative HPLC was performed with a Waters FractionLynx system with integrated MS detection or Gilson GX-281 with integrated UV detection using a variety of columns. Examples are Waters Sunfire C18 OBD 5 μm 19 mm×150 mm or 30 mm×150 mm, XBridge BEH C18 OBD 5 μm 19 mm×150 mm or 30 mm×150 mm, Xselect CSH C18 OBD 5 μm 19 mm×150 mm or Chromasil C8 10 μm 20 mm×250 mm or 50 mm×250 mm columns.

Material and Methods

Protein Reagents

Human TSLP & TSLP receptor

Cloning

Full length human TSLP with a TEV cleavable N-terminal 6×HN tag, a C-terminal Avi-tag and a native signal sequence exchanged for a cd33 signal sequence was codon-optimized for HEK cells and synthesized by Genscript. The resulting construct spCD33-6×HN-TEV-hTSLP(29-159)-Avi was cloned into an in-house pEBNAZ vector (pDEST12.2 derivative) using SacII and NotI restriction enzyme sites.

TSLP sequence:
(SEQ ID NO: 164)
MPLLLLLPLLWAGALAHNHNHNHNHNHNAAENLYFQYDFTNCDFEKIKAA

YLSTISKDLITYMSGTKSTEFNNTVSCSNRPHCLTEIQSLTFNPTAGCAS

LAKEMFAMKTKAALAIWCPGYSETQINATQAMKKRRKRKVTTNKCLEQVS

QLQGLWRRFNRPLLKQQQGLNDIFEAQKIEWHE.

Full length human TSLP receptor with a TEV cleavable N-terminal 6×HN tag and a native signal sequence exchanged for an IgK signal sequence was codon-optimized for HEK cells and synthesized by Genscript. The resulting construct spCD33-6×HN-TEV-hTSLPR(25-231) was cloned into an in-house pEBNAZ vector (pDEST12.2 derivative) using SacII and NotI restriction enzyme sites.

TSLPR sequence:
(SEQ ID NO: 165)
METDTLLLWVLLLWVPGSTGHNHNHNHNHNHNAAENLYFQGAAEGVQIQI

IYFNLETVQVTWNASKYSRTNLTFHYRFNGDEAYDQCTNYLLQEGHTSGC

LLDAEQRDDILYFSIRNGTHPVFTASRWMVYYLKPSSPKHVRFSWHQDAV

TVTCSDLSYGDLLYEVQYRSPFDTEWQSKQENTCNVTIEGLDAEKCYSFW

VRVKAMEDVYGPDTYPSDWSEVTCWQRGEIRDACAETPTPPKPKLSK

Cell Culture and Transient Transfection

The transfection grade plasmid encoding the target spCD33-6×HN-TEV-hTSLP(29-159) was received from Genscript. Expi293F cells were grown in serum-free Expi293 Expression Medium (Thermo Fisher Scientific) and maintained in Erlenmeyer Flasks (Corning Inc.) at 37° C. with 8% $CO_2$ in a 25 mm orbital shaking incubator (Infors HT). One day prior to transfection, the cells were seeded at 2×10e6 c/ml in an Optimum Growth Flask (Thomson Instrument Company). On the day of transfection, 1.5 μg/ml DNA and 6 μg/ml PEI Max (Polysciences, Inc.) were separately diluted in Expi293 Expression medium and then mixed (1:4 DNA/PEI ratio) and incubated for 15 min at rt. The resulting transfection complexes were added to the cell culture followed by incubation at 37° C., 8% $CO_2$. 115 rpm. The cells were fed with 50% (v/v) Expi293 Expression Medium 24 h post transfection. The culture supernatant was harvested after 6 days of incubation.

Purification

The hTSLP and hTSLPR were directly captured from the media by batch binding to Excel resin, in the presence of 5 mM imidazole. The resin was then transferred to small column and washed with a buffer containing 20 mM Tris·HCl pH 7.5, 500 mM NaCl and 20 mM imidazole. The resin was eluted in the same buffer but containing 400 mM imidazole. The proteins were desalted into buffer containing 20 mM Tris·HCl pH 7.5 and 200 mM NaCl. TSLP was further treated with TEV (added at 1:1 stoichiometry) for 3 hours at 10° C., followed by negative immobilized-metal affinity chromatography.

Human IL7 Receptor Alpha

Human IL7Ralpha (His & FC tag) was purchased from Sino Biological, catalog number 10975-H08H-100.

Peptide Synthesis

Linear peptides were synthesized by solid-phase peptide synthesis (SPPS), based on Fmoc chemistry, using one of the following peptide synthesisers: Symphony, manufactured by Peptide Instruments, Biotage Initiator+ Alstra and Syro II from Biotage and Liberty Blue from CEM. Rink Amide ChemMatrix resin (100-200 mesh) from Biotage with a loading of around 0.5 mmol/g was used unless otherwise stated. Standard Fmoc-amino acids were employed with the following side chain protecting groups: Arg(Pbf) or Arg(Boc)$_2$; Asn(Trt); Asp(OtBu); Cys(Trt); Glu(OtBu); Gln(Trt); His(Trt); Lys(Boc); Ser(tBu); Thr(tBu); Trp(Boc); and Tyr(tBu). The identity and purity of the products were determined by LCMS and HRMS.

All amino acids, unless stated otherwise, were used in the L-configuration.

Non-natural amino acids were incorporated into the peptide sequence using the general methods described above.

The list of non-natural amino acid precursors employed herein are summarised in Table 1:

TABLE 1

| Non-natural amino acids employed | | |
|---|---|---|
| Source | Short name | Coupling precursor |
| Merck/Novabiochem | ADMA | Fmoc-ADMA(Pbf)-OH |
| Combi-Blocks Inc. | 4-FPhe | Fmoc-Phe(4-F)—OH |
| Chem-Impex International, Inc. | 4-ClPhe | Fmoc-Phe(4-Cl)—OH |
| Chem-Impex International, Inc. | 3-FPhe | Fmoc-Phe(3-F)—OH |
| Chem-Impex International, Inc. | 2-FPhe | Fmoc-Phe(2-F)—OH |
| Prepared, intermediate 1 | 3-F,4-ClPhe | Fmoc-Phe(3-F,4-Cl)—OH |
| Prepared, intermediate 2 | 4-ClNal | Fmoc-β-(1-(4-Cl-naphthyl)-Ala-OH |
| Prepared, intermediate 3 | 3,5diF,4ClPhe | Fmoc-Phe(3,5-F2,4-Cl)—OH |
| Prepared, intermediate 4 | 3-Cl-4-FPhe | Fmoc-Phe(3-Cl,4-F)—OH |
| Prepared, intermediate 5 | 3-NHAc-4-ClPhe | Fmoc-Phe(3-NHAc,4-Cl)—OH |
| Combi-Blocks Inc. | 3-ClPhe | Fmoc-Phe(3-Cl)—OH |
| Combi-Blocks Inc. | PentaFPhe | Fmoc-Phe(F5)—OH |
| Combi-Blocks Inc. | 3,4-diClPhe | Fmoc-Phe(3,4-Cl2)—OH |
| Combi-Blocks Inc. | 3,4,5-triFPhe | Fmoc-Phe(3,4,5-F3)—OH |
| Combi-Blocks Inc. | 3,4-diF-Phe | Fmoc-Phe(4,3-F2)—OH |
| Chem-Impex International, Inc. | 3-BrPhe | Fmoc-Phe(3-Br)—OH |
| Chem-Impex International, Inc. | 3-CNPhe | Fmoc-Phe(3-CN)—OH |
| Sigma-Aldrich | 4-CNPhe | Fmoc-Phe(4-CN)—OH |
| Sigma-Aldrich | 1-Nal | Fmoc-β-(1-naphthyl)-Ala-OH |
| Chem-Impex International, Inc. | 2-Nal | Fmoc-β-(2-naphthyl)-Ala-OH |
| Fluorochem Limited | 2-ThienylA | Fmoc-β-(2-thienyl)-Ala-OH |
| Chem-Impex International, Inc. | 2-ThienylA | Fmoc-β-(3-thienyl)-Ala-OH |
| Fisher Scientific (Acros Organics) | 2-PyrA | Fmoc-β-(2-pyridyl)-Ala-OH |
| Sigma-Aldrich | 3-PyrA | Fmoc-β-(3-pyridyl)-Ala-OH |
| Sigma-Aldrich | 4-PyrA | Fmoc-β-(4-pyridyl)-Ala-OH |
| Chem-Impex International, Inc. | 3-MePhe | Fmoc-Phe(3-Me)—OH |
| Combi-Blocks Inc. | 4-MePhe | Fmoc-Phe(4-Me)—OH |
| Sigma-Aldrich | 4-CF3Phe | Fmoc-Phe(4-CF3)—OH |
| Merck (Novabiochem) | 4-MeOPhe | Fmoc-Phe(4-OMe)—OH |
| Chem-Impex International, Inc. | hPhe | Fmoc-hPhe-OH |
| Merck (Novabiochem) | TrpMe | Fmoc-N-Me-Trp(Boc)-OH |
| Combi-Blocks Inc. | tBuA | Fmoc-Ala(tBu)—OH |
| Chem-Impex International, Inc. | hLeu | Fmoc-hLeu-OH |
| Bachem AG | CyclopropA | Fmoc-Ala-β-Cyclopropyl-OH |
| Chem-Impex International, Inc. | CycloLeu | Fmoc-NH(1)-Cyclopentane-OH |
| Bachem AG | NVA | Fmoc-NorVal-OH |
| Chem-Impex International, Inc. | αAminocyclohexane carboxylic acid | Fmoc-NH(1)-Cyclohexane-OH |
| Bachem AG | Met(O) | Fmoc-Met(O)—OH |
| Combi-Blocks Inc. | NLeu | Fmoc-NorLeucine-OH |
| Chem-Impex International, Inc. | hAla | Fmoc-HomoAla-OH |
| Chem-Impex International, Inc. | HOCHA | Fmoc-HomoCyclohexylAla-OH |
| Chem-Impex International, Inc. | ChexA | Fmoc-CyclohexylAla-OH |
| Sigma-Aldrich | CyclopentA | Fmoc-CyclopentylAla-OH |
| Ark Pharm, Inc. | CF$_3$A | D,L-Fmoc-4,4,4-TriFluoro-α-HomoAla |
| Zylexa Pharma | — | Fmoc- (2S)-2-aminohex-5-enoic acid |

Protocol 1: Synthesis Using the Symphony Synthesiser

Peptide synthesis was based on Fmoc chemistry, using a Symphony peptide synthesiser manufactured by Peptide Instruments. Standard Fmoc-amino acids were employed (Sigma, Merck), with appropriate side chain protecting groups: where applicable standard coupling conditions were used in each case, followed by deprotection using standard methodology. Peptides were purified using HPLC and following isolation they were modified with 1,3,5-triacryloyl-hexahydro-1,3,5-triazine (TATA, Sigma). For this, linear peptide was diluted with 50:50 MeCN:$H_2O$ up to ~35 mL, ~500 µL of 100 mM TATA in acetonitrile was added, and the reaction was initiated with 5 mL of 1 M $NH_4HCO_3$ in $H_2O$. The reaction was allowed to proceed for ~30-60 min at rt, and lyophilised once the reaction had completed (judged by MALDI). Once completed, 1 ml of 1M L-cysteine hydrochloride monohydrate (Sigma) in $H_2O$ was added to the reaction for ~60 min at rt to quench any excess TATA. Following lyophilisation, the modified peptide was purified as above, while replacing the Luna C8 with a Gemini C18 column (Phenomenex), and changing the acid to 0.1% trifluoroacetic acid. Pure fractions containing the correct TATA-modified material were pooled, lyophilised and kept at 20° C. for storage.

Protocol 2: Synthesis Using the Biotage Initiator+ Alstra Synthesiser

The peptides were synthesized in 0.1-0.5 mmol scale in 10 or 30 mL reactor vials on a Biotage Initiator+ Alstra. Agitation was done in cycles of vortexing and pause. The reactions were heated in a microwave single-node cavity. Solutions of the amino acids and reagents were kept under $N_2$ atmosphere.

A typical procedure is described below.

After swelling of the resin in DCM or DMF (4.5 mL for the 10 mL reactor or 9 mL for the 30 mL reactor) and the reactor was emptied. To the resin (1 eq) was added sequentially a solution of the Fmoc-amino acid in DMF (0.1-0.3 M, 4 eq), a solution of ethyl cyano(hydroxyimino)acetate (Oxyma) in DMF (0.24 M, 4 eq) and a solution of N,N'-diisopropylcarbodiimide (DIC) in DMF (1.0 M, 4 eq). The reaction was heated at 75° C. for 5 minutes, except in the case of coupling of Fmoc-S-trityl-cysteine, which was coupled at 45-50° C. for 20 minutes. For Fmoc-Arg-Pbf, the coupling step was repeated twice. After the reaction, the resin was washed four times with DMF (4.5 mL for the 10 mL reactor or 9 mL for the 30 mL reactor).

Deprotection of the Fmoc-group was conducted as follows: To the washed resin was added a solution of piperidine in DMF (20%, 4.5 mL for the 10 mL reactor or 9 mL for the 30 mL reactor). The reaction was run at rt for 3 minutes. The solvent was removed and the process was repeated, but the reaction was run for 10 minutes. The reactor was emptied and the resin was washed four times with DMF (4.5 mL for the 10 mL reactor or 9 mL for the 30 mL reactor). After preparation of the desired peptide sequence, the Fmoc group was typically cleaved off, and the N-terminus capped with an acetyl group as follows: To the washed resin was added a solution of acetic anhydride in DMF (5 M, 4 eq) and a solution of DIPEA in NMP (2 M, 4 eq). After 10 minutes reaction the resin was washed four times with DMF (4.5 mL for the 10 mL reactor or 9 mL for the 30 mL reactor).

A final wash before cleavage was performed as follows: To the washed resin was added DCM (4.5 mL for the 10 mL reactor or 9 mL for the 30 mL reactor) and the reactor was emptied. This procedure was repeated six times before the resin was dried under vacuum and stored in a freezer.

Protocol 3: Synthesis Using the Biotage SYRO II Synthesiser

The peptides were synthesized in 0.05 or 0.1 mmol scale in 10 mL reactor vials on a Biotage SYRO II (automated parallel peptide synthesizer). The synthesizer was operated at rt under $N_2$ atmosphere and agitation was done in cycles of vortexing and paused.

Swelling of the resin was done six times in DMF as follows: To the resin was added DMF (1.3 mL) and it was agitated for 5 minutes before the reactor was emptied.

Coupling of the amino acid was conducted twice with a 4-fold molar excess as follows: To the washed resin (1 eq) was added sequentially a solution of the Fmoc-amino acid in DMF (0.25 M, 4 eq), followed by solutions of 1-[bis (dimethylamino)methylene]-1H-1,2,3-triazolo[4,5-b]pyridinium 3-oxide hexafluoro-phosphate (HATU, 0.24 M, 4 eq) in DMF and DIPEA in NMP (1.0 M, 4 eq). After 40 minutes reaction, the resin was washed three times with DMF (2.1 mL). After each coupling step, except for coupling of the last amino acid, the remaining unreacted amine was capped with $Ac_2O$ prior to Fmoc-deprotection as follows: To the washed resin was added a solution of $Ac_2O$/2,6-lutidine/NMP (5/6/89 v/v, 4 eq). After 10 minutes reaction time, the resin was washed three times with DMF (1.1 mL).

Fmoc-deprotection of the amine was done as follows: To the washed resin was added a solution of piperidine in DMF (40%, 1.2 mL). The reaction was run for 3 minutes. The solvent was emptied and more piperidine in DMF (40%, 0.6 mL) followed by DMF (0.6 mL) were added. After 10 minutes reaction, the resin was washed six times with DMF (1.3 mL).

After coupling of the last amino acid, Fmoc-deprotection was followed by acetylation as described above. Subsequently, a final wash with seven solvents was done as follows: To the washed resin was added solvent (3 mL). After vortexing for 1 minute the reactor was emptied and the next solvent was added. The solvents used were in order: DCM (2×), MeOH, DCM, MeOH (2×) and $Et_2O$. After synthesis the resin was dried under vacuum and stored in the freezer.

Protocol 4: CEM Liberty Blue Synthesiser

The peptides were synthesized in 0.1 or 0.25 mmol scale on a CEM Liberty Blue (automated microwave peptide synthesizer). Agitation was achieved by bubbling nitrogen through the mixture. Solvents, solutions of the amino acids and reagents were kept under $N_2$ atmosphere. The reactions were heated in a microwave single-node cavity under $N_2$ atmosphere.

Swelling of the resin was done in DMF as follows: To the resin was added DMF (15 mL) and the mixture was left for 5 minutes before the reactor was emptied.

Coupling of the amino acid was done with a 4-fold molar excess as follows: To the washed resin (1 eq) was added sequentially a solution of the Fmoc-amino acid in DMF (0.2 M, 4 eq), followed by solution of DIC (0.5 M, 4 eq) and Oxyma in DMF (1 M, 4 eq). The reaction was heated at 90° C. for 4 minutes. Fmoc-Arg-Pbf was coupled twice. The reactor was emptied, and the resin was washed four times with DMF (7 mL).

Fmoc-deprotection of the amine was done as follows: To the washed resin was added a solution of piperidine in DMF (20%, 10 mL). The reaction was heated at 90° C. for 2 minutes. The solvent was emptied and more piperidine in DMF (20%, 10 mL) was added. The reaction was heated at 90° C. for another 2 minutes. The reactor was emptied, and the resin was washed four times with DMF (7 mL).

In cases where N-acetylation was desired, the following procedure was carried out after Fmoc-deprotection: To the washed resin was added a solution of $Ac_2O$ in DMF (5 M, 4 eq) and a solution of DIPEA in DMF (2 M, 2.5 mL for the 10 mL reactor or concentrated, 4 eq for the 30 mL reactor). After 10 minutes reaction, the resin was washed four times with DMF (4.5 mL for the 10 mL reactor or 9 mL for the 30 mL reactor).

A final wash before cleavage was performed as follows: To the washed resin was added DCM (4.5 mL for the 10 mL reactor or 9 mL for the 30 mL reactor) and the reactor was emptied. This procedure was repeated six times before the resin was dried under vacuum and stored in the freezer.

Protocol 5: Cleavage of the Peptide from the Resin

Cleavage and deprotection of the linear peptides from the resin was carried out as follows: A solution of trifluoroacetic acid (TFA)/triisopropylsilane (TIS)/3,6-dioxa-1,8-octanedithiol (DODT)/water (92.5/2.5/2.5/2.5, 90/2.5/2.5/5 or 95/2.5/0/2.5 vol/vol, 5-20 mL) was added to the dried resin. The reaction was vortexed at rt for 2-4 hours. The resin was removed by filtration and washed with DCM (3×10 mL), MeOH (3×10 mL), and again with DCM (3×10 mL). The volume of the combined filtrates was reduced to 10-20 mL, and the peptides were precipitated with ice-cold $Et_2O$ or MTBE (20-40 mL). The mixture was centrifuged, the liquid decanted off, and the sediment resuspended in cold ether, and centifuged again. This process precipitate was repeated two more times.

The peptide was dried under vacuum, or lyophilized from a mixture of MeCN and water and stored in the freezer. Typically, the linear peptides were used without further purification in the TATA cyclization step.

The volume of the filtrate was reduced in vacuo to around 20 ml and the peptide was precipitated by adding a mixture of heptane-MTBE 1:1 v/v (100 ml). After centrifugation, the liquid was decanted and the solid resuspended in a mixture of re-suspended in heptane-MTBE and centrifuge again. The whole process was repeated one more time.

Protocol 6: Cyclization of Linear Peptides with TATA 1,3,5-Triacryloyl-1,3,5-triazinane (TATA, 1 eq), dissolved in MeCN (2-4 mL), and aqueous $NH_4HCO_3$ buffer (0.06 M, pH 7.9, 10-20 mL) were added to a solution of the crude linear peptide (10-200 mg) in a mixture of MeCN (8-16 mL) and water (10-20 mL). The reaction was stirred at rt for 2-24 hours and monitored by LCMS. Typically, the reaction was quenched with $HCO_2H$ (0.5-2 mL), but this step could also be omitted. Subsequently, the mixture was filtered, the filtrate was freeze dried, and the resulting crude product purified by RP-HPLC. After purification the relevant fractions were pooled and lyophilized to yield the desired product.

Several amino acids have been prepared as described below.

Intermediate 1: 4-Chloro-N-{[(9H-fluoren-9-yl)methoxy]carbonyl}-3-fluoro-L-phenylalanine

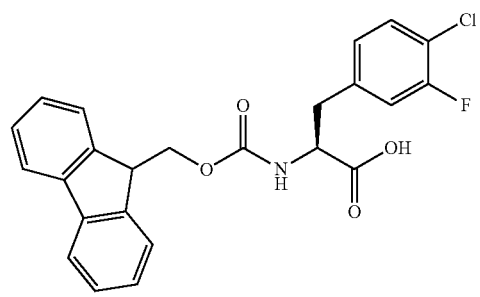 [SMILES: O=C(N[C@@H](Cc1ccc(Cl)c(F)c1)C(=O)O)OCC1c2ccccc2-c2ccccc21]

Step 1: Methyl 4-chloro-N-{[(9H-fluoren-9-yl)methoxy]carbonyl}-3-fluoro-L-phenylalaninate

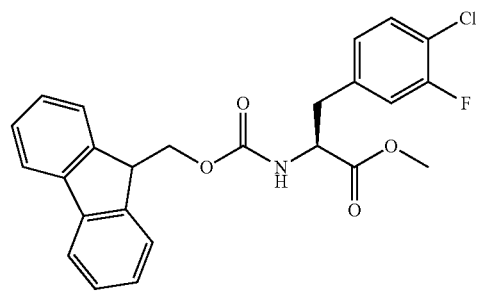 [SMILES: COC(=O)[C@H](Cc1ccc(Cl)c(F)c1)NC(=O)OCC1c2ccccc2-c2ccccc21]

The procedure described by Ross, A. J., Lang, L. H. and Jackson, R. F. W. (J. Org. Chem. 2010, 75, 245-248) was followed. Zinc powder (1.2 g, 18.35 mmol) was activated in 10% HCl for 20 sec and was washed with deminineralized water and methanol and dried in high vacuum over 12 h. The activated zinc was suspended in anhydrous DMF (25 ml). Iodine (30 mg, 0.12 mmol) was added and the resulting mixture was stirred until the brown colour of iodine disappeared. Then methyl N-{[(9H-fluoren-9-yl)methoxy]carbonyl}-3-iodo-L-alaninate (Sigma Aldrich, 2.5 g, 5.54 mmol) in DMF (25 ml) was added, followed by iodine (30 mg). The mixture was stirred for 90 min, then $Pd_2(dba)_3$ (22.9 mg, 0.025 mmol) and S-Phos (19.4 mg, 0.05 mmol) were mixed in abs. DMF (5 ml) and stirred for 5 min, while bubbling nitrogen through the mixture. The resulting solution was added to the organozinc reagent and subsequently 4-chloro-3-fluoro-1-bromobenzene (1.563 g, 6.09 mmol) was added. The mixture was stirred overnight at rt. The reaction mixture was passed through a pad of silica gel (10 g $SiO_2$) eluted with TBME and the filtrate was evaporated under reduced pressure. The residue was purified by chromatography on silica gel using a Biotage Auto flash system (eluent Heptane-EtOAc 0-50%). Fractions containing the product were evaporated to yield the title compound as an amber solid (1.81 g, 72%). LCMS $ES^+$ m/z=454, 456 $[M+H]^+$. $^1$HNMR (400 MHz, DMSO-$d_6$) δ 2.87 (dd, J=13.8, 10.6 Hz, 1H), 3.07 (dd, J=13.7, 4.7 Hz, 1H), 3.63 (s, 3H), 4.19-4.39 (m, 4H), 7.11 (d, J=8.2 Hz, 1H), 7.24-7.53 (m, 6H), 7.61 (d, J=7.4 Hz, 2H), 7.88 (d, J=7.6 Hz, 2H), 7.90 (bs, 1H).

Step 2: 4-Chloro-N-{[(9H-fluoren-9-yl)methoxy]carbonyl}-3-fluoro-L-phenylalanine The methyl ester from step 1 (1.80 g, 3.96 mmol) was dissolved in dioxane (20 ml), the mixture was cooled to 0° C. in an ice bath and then a solution of LiOH (0.211 g, 8.77 mmol) dissolved in water (10 ml) was added dropwise. The resulting mixture was stirred for 30 min at 0° C., acidified with 1N HCl and extracted with EtOAc (3×). The organic phase was dried over $MgSO_4$ and evaporated under reduced pressure to leave the title compound as an oil, which was used without further purification (1.51 g, 78%). LCMS ES$^-$ m/z=438, 440 [M−H]$^-$. $^1$HNMR (400 MHz, DMSO-$d_6$) δ 2.86 (dd, J=13.8, 10.1 Hz, 1H), 3.09 (dd, J=13.7, 4.5 Hz, 1H), 4.07-4.14 (m, 1H), 4.16-4.24 (m, 3H), 7.22-7.34 (m, 4H), 7.48 (dd, J=7.3, 2.0 Hz, 1H), 7.56 (bd, J=7.6 Hz, 1H), 7.62 (d, J=7.5 Hz, 2H), 7.88 (d, J=7.6 Hz, 2H).

Intermediates 2, 3 and 4 were prepared following the procedure described for intermediate 1.

Intermediate 2: (2S)-3-(4-Chloronaphthalen-1-yl)-2-({[(9H-fluoren-9-yl)methoxy]carbonyl}amino)propanoic acid

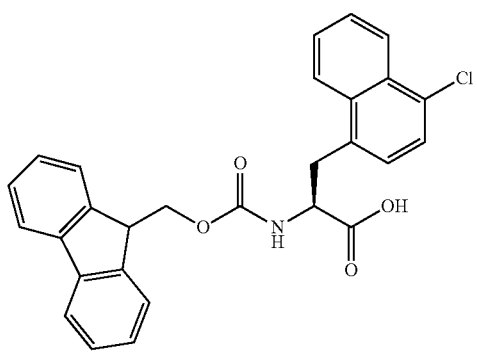 [SMILES: O=C(N[C@@H](Cc1ccc(Cl)c2ccccc12)C(=O)O)OCC1c2ccccc2-c2ccccc21]

Step 1: Methyl (2S)-3-(4-chloronaphthalen-1-yl)-2-({[(9H-fluoren-9-yl)methoxy]carbonyl}amino)propanoate

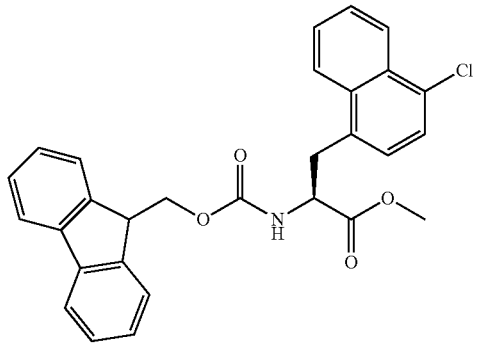 [SMILES: COC(=O)[C@H](Cc1ccc(Cl)c2ccccc12)NC(=O)OCC1c2ccccc2-c2ccccc21]

Scale: 5.56 mmol iodo-L-alaninate; yield: 2.11 g, 78%. LCMS ES$^-$ m/z=486, 488 [M+H]$^+$.

Step 2: (S)-2-((((9H-fluoren-9-yl)methoxy)carbonyl)amino)-3-(4-chloronaphthalen-1-yl)propanoic acid Yield: 1.11 g, 54%. LCMS ES$^-$ m/z=470, 472 [M−H]$^-$. $^1$H NMR (500 MHz, DMSO-$d_6$) δ 3.26 (dd, J=14.2, 10.6 Hz, 1H), 3.66 (dd, J=14.1, 4.1 Hz, 1H), 4.11-4.16 (m, 2H), 4.19 (dd, J=12.5, 9.9 Hz, 1H), 4.29 (td, J=10.5, 4.2 Hz, 1H), 7.25 (td, J=7.5, 0.9 Hz, 1H), 7.30 (td, J=7.4, 0.9 Hz, 1H), 7.37-7.47 (m, 3H), 7.58 (d, J=7.5 Hz, 1H), 7.62 (d, J=7.6 Hz, 2H), 7.69-7.75 (m, 2H), 7.83-7.92 (m, 3H), 8.18-8.26 (m, 2H), 12.93 (s, 1H).

Intermediate 3: 4-Chloro-N-{[(9H-fluoren-9-yl)methoxy]carbonyl}-3,5-difluoro-L-phenylalanine

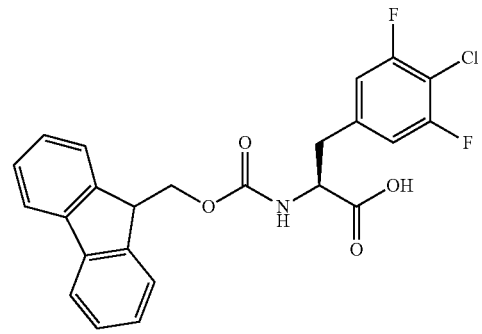 [SMILES: O=C(N[C@@H](Cc1cc(F)c(Cl)c(F)c1)C(=O)O)OCC1c2ccccc2-c2ccccc21]

Step 1: Methyl 4-chloro-N-{[(9H-fluoren-9-yl)methoxy]carbonyl}-3,5-difluoro-L-phenylalaninate

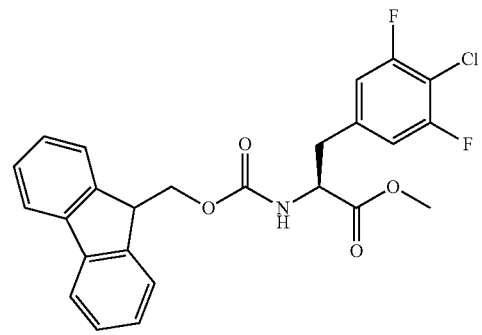 [SMILES: COC(=O)[C@H](Cc1cc(F)c(Cl)c(F)c1)NC(=O)OCC1c2ccccc2-c2ccccc21]

Scale: 2 g, 4.43 mmol iodo-L-alaninate; yield: 0.8 g, 38%. LCMS ES$^+$ m/z=494, 496 [M+Na]$^+$.

Step 2: 4-Chloro-N-{[(9H-fluoren-9-yl)methoxy]carbonyl}-3,5-difluoro-L-phenylalanine Scale: 1.4 g, 2.97 mmol; yield: 500 mg, 36.8%. LCMS ES$^-$ m/z=456, 458 [M−H]$^-$. $^1$H NMR (300 MHz, DMSO) δ 2.89 (dd, J=15.1, 9.5 Hz, 1H), 3.15 (dd, J=13.8, 4.2 Hz, 1H), 4.10-4.32 (m, 4H), 7.21-7.34 (m, 4H), 7.40 (t, J=7.4 Hz, 2H), 7.61 (d, J=7.4 Hz, 2H), 7.76 (d, J=8.6 Hz, 1H), 7.87 (d, J=7.5 Hz, 2H), 12.88 (s, 1H).

Intermediate 4: 3-Chloro-N-{[(9H-fluoren-9-yl)methoxy]carbonyl}-4-fluoro-L-phenylalanine

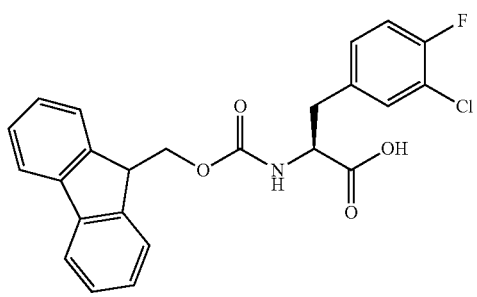

Step 1: Methyl 3-chloro-N-{[(9H-fluoren-9-yl)methoxy]carbonyl}-4-fluoro-L-phenylalaninate

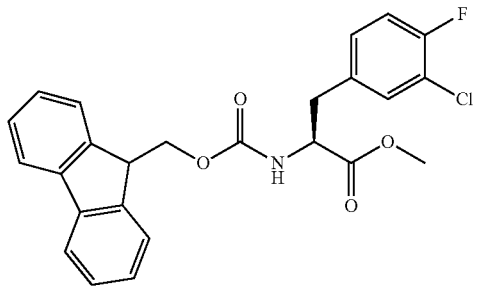

Scale: 24 g, (53.18 mmol) iodo-L-alaninate; yield in 4 batches 6 g each; combined yield: 16.0 g, 66%. LCMS ES$^+$ m/z=476, 478 [M+Na]$^+$. $^1$H NMR (400 MHz, CDCl$_3$) δ 3.04 (dd, J=14.1, 6.0 Hz, 1H), 3.12 (dd, J=14.0, 5.7 Hz, 1H), 3.77 (s, 3H), 4.24 (t, J=6.6 Hz, 1H), 4.36-4.46 (m, 1H), 4.51 (dd, J=10.6, 7.1 Hz, 1H), 4.61-4.71 (m, 1H), 5.33 (d, J=7.9 Hz, 1H), 6.96 (s, 1H), 7.06 (t, J=8.6 Hz, 1H), 7.17 (d, J=6.1 Hz, 1H), 7.31-7.39 (m, 2H), 7.43 (t, J=7.2 Hz, 2H), 7.55-7.66 (m, 2H), 7.80 (d, J=7.5 Hz, 2H).

Step 2: 3-Chloro-N-{[(9H-fluoren-9-yl)methoxy]carbonyl}-4-fluoro-L-phenylalanine Scale: 17.1 g, 37.67 mmol iodo-L-alaninate; yield: 3.0 g, 18%. LCMS ES$^-$ m/z=438, 440 [M−H]$^-$. $^1$H NMR (400 MHz, DMSO-d$_6$) δ 2.86 (dd, J=13.5, 10.4 Hz, 1H), 3.10 (dd, J=13.6, 3.8 Hz, 1H), 3.64 (bs, 4-6H), 4.10-4.24 (m, 4H), 7.22-7.34 (m, 3H), 7.40 (t, J=7.4 Hz, 2H), 7.48 (d, J=6.6 Hz, 1H), 7.54 (d, J=8.1 Hz, 1H), 7.62 (d, J=7.4 Hz, 2H), 7.87 (d, J=7.5 Hz, 2H).

Intermediate 5: 3-Acetamido-4-chloro-N-{[(9H-fluoren-9-yl)methoxy]carbonyl}-L-phenylalanine

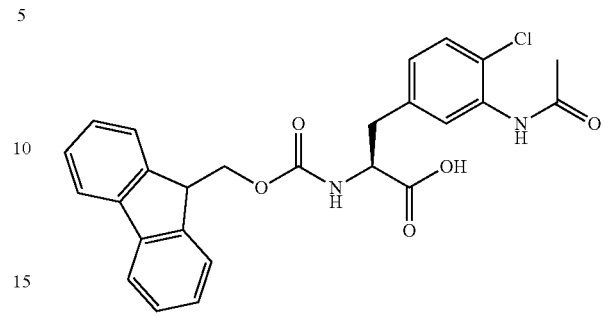

Step 1: Methyl 3-amino-4-chloro-N-{[(9H-fluoren-9-yl)methoxy]carbonyl}-L-phenylalaninate

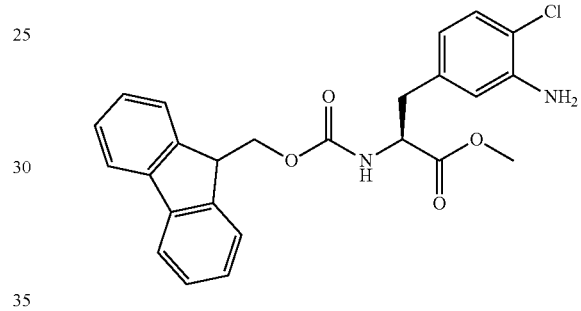

The title compound was prepared as described for intermediate 1 in step 1 from 0.10-2.52 g (0.22-5.58 mmol) of iodo-L-alaninate and 0.549-1.38 g (0.27-6.70 mmol) 5-bromo-2-chloroaniline. Yield: 0.073-0.52 g, 21-73%. LCMS ES$^+$ m/z=451, 453 [M+H]$^+$. $^1$H NMR (500 MHz, DMSO) δ 2.73 (dd, J=13.6, 9.9 Hz, 1H), 2.89 (dd, J=13.6, 5.3 Hz, 1H), 3.62 (s, 3H), 4.16-4.21 (m, 4H), 5.26 (bs, 2H), 6.43 (dd, J=8.1, 1.9 Hz, 1H), 6.66 (d, J=1.9 Hz, 1H), 7.06 (d, J=8.1 Hz, 1H), 7.26-7.36 (m, 2H), 7.38-7.44 (m, 2H), 7.64 (t, J=8.4 Hz, 2H), 7.85 (d, J=8.1 Hz, 1H), 7.88 (d, J=7.6 Hz, 2H).

Step 2: Methyl 3-acetamido-4-chloro-N-{[(9H-fluoren-9-yl)methoxy]carbonyl}-L-phenylalaninate

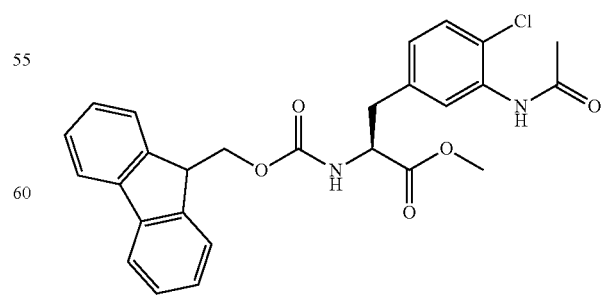

Acetic anhydride (0.105 mL, 1.12 mmol) was added dropwise to a stirred solution of the foregoing product (300 mg, 0.56 mmol) and TEA (0.234 mL, 1.68 mmol) in DCM (3 mL) cooled to 0° C. on an ice bath. The resulting mixture was stirred at rt overnight. The reaction was diluted with DCM and washed with sat. NaHCO$_3$, dried through a phase separator and concentrated under reduced pressure. The residue was purified by automated flash chromatography on a Biotage® KP-SIL 25 g column. A gradient from 6% to 55% of EtOAc in heptane over 10 column volumes (CV), then 55% EtOAc over 5 CV was used as mobile phase. Desired fractions were pooled and concentrated to yield the title compound (177 mg, 64%) as a yellow solid. LCMS ES$^+$ m/z=493, 495 [M+H]$^+$. $^1$H NMR (500 MHz, DMSO) δ 2.06 (s, 3H), 2.88 (dd, J=13.7, 10.0 Hz, 1H), 3.02 (dd, J=13.8, 5.0 Hz, 1H), 3.62 (s, 3H), 4.15-4.28 (m, 4H), 7.01-7.1 (m, 1H), 7.26-7.35 (m, 2H), 7.40 (dt, J=16.0, 7.9 Hz, 3H), 7.59-7.69 (m, 3H), 7.89 (dd, J=7.8, 4.8 Hz, 3H), 9.45 (s, 1H).

Step 3: 3-Acetamido-4-chloro-N-{[(9H-fluoren-9-yl)methoxy]carbonyl}-L-phenylalanine The foregoing compound (137 mg, 0.28 mmol) was dissolved in dioxane (1.60 mL). The resulting solution was cooled with an ice bath, then LiOH (13.31 mg, 0.56 mmol) dissolved in water (0.8 mL) was added dropwise, and the resulting mixture stirred at 0° C. LCMS analysis after 35 min shows complete reaction. The reaction mixture was acidified with HCl (1 M). A precipitate formed, which was isolated by filtration, washed with water and dried overnight under vacuum at 50° C. The title compound (87 mg, 65%) was used without further purification LCMS ES$^+$ m/z=479, 481 [M+H]$^+$. $^1$H NMR (500 MHz, DMSO) δ 2.05 (s, 3H), 2.8-2.92 (m, 1H), 3.05 (dd, J=14.1, 4.2 Hz, 1H), 4.09-4.26 (m, 4H), 7.09 (d, J=7.3 Hz, 1H), 7.26-7.35 (m, 2H), 7.36-7.45 (m, 3H), 7.61-7.7 (m, 3H), 7.75 (d, J=8.5 Hz, 1H), 7.88 (d, J=7.6 Hz, 2H), 9.45 (s, 1H), 12.78 (bs, 1H).

Preparation of 5×4 Bicycles with N-Terminal Acetate or Free Amino Group

Preparation of Example 129

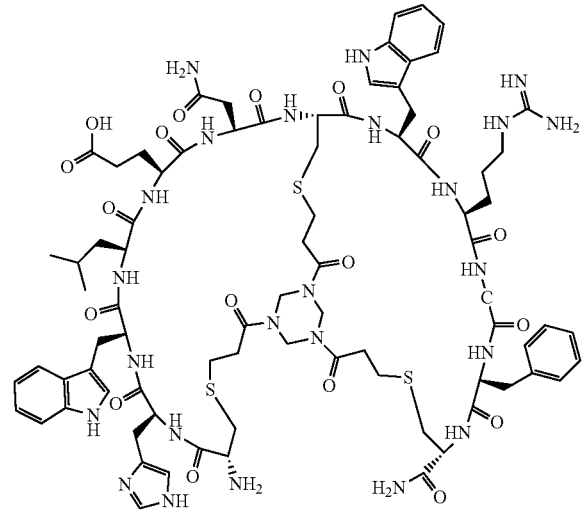 [SMILES: CC(C)C[C@H]1NC(=O)[C@@H](Cc2c[nH]c3ccccc23)NC(=O)[C@H](Cc2c[nH]cn2)NC(=O)[C@@H](N)CSCCC(=O)N2CN3CN(C2)C(=O)CCSC[C@H](NC(=O)[C@@H](CC(N)=O)NC(=O)[C@H](CCC(=O)O)NC1=O)C(=O)N[C@@H](Cc1c[nH]c2ccccc12)C(=O)N[C@@H](CCCNC(=N)N)C(=O)NCC(=O)N[C@H](Cc1ccccc1)C(=O)N[C@H](C(N)=O)CSCCC3=O]

Step 1: Preparation of Cys-His-Trp-Leu-Glu-Asn-Cys-Trp-Arg-Gly-Phe-Cys-NH$_2$ The resin-bound protected peptide was prepared on a 0.25 mmol scale on the Biotage Initiator+ Alstra in a 30 mL reactor vial according to the procedure described in protocol 2, but omitting the final acetylation step. Swelling of the resin was performed in DCM at rt for 30 minutes. After coupling and deprotection of the last amino acid, an amount of resin, equivalent to 0.08 mmol peptide was treated with 10 mL of a mixture of TFA/TIS/Phenol/H$_2$O (10 mL, 88:2:5:5) for 2 h. The crude product was purified by preparative HPLC (Column: Chromasil C8 10 μm 250×20 mm. Mobile phase: A—H$_2$O/MeCN/TFA 95/5/0.1 and B—MeCN; gradient 5-27% B in 5 min, then 27-32% B in 25 min; flow 19 mL/min) to yield the linear peptide (55 mg, 44%). LCMS (Acquity CSH C18 1.7 μm, pH 3, rt 1.10 min, 10 to 90% MeCN in 4 min): ES$^+$ m/z=776.1 [M+2H]$^{2+}$, purity 100%.

Step 2: TATA Cyclization

The foregoing linear peptide (55 mg, 0.03 mmol) was cyclized with TATA for 1.5 hours according to the TATA cyclization procedure. The peptide was purified by preparative HPLC Column: Waters Atlantis T3 ODB 5 μm 150×19 mm; mobile phase: A—H$_2$O/TFA 100/0.15 and B—MeCN with a gradient 5% B for 1 min, 5-22% B in 3 min, 22-27% B in 15 min; flow 30 mL/min at rt, detection 220 nm, injection volume 2 mL, sample concentration 10 mg/mL) to give the title compound (11 mg, 17%). HRMS: calculated for (C$_{81}$H$_{108}$N$_{24}$O$_{18}$S$_3$+2H)$^{2+}$ 901.3796; found (ESI [M+2H]$^{2+}$) 901.3743, purity 97%.

Preparation of Example 252

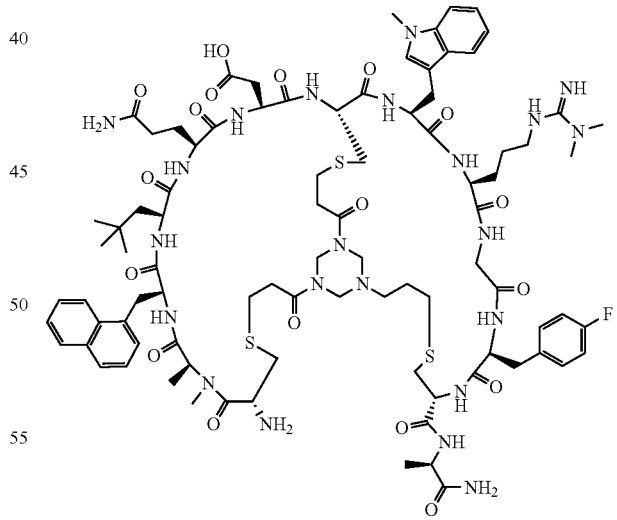

Step 1: Preparation of C-(NMe-Ala)-(1-naphthyl-Ala)-(tBu-Ala)-Q-D-C-(NMe-Trp)-(dimethyl-Arg)-G-(4-F-Phe)-C-a-NH$_2$ The linear peptide was prepared, following the procedure described in Example 1. Scale: 730 mg rink amide resin (0.35 mmol, 0.48 mmol/g). Cleavage and deprotection from the resin was performed with a mixture of TFA (20 mL), water (1.5 mL), TIS (0.8 mL) and 0.8 ml DODT (0.8 mL) over 4 h. The resin was filtered off, washed with DCM (3×10 ml) and MeOH (3×10 ml). The volume of the filtrate was reduced in vacuo to around 20 ml and the peptide was precipitated by adding a mixture of heptane-MTBE 1:1 v/v (100 ml). After centrifugation, the liquid was decanted off and the sediment resuspended in a mixture of heptane-MTBE and centrifuged again. The residue was dissolved in a mixture of MeCN-water 1:1 (ca 100 ml) and lyophilised to give the linear peptide (463 mg, 80%). LCMS (Acquity CSH C18 1.7 μm, pH 3, rt 1.10 min, 10 to 90% MeCN in 4 min): ES$^+$ m/z=830.3 [M+2H]$^{2+}$, purity 82%.

Step 2: TATA Cyclisation

The foregoing linear peptide (463 mg, 0.28 mmol) was dissolved in a mixture of MeCN (95 ml), water (100 ml) and 60 mM NH$_4$HCO$_3$ buffer (60 mM, 100 ml) under nitrogen atmosphere. TATA (69.7 mg, 0.28 mmol), dissolved in MeCN (5 ml) was added portionwise over ca 3 min. The resulting mixture was stirred for 1 h at rt, acidified with formic acid (4 ml) and freeze-dried. The residue was subjected to preparative RP-LC (Column: Chromasil C-18 5×100 cm, mobile phase: A—H$_2$O/TFA (0.2% TFA) and B—MeCN with a gradient of 10%-60% B in 30 min, flow rate 100 ml/min.) to afford the title compound (99 mg, 17%). HRMS: calculated for (C$_{88}$H$_{121}$FN$_{22}$O$_{19}$S$_3$+2H)$^{2+}$ 953.4240; found (ESI [M+2H]$^{2+}$) 953.4250, purity 90%.

Preparation of Example 76

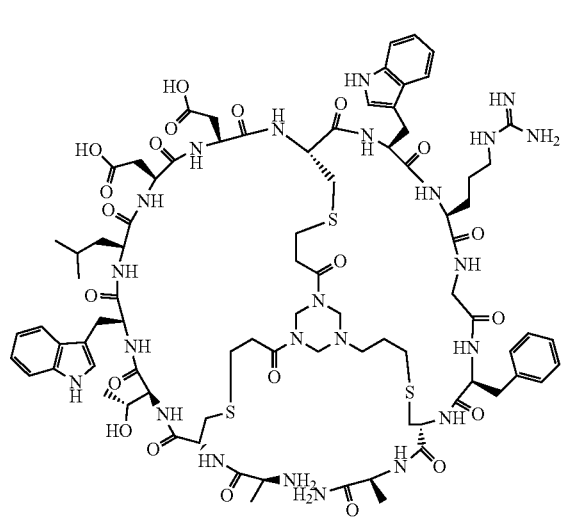 [SMILES: CC(C)C[C@H]1NC(=O)[C@@H](Cc2c[nH]c3ccccc23)NC(=O)[C@H]([C@@H](C)O)NC(=O)[C@@H](NC(=O)[C@H](C)N)CSCCC(=O)N2CN3CCCSC[C@@H](C(=O)N[C@@H](C)C(N)=O)NC(=O)[C@H](Cc4ccccc4)NC(=O)CNC(=O)[C@H](CCCNC(=N)N)NC(=O)[C@H](Cc4c[nH]c5ccccc45)NC(=O)[C@H](CSCCC(=O)N(C3)C2)NC(=O)[C@@H](CC(=O)O)NC(=O)[C@H](CC(=O)O)NC1=O]

Prepared by the method described in protocol 1.
HRMS: calculated for (C$_{87}$H$_{118}$N$_{26}$O$_{20}$S$_3$+2H)$^{2+}$ 947.8953; found (ESI [M+2H]$^{2+}$) 947.8984, purity 82%.

Preparation of Example 5

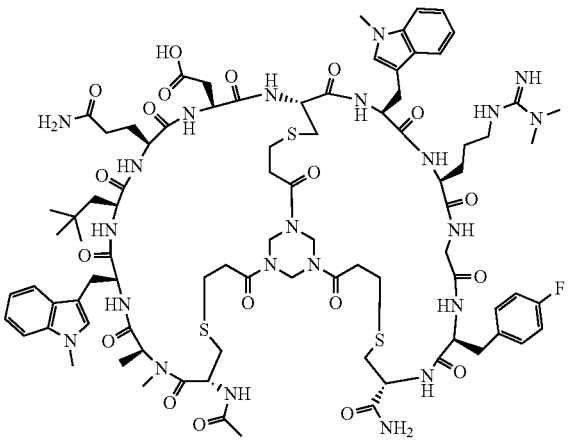 [SMILES: CC(=O)N[C@H]1CSCCC(=O)N2CN3CN(C2)C(=O)CCSC[C@H](NC(=O)[C@@H](CC(=O)O)NC(=O)[C@H](CCC(N)=O)NC(=O)[C@H](CC(C)(C)C)NC(=O)[C@@H](Cc2cn(C)c4ccccc24)NC(=O)[C@H](C)N(C)C1=O)C(=O)N[C@@H](Cc1cn(C)c2ccccc12)C(=O)N[C@@H](CCCNC(=N)N(C)C)C(=O)NCC(=O)N[C@@H](Cc1ccc(F)cc1)C(=O)N[C@H](C(N)=O)CSCCC3=O]

Step 1: Preparation of Ac-Cys-(NMe-Ala)-(NMe-Trp)-(tBu-Ala)-Gln-Asp-Cys-(NMe-Trp)-(dimethyl-Arg)-Gly-(4-F-Phe)-Cys-NH$_2$ Following the procedures laid out in protocol 2 and Example 129, the linear peptide was prepared on a 0.2 mmol scale on the Biotage Initiator+ Alstra to give 215 mg (66%). LCMS (Acquity CSH C18 1.7 μm, pH 3, rt 6.02 min, 20 to 60% MeCN in 10 min): ES$^+$ 819.3 [M+2H]$^{2+}$.

Step 2: TATA Cyclization

Following the procedures laid out in protocol 2 and Example 129, the linear peptide was cyclized to yield the title compound (29 mg, 19%) after purification by preparative HPLC (column: Waters Atlantis T3 ODB 5 μm 150×19 mm; mobile phase: A—H$_2$O/TFA 100/0.15 and B—MeCN with a gradient 5% B for 0.5 min, 5-33% B in 1.5 min, 33-38% B in 14 min; flow 30 mL/min at rt, detection 230 nm). HRMS: calculated for (C$_{86}$H$_{119}$FN$_{22}$O$_{19}$S$_3$+2H)$^{2+}$ 940.4162; found (ESI [M+2H]$^{2+}$) 940.4159, purity 93%.

47

N-Terminal Modifications Other than Acetate

Preparation of Example 84

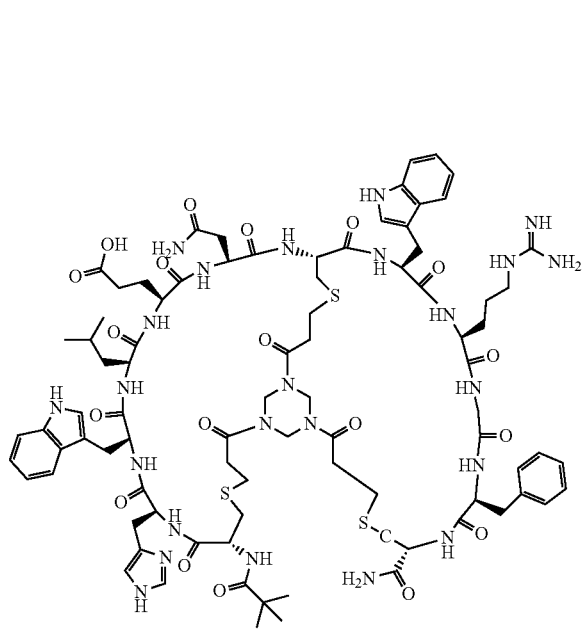 [SMILES: CC(C)C[C@@H]1NC(=O)[C@@H](Cc2c[nH]c3ccccc23)NC(=O)[C@H](Cc2c[nH]cn2)NC(=O)[C@@H](NC(=O)C(C)(C)C)CSCCC(=O)N2CN3CN(C2)C(=O)CCSC[C@H](NC(=O)[C@@H](CC(N)=O)NC(=O)[C@H](CCC(=O)O)NC1=O)C(=O)N[C@@H](Cc1c[nH]c2ccccc12)C(=O)N[C@@H](CCCNC(=N)N)C(=O)NCC(=O)N[C@@H](Cc1ccccc1)C(=O)N[C@H](C(N)=O)CSCCC3=O]

Step 1: Preparation of Piv-Cys-His-Trp-Leu-Glu-Asn-Cys-Trp-Arg-Gly-Phe-Cys-NH$_2$ The Fmoc-protected peptide was prepared in 0.25 mmol scale on the Biotage Initiator+ Alstra in a 30 mL reactor vial according to the procedure described in protocol 2. Swelling of the resin was done with DCM at rt for 20 minutes. The intermediate polymer bound product was stored in a freezer, and an amount equivalent to 0.123 mmol peptide was used to introduce the N-terminal group on the Biotage Initiator+ Alstra. After swelling and Fmoc-deprotection the resin was coupled with pivalic acid (0.3 M, 6 eq), DIC (0.5 M, 6 eq) and oxyma (0.5 M, 6 eq) at 75° C. for 5 minutes. Deprotection and cleavage was achieved by treating the resin for 3 h with 10 mL of TFA/TIS/H$_2$O (92.5:2.5:2) on a shaker. Evaporation of TFA, precipitation with cold Et$_2$O, centrifugation and drying under vacuum gave the title compound as a colourless solid (108 mg, 54%). LCMS (Acquity CSH, C18 1.7 μm, pH 3, rt 2.27 min, 10 to 90% MeCN in 4 min): ES$^+$ m/z=819.3 [M+2H]$^{2+-}$; purity 73%.

Step 2: Cyclization with TATA

The foregoing peptide (108 mg, 0.07 mmol) was cyclized with TATA (16 mg, 0.07 mmol) for 2 hours according to the TATA cyclization procedure. The crude product was purified by preparative HPLC (Column: Waters Atlantis T3 ODB 5 μm 150×19 mm. Mobile phase: A—H$_2$O/TFA 100/0.15 and B—MeCN; gradient: 5% B for 1 min, 5-23% B in 3 min, 23-28% B in 15 min; flow 30 mL/min at rt, detection 230 nm, injection volume 0.6 mL, sample concentration 50 mg/mL) to give the title compound as a colourless solid (14 mg, 11%). HRMS: calculated for (C$_{86}$H$_{116}$N$_{24}$O$_{19}$S$_3$+2H)$^{2+}$ 943.4083; found (ESI [M+2H]$^{2+}$) 943.3998, purity 96%.

48

Preparation of Example 93

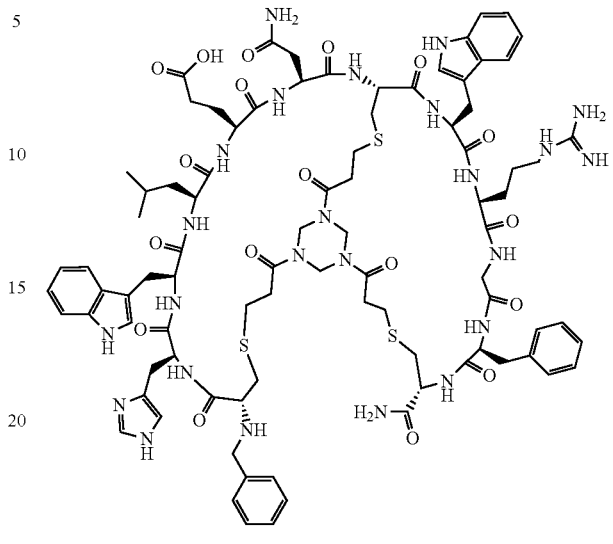

Step 1: Preparation of Bn-Cys-His-Trp-Leu-Glu-Asn-Cys-Trp-Arg-Gly-Phe-Cys-NH$_2$ The resin-bound protected peptide was prepared in 0.25 mmol scale on the Biotage Initiator+ Alstra in a 30 mL reactor vial according to protocol 2, omitting the final acetylation step, to give the intermediate with a free N-terminal amino group. An amount of the resin, equivalent to 0.1 mmol peptide, was used to introduce the benzyl group. After swelling and filtration of the resin, DCM (10 mL) was added followed by benzaldehyde (0.104 mL, 1.00 mmol) and sodium triacetoxyhydroborate (0.218 g, 1.00 mmol). The vial was sealed and shaken at rt for 15 hours. The resulting resin was washed with MeOH (3×) and DCM (3×), and then dried in vacuo at rt for 2 hours. Deprotection and cleavage was achieved by treating the resin for 2 h with 20 mL of TFA/TIS/Phenol (w/v)/H$_2$O 88:2:5:5) with nitrogen bubbling through the mixture. After evaporation of TFA, precipitation with cold Et$_2$O, centrifugation and drying under vacuum, the title compound was obtained as a colourless solid (127 mg, 77%). LCMS (Acquity CSH, C18 1.7 μm, pH 3, RT 5.19 min, 3 to 60% MeCN in 10 min): ES$^+$ m/z=822.2 [M+2H]$^{2+}$, purity 75%.

Step 2: Cyclization with TATA

The foregoing peptide (127 mg, 0.06 mmol) was cyclized with TATA for 2 hours according to the TATA cyclization procedure. The crude product was purified by preparative HPLC (Column: XBridge 5 μm 150×19 mm; Mobile phase: A—H$_2$O/MeCN/NH$_3$ 95/5/0.2 and B—MeCN; gradient 5% B for 1 min, 5-28% B in 3 min, 28-33% B in 15 min; flow 30 mL/min at rt, detection 230 nm) to give the title compound (14 mg, 13%). HRMS: calculated for (C$_{88}$H$_{114}$N$_{24}$O$_{18}$S$_3$+2H)$^{2+}$ 946.4031; found (ESI [M+2H]$^{2+}$) 946.3397, purity 93%.

Compounds in Table 2 were prepared according to the procedures described above for Examples 84 and 93.

TABLE 2

N-terminally Modified 5×4 Bicycles RCys-His-Trp-Leu-Glu-Asn-Cys-Trp-Arg-Gly-Phe-Cys-NH₂

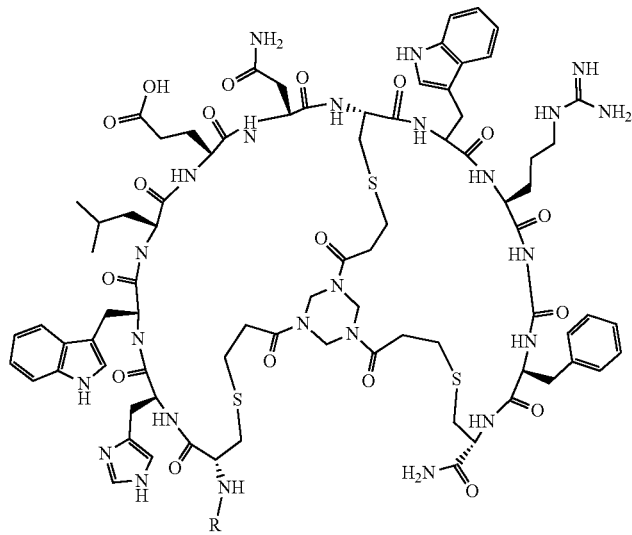

| Example Number | N-terminal group (R) | Mw | HRMS calc. for [M + 2H]²⁺ | HRMS found [M + 2H]²⁺ | Purity (%) |
|---|---|---|---|---|---|
| 89 | 1,4-pyriclazinylC=O | 1908.2 | 954.3879 | 954.3841 | 97 |
| 95 | H₂N(CH₂CH₂O)₃(CH₂)₂HNCO(CH₂)₂C=O | 2104.4 | 1052.4717 | 1052.4629 | 96 |
| 99 | H₂N(CH₂CH₂O)₃CH₂C=O | 1991.3 | 995.9296 | 995.9236 | 93 |
| 103 | H₃CO(CH₂CH₂O)₂CH₂C=O | 1962.2 | 981.4164 | 981.4089 | 96 |
| 116 | PhC=O | 1906.2 | 953.3927 | 953.3890 | 97 |
| 121 | HO₂CCH₂CH₂C=O | 1902.1 | 951.3876 | 951.3851 | 97 |
| 137 | CH₃(CH₂)₈C=O | 1956.3 | 978.4474 | 978.4454 | 97 |
| 139 | CH₃(CH₂)₄C=O | 1900.2 | 950.4162 | 950.4092 | 90 |

Preparation of Example 15

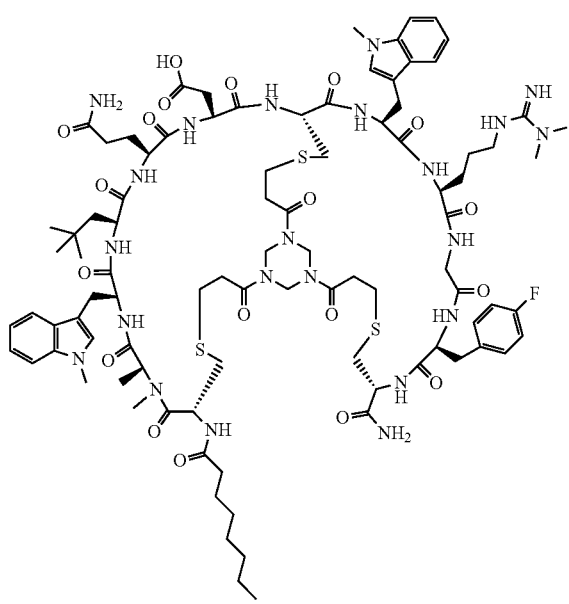 [SMILES: CCCCCCCC(=O)N[C@H]1CSCCC(=O)N2CN3CN(C2)C(=O)CCSC[C@H](NC(=O)[C@@H](CC(=O)O)NC(=O)[C@H](CCC(N)=O)NC(=O)[C@@H](CC(C)(C)C)NC(=O)[C@@H](Cc2cn(C)c4ccccc24)NC(=O)[C@@H](C)N(C)C1=O)C(=O)N[C@@H](Cc1cn(C)c2ccccc12)C(=O)N[C@@H](CCCNC(=N)N(C)C)C(=O)NCC(=O)N[C@@H](Cc1ccc(F)cc1)C(=O)N[C@H](C(N)=O)CSCCC3=O]

Step 1: Preparation of n-octanoyl-Cys-NMeAla-1MeW-Ala(tBu)-Gln-Asp-Cys-1MeW-ADMA-Gly-4Fphe-Cys-NH₂

The Fmoc-protected peptide was prepared in 0.2 mmol scale on Biotage Initiator+ Alstra in a 30 mL reactor vial according protocol 2. Swelling of the resin was done in DMF at 70° C. for 20 minutes. The intermediate polymer bound product was stored in a freezer. Of this an amount equivalent to 0.1 mmol peptide was taken out. The introduction of the N-terminal group was done on CEM Liberty Blue in the following manner: After swelling and Fmoc-deprotection the resin was coupled with octanoic acid (58 mg, 4 eq), DIC and oxyma at 90° C. for 4 minutes. The peptide was deprotected and cleaved from the resin with 10 mL of a mixture of TFA/TIS/H₂O 92.5:2.5:2.5 for 3 hours on a shaker. The title compound obtained (110 mg, 64%) was found to be a colorless solid, which was used directly in the next step. LCMS (Acquity CSH C18 1.7 μm, pH 3, rt 8.73 min, 20 to 60% MeCN in 10 min): ES⁺ m/z=858.4, [M+2H]²⁺, purity 71%.

Step 2: Cyclization with TATA

The foregoing compound (110 mg, 0.05 mmol) was cyclized with TATA for 3 hours according to the TATA cyclization procedure. The peptide was purified by preparative HPLC (Column: Waters XSelect CSH Fluoro Phenyl 5 μm 150×19 mm; mobile phase: A—H₂O/TFA 100/0.15 and B—MeCN with a gradient 5% B for 0.5 min, 5-35% B in 1.5 min, 35-40% B in 14 min. Flow 30 mL/min at rt). to give the title compound obtained (13 mg, 14%) after lyophilization. HRMS: calculated for $(C_{92}H_{131}FN_{22}O_{19}S_3+2H)^{2+}$ 946.4031; found (ESI $[M+2H]^{2+}$) 946.3397, purity 93%.

Compounds in Table 3 were prepared according to the procedure described in example 15.

TABLE 3

N-terminally modified 5×4 Bicycles R-C-Q-(NMe-Trp)-(tBu-Ala)-E-D-C-(NMe-Trp)-(dimethyl-Arg)-G-(4-F-Phe)-C-NH₂

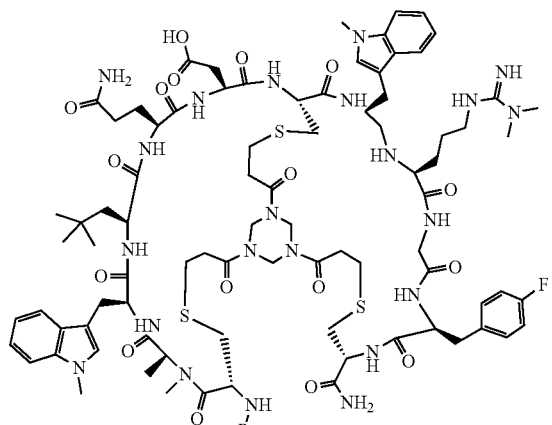

| Example Number | N-terminal group (R) | Mw | MS found [M + 2H]²⁺ | Purity (%) |
|---|---|---|---|---|
| 6 | Pv | 1966.3 | 984.2 | 90 |
| 7 | 1,4-pyridazinylC=O | 1988.3 | 995.2 | 98 |

C-Terminal Modifications of 5×4 Bicycles

Preparation of Example 96

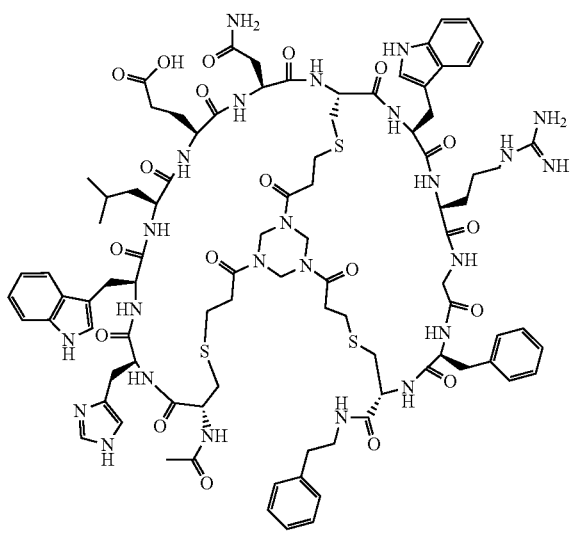 [SMILES: CC(=O)N[C@H]1CSCCC(=O)N2CN3CN(C2)C(=O)CCSC[C@H](NC(=O)[C@H](CC(N)=O)NC(=O)[C@H](CCC(=O)O)NC(=O)[C@H](CC(C)C)NC(=O)[C@H](Cc2c[nH]c4ccccc24)NC(=O)[C@H](Cc2c[nH]cn2)NC1=O)C(=O)N[C@@H](Cc1c[nH]c2ccccc12)C(=O)N[C@H](CCCNC(=N)N)C(=O)NCC(=O)N[C@@H](Cc1ccccc1)C(=O)N[C@H](C(=O)NCCc1ccccc1)CSCCC3=O]

Step 1: Preparation of the Resin

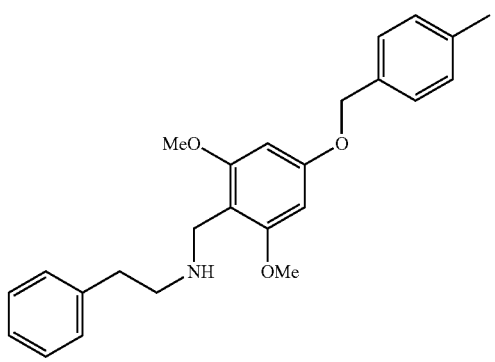 [SMILES: COc1cc(OCc2ccc(C)cc2)cc(OC)c1CNCCc1ccccc1]

4-((4-Phenyl)methoxy)-2,6-dimethoxybenzaldehyde polystyrene resin (1 g, 1-1.5 mmol loading per g, ABCR®) was swollen in dichloroethane (10 ml) for 20 min, then 2-phenylethan-1-amine (0.485 g, 4.00 mmol) was added in 10 ml of dichloroethane, and the resulting mixture was shaken for 30 minutes. Sodium triacetoxyborohydride (1.696 g, 8.00 mmol) was added to the mixture and shaking was continued overnight. The resin was isolated by filtration, washed with DCM (3×10 ml), MeOH+containing 5% TEA (5×10 ml) and MeOH (3×10 ml) and finally dried under vacuum.

Step 2: Loading of Fmoc-Cys(Tr)

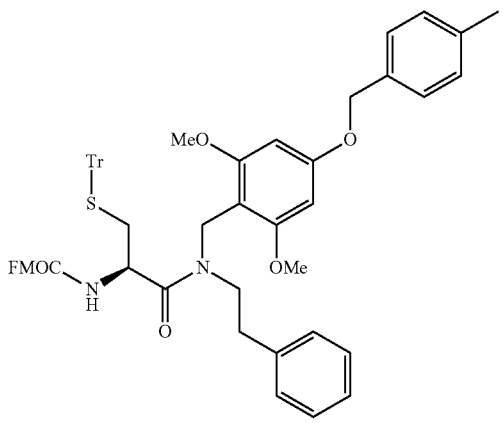

N-(((9H-Fluoren-9-yl)methoxy)carbonyl)-S-trityl-L-cysteine (3.51 g, 6.0 mmol) was dissolved in anhydrous DCM (50 ml). DIPEA (1.1 ml, 6.30 mmol) and fluoro-N,N,N',N-tetramethylformamidinium hexafluorophosphate (1.6 g, 6.06 mmol) were added, and the mixture was stirred under nitrogen for 3 h to generate the corresponding amino acid fluoride. To this mixture was added the resin prepared in step 1 (1.2 g, corresponding to ca. 1.5 mmol), followed by DIPEA (1.1 ml, 6.3 mmol). The mixture was shaken for 160 min, then the resin was isolated by filtration, washed with DCM (2×20 ml), MeOH (5×20 ml) and DCM (3×20 ml).

After drying in vacuo, 52 mg of the resin was treated with TFA (1 ml) containing TES (0.1 mL) for 1 h. Filtration and washing of the resin with DCM (3×1 ml) and MeOH (3×1 ml), yielded a filtrate, which was evaporated to dryness to yield crude Fmoc-Cysteine phenylethylamide (14 mg, Mw=446.6 Da; resin loading calculated 0.6 mmol/g). LCMS ES+ m/z=447.5 [M+H]+.

Step 3: Preparation of Ac-Cys-His-Trp-Leu-Glu-Asn-Cys-Trp-Arg-Gly-Phe-Cys-NHCH$_2$CH$_2$Ph The foregoing resin (0.7 g, 0.42 mmol) was used on the Biotage Initiator+ Alstra in a 30 mL reactor vial according to protocol 2 to synthesise the title compound. After cleavage from the resin, 199 mg (17%) of a colourless powder were obtained, which were used without further purification. LCMS (Acquity CSH, C18 1.7 µm, pH 3, RT 2.09 min, 20 to 60% MeCN in 4 min), ES+ m/z=850.1 [M+2H]$^{2+}$, purity 47%.

Step 4: Cyclization with TATA

The foregoing peptide (85 mg, 0.05 mmol) was cyclized with TATA for 2 hours according to the TATA cyclization procedure. The crude product was purified by preparative HPLC (Column: XBridge 5 µm, 150×19 mm; Mobile phase: A—H$_2$O/MeCN/NH$_3$ 95/5/0.2 and B—MeCN; gradient 5% B for 0.5 min, 5-29% B in 1.5 min, 29-34% B in 14 min; flow 30 mL/min at rt, detection 230 nm) to give the title compound (6 mg, 6%). HRMS: calculated for (C$_{91}$H$_{118}$N$_{24}$O$_{19}$S$_3$+2H)$^{2+}$ 974.4162; found (ESI [M+2H]$^{2+}$) 974.4167, purity 97%.

Preparation of Example 123 Using Chlorotrityl Resin

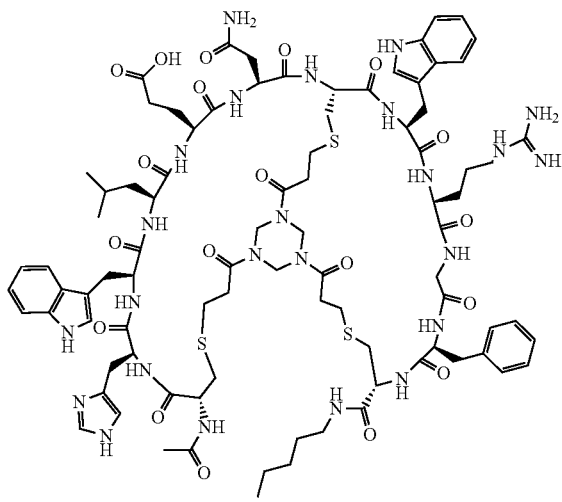 [SMILES: CCCCCNC(=O)[C@@H]1CSCCC(=O)N2CN3CN(C2)C(=O)CCSC[C@H](NC(=O)[C@H](CC(N)=O)NC(=O)[C@H](CCC(=O)O)NC(=O)[C@H](CC(C)C)NC(=O)[C@H](Cc2c[nH]c4ccccc24)NC(=O)[C@H](Cc2c[nH]cn2)NC(=O)[C@@H](NC(C)=O)CSCCC3=O)C(=O)N[C@@H](Cc2c[nH]c3ccccc23)C(=O)N[C@H](CCCNC(=N)N)C(=O)NCC(=O)N[C@@H](Cc2ccccc2)C(=O)N1]

Step 1: 9H-Fluoren-9-ylmethyl N-[(1R)-2-oxo-2-(pentylamino)-1-(tritylsulfanylmethyl)ethyl]carbamate

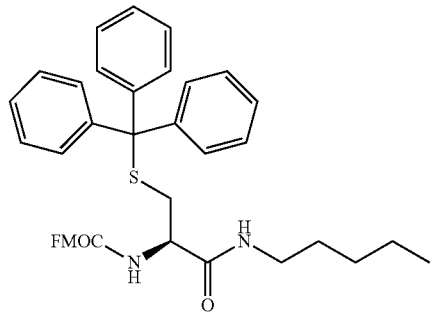

N-(((9H-Fluoren-9-yl)methoxy)carbonyl)-S-trityl-L-cysteine (3 g, 5.12 mmol) was dissolved in anhydrous DCM (50 ml). DIPEA (0.984 mL, 5.63 mmol) and fluoro-N,N,N',N'-tetramethylformamidinium hexafluorophosphate (1.488 g, 5.63 mmol) were added and the mixture was stirred for 1 h at rt. Then DIPEA (0.984 mL, 5.63 mmol) and pentan-1-amine (0.66 mL, 5.63 mmol) were added and the resulting mixture was stirred for 1 h at rt. The reaction mixture was diluted with DCM (50 ml) and washed with 5% citric acid (25 ml). The phases were separated, the aqueous phase was reextracted with DCM, and the combined organic phases were dried over MgSO$_4$. Evaporation gave the title compound (3.21 g, 96%), which was used without further purification.

Step 2: 9H-Fluoren-9-ylmethyl N-[(1R)-2-oxo-2-(pentylamino)-1-(sulfanylmethyl)ethyl]carbamate

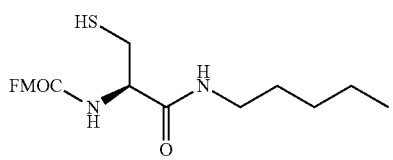

The compound from step 1 (3.21 g, 4.9 mmol) was treated with a solution of 50% TFA in DCM (20 ml), containing TES (1.1 ml) for 2 h. The volatiles were removed in vacuo and the remaining oil was purified by flash chromatography on a Biotage® KP-SIL (340 g column, heptane-EtOAc 0-60%). Fractions containing the desired product were pooled and evaporated to yield the title compound as a foam (1.69 g, 84%). LCMS ES+ m/z=413.6 [M+H]+. $^1$H NMR (500 MHz, CD$_2$Cl$_2$) δ 0.89 (t, J=7.4 Hz, 3H), 1.11-1.18 (m, 1H), 1.32-1.42 (m, 1H), 1.45-1.60 (m, 5H), 2.66-2.79 (m, 1H), 2.99-3.11 (m, 2H), 3.14-3.22 (m, 1H), 4.24 (t, J=6.6 Hz, 1H), 4.25-4.33 (m, 1H), 4.36-4.40 (m, 2H), 5.63, (bs, 1H), 6.12 (bs, 1H), 7.33 (t, J=7.5 Hz, 2H), 7.41 (t, J=7.4 Hz, 2H), 7.61 (d, J=7.5 Hz, 2H), 7.79 (d, J=7.6 Hz, 2H).

Step 3: Preparation of the Resin

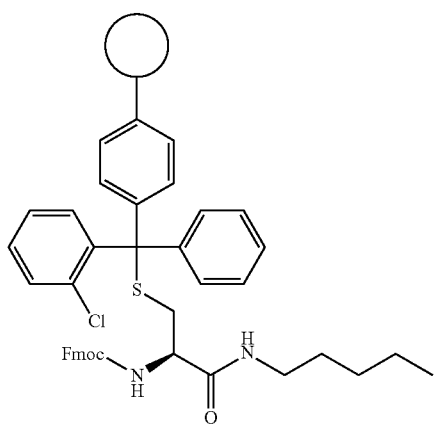

The foregoing compound (1.69 g, 4.1 mmol) was dissolved in anhydrous DCM (30 mL), chlorotrityl chloride resin (Novabiochem®, 1 g, 1.9 mmol/g) and TEA (0.7 ml) were added and the mixture was shaken overnight at rt. The resin was washed with DCM (3×20 ml), MeOH (3×20 ml) and DCM again (3×20 mL) and dried in vacuo. 41 mg of the resin was treated with TFA (1 ml) containing TES (0.1 mL) for 1 h. Filtration and washing of the resin with DCM (3×1 ml) and MeOH (3×1 ml) yielded a filtrate, which was evaporated to dryness to yield 8.1 mg of 9H-fluoren-9-ylmethyl N-[(1R)-2-oxo-2-(pentylamino)-1-(sulfanylmethyl)ethyl]carbamate, corresponding to a resin load of about 0.50 mmol/g.

Step 4: Preparation of Ac-Cys-His-Trp-Leu-Glu-Asn-Cys-Trp-Arg-Gly-Phe-Cys-NH(CH$_2$)$_4$CH$_3$ The foregoing resin (1.0 g, 0.5 mmol) was used on the Biotage Initiator+ Alstra in a 30 mL reactor vial according to protocol 2 to synthesise the title compound. After cleavage from the resin the linear peptide (312 mg, 37%) was obtained, which was used without further purification. LCMS (Acquity CSH, C18 1.7 μm, pH 3, RT 2.06 min, 20 to 60% MeCN in 4 min): ES$^+$ m/z=833.1 [M+2H]$^{2+}$, purity 68%.

Step 5: Cyclization with TATA

The foregoing peptide (103 mg, 0.06 mmol) was cyclized with TATA for 2 hours according to the TATA cyclization procedure. The crude product was purified by preparative HPLC (Column: XBridge 5 μm, 150×19 mm; Mobile phase: A—H$_2$O/TFA 95/5 and B—MeCN; gradient 5% B for 0.5 min, 5-29% B in 1.5 min, 29-34% B in 14 min; flow 30 mL/min at rt, detection 230 nm) to give the title compound as a colourless solid (19 mg, 15%). HRMS: calculated for (C$_{88}$H$_{120}$N$_{24}$O$_{19}$S$_3$+2H)$^{2+}$ 957.4240; found (ESI [M+2H]$^{2+}$) 957.4255, purity 95%.

The peptides in Table 4 were synthesised using procedures similar to the ones described for Examples 96 and 123

TABLE 4

C-terminal modified 5×4 Bicycles AcCHWLENCWRGFC-NHZ

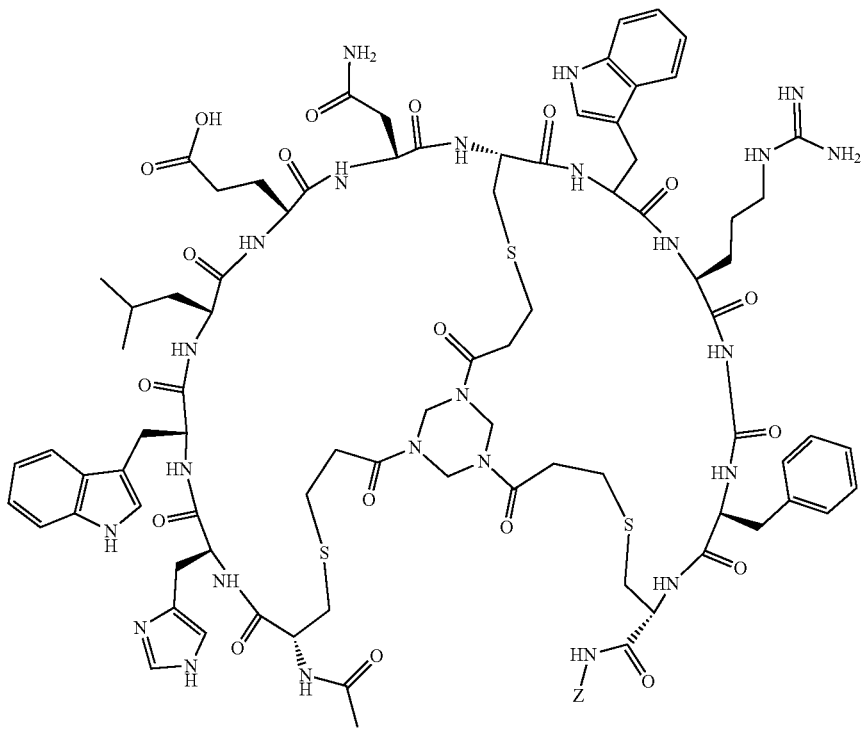

TABLE 4-continued

| Example Number | C-terminal group (Z) | Mw | HRMS calc. for $[M + 2H]^{2+}$ | HRMS found $[M + 2H]^{2+}$ | Purity (%) |
| --- | --- | --- | --- | --- | --- |
| 96 | $PhCH_2CH_2$— | 1948.3 | 974.4162 | 974.4167 | 97 |
| 109 | Bn | 1934.2 | 967.4083 | 967.4025 | 89 |
| 120 | 3-Pyridyl-$CH_2$— | 1935.2 | — | — | — |
| 122 | n-octyl- | 1956.3 | 978.4474 | 978.4383 | 81 |
| 123 | n-pentyl- | 1914.2 | 957.4240 | 957.4255 | 95 |
| 127 | $CH_3(OCH_2CH_2)_2$— | 1946.2 | 973.4189 | 973.4157 | 97 |

Multimerisation of 5×4 Bicyclic Peptides

Preparation of Example 250

The structure of the compound of Example 250 is depicted in FIG. 1.

Step 1: Ethyl $N^2,N^6$-dipent-4-ynoyl-L-lysinate

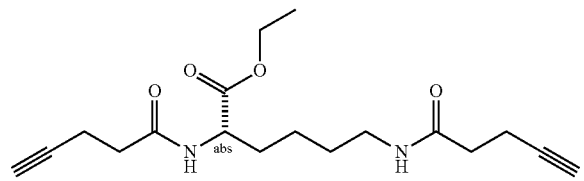 [SMILES: C#CCCC(=O)NCCCC[C@H](NC(=O)CCC#C)C(=O)OCC]

To a suspension of ethyl L-lysinate dihydrochloride (650 mg, 2.63 mmol), was added HATU (2.5 g, 6.57 mmol), pent-4-ynoic acid (645 mg, 6.57 mmol) and $Et_3N$ (1.823 mL, 13.15 mmol) in DCM (25 mL). The reaction was stirred at rt overnight. The reaction was quenched with aqueous $NaHCO_3$ (8%, 25 mL) and the aqueous phase was extracted with DCM (3×25 mL). The organic phases were pooled, washed with $H_3PO_4$ (1 M, 25 mL) and brine (25 mL), dried ($MgSO_4$), filtered and evaporated. The residue was purified by automated flash chromatography on a Biotage® KP-SIL 50 g column. A gradient from 40% to 100% of EtOAc in heptane over 10 CV was used as mobile phase to give the title compound (1.05 g, 119%), containing some impurities, as a colourless oil, which solidified slowly upon standing. $^1$H NMR (500 MHz, DMSO) δ 1.17 (t, J=7.1 Hz, 3H), 1.21-1.44 (m, 4H), 1.52-1.61 (m, 1H), 1.62-1.70 (m, 1H), 2.22-2.27 (m, 2H), 2.341-2.37 (m, 6H), 2.75 (t, J=2.4 Hz, 1H), 2.77 (t, J=2.6 Hz, 1H), 3.01 (q, J=6.7 Hz, 2H), 4.06 (q, J=7.1 Hz, 2H), 4.17 (ddd, J=9.0, 7.6, 5.2 Hz, 1H), 7.86 (t, J=5.5 Hz, 1H), 8.25 (d, J=7.5 Hz, 1H).

Step 2: $N^2,N^6$-Dipent-4-ynoyl-L-lysine

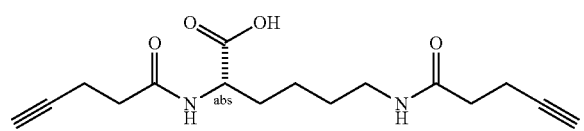 [SMILES: C#CCCC(=O)NCCCC[C@H](NC(=O)CCC#C)C(=O)O]

NaOH(aq) (4.0 M, 1.314 mL, 5.26 mmol) was added to a solution of ethyl $N^2,N^6$-dipent-4-ynoyl-L-lysinate (879 mg, 2.63 mmol) in 1,4-dioxane (10 mL)/water (10 mL). The reaction was stirred for 4.5 hours at rt. Then $H_2O$ (30 mL) was added and the aqueous phase was washed with $Et_2O$ (2×25 mL). The aqueous phase was acidified with $H_3PO_4$ to pH 1, some NaCl was added to it, and extracted with DCM (8×20 mL). The organic phases were pooled, dried ($Na_2SO_4$), filtered and evaporated to obtain the title compound (618 mg, 77%) as a colourless oil. $^1$H NMR (500 MHz, DMSO) δ 1.22-1.43 (m, 4H), 1.48-1.60 (m, 1H), 1.62-1.75 (m, 1H), 2.24 (t, J=7.2 Hz, 2H), 2.27-2.39 (m, 6H), 2.74 (t, J=2.6 Hz, 1H), 2.75-2.77 (m, 1H), 3.01 (d, J=6.4 Hz, 2H), 4.15 (ddd, J=9.0, 8.0, 4.9 Hz, 1H), 7.86 (t, J=5.5 Hz, 1H), 8.14 (d, J=7.9 Hz, 1H), 12.53 (s, 1H).

Step 3: N-But-3-yn-1-yl-$N^2,N^6$-dipent-4-ynoyl-L-lysinamide

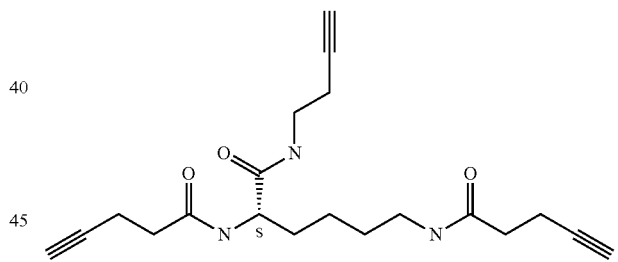

HATU (920 mg, 2.42 mmol) was added to a suspension of $N^2,N^6$-dipent-4-ynoyl-L-lysine (618 mg, 2.02 mmol), but-3-yn-1-aminium chloride (319 mg, 3.03 mmol) and $Et_3N$ (0.559 mL, 4.03 mmol) in a mixture of DMF and DCM (5 and 10 mL). The reaction was stirred at rt for 18 hours. The reaction was quenched with an aqueous solution of $Na_2CO_3$ (10%, 25 mL) and the aqueous phase was extracted with DCM (3×25 mL). The organic phases were pooled, washed with aqueous $H_3PO_4$ (1 M, 25 mL), dried ($MgSO_4$), filtered and evaporated. The residue was purified by automated flash chromatography on a Biotage® KP-SIL 50 g column. A gradient from 0% to 10% of MeOH in EtOAc over 10 CV was used as mobile phase to give the title compound (799 mg, 111%), which was used without further purification. A small sample was purified by RP-HPLC to obtain the spectroscopic data. LCMS ES$^+$ m/z=358.2 $[M+H]^+$. $^1$H NMR (500 MHz, DMSO) δ 1.18-1.3 (m, 2H), 1.32-1.4 (m, 2H), 1.42-1.51 (m, 1H), 1.56-1.65 (m, 1H), 2.25 (dt, J=14.7, 6.6 Hz, 3H), 2.31-2.4 (m, 6H), 2.74 (t, J=2.6 Hz, 1H), 2.74-2.76 (m, 1H), 2.81 (t, J=2.5 Hz, 1H), 2.95-3.06 (m, 3H), 3.07-3.16 (m, 1H), 3.16-3.24 (m, 1H), 4.12-4.23 (m, 1H), 7.82 (t, J=5.3 Hz, 1H), 7.99 (d, J=8.1 Hz, 1H), 8.02 (t, J=5.7 Hz, 1H).

Step 4: Preparation of the Linear Peptide $N_3CH_2C(O)NH(CH_2CH_2O)_3CH_2CH_2(CO)$-Cys-NMeAla-1MeW-Ala(tBu)-Gln-Asp-Cys-1MeW-ADMA-Gly-4Fphe-Cys-NH$_2$ The peptide was prepared in 0.2 mmol scale on Biotage Initiator+ Alstra in a 30 mL reactor vial according to protocol 2. Swelling of the resin was done in DMF at 70° C. for 20 minutes. The last two couplings (Fmoc-NH-PEG3-CH$_2$CH$_2$COOH followed by N$_3$CH$_2$COOH) were conducted at rt for 60 minutes. After cleavage from the resin using 20 mL of a mixture of TFA/TIS/DODT/H$_2$O 92.5:2.5:2.5:2.5 for 2 hours, the title compound (263 mg, 70%) was obtained as a colorless solid and used without further purification and found to be a white solid. LCMS (Acquity CSH C18 1.7 μm, pH 3, rt 6.32 min, 20 to 60% MeCN in 10 min): ES$^+$ m/z=938.4 [M+2H]$^{2+}$, purity 82%.

Step 5: TATA Cyclization

Figure 2:
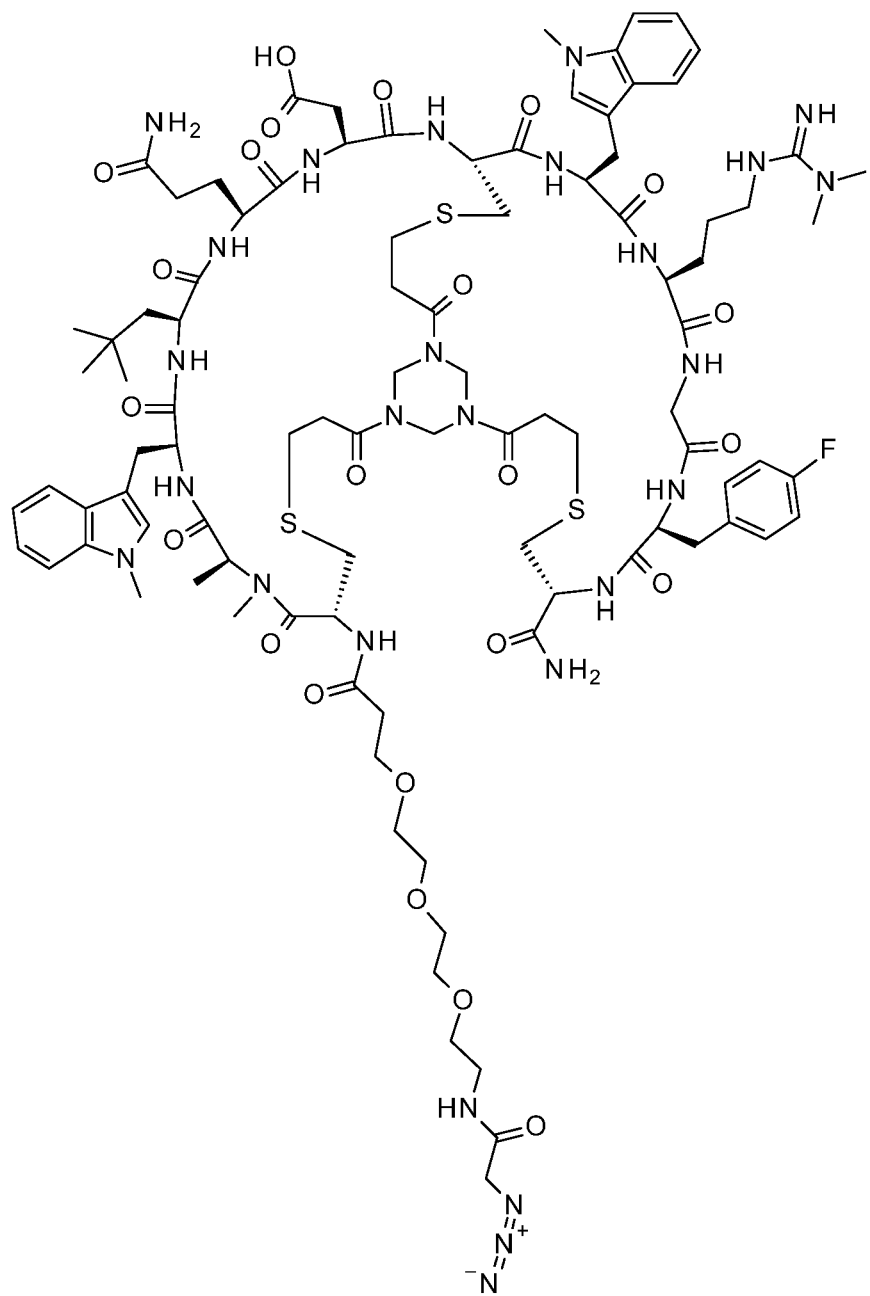
FIG. 2 depicts the structure of the TATA-cyclized intermediate of Example 250.

The structure of TATA-cyclized intermediate is depicted in FIG. 2.

The foregoing linear peptide (263 mg, 0.12 mmol) was cyclized with TATA for 2 days according to the TATA cyclization procedure. The peptide was purified by preparative HPLC (Column: Waters Atlantis T3 ODB 5 μm 150×19 mm; mobile phase: A—H$_2$O/TFA 100/0.15 and B—MeCN with a gradient 5% B for 0.5 min, 5-34% B in 1.5 min, 34-39% B in 14 min; flow 30 mL/min at rt, detection 230 nm, injection volume 1 mL) to give the title compound (30 mg, 12%). HRMS: calculated for $(C_{95}H_{135}FN_{26}O_{23}S_3+2H)^{2+}$ 1062.4747; found (ESI [M+2H]$^{2+}$) 1062.4716, purity 98%.

Step 6: Preparation of Example 250

The structure of the compound of Example 250 is depicted in FIG. 1.

(+)-Sodium L-ascorbate (4.7 mg, 0.02 mmol) was added to a solution of the foregoing compound (25 mg, 0.01 mmol), N-but-3-yn-1-yl-N$^2$,N$^6$-dipent-4-ynoyl-L-lysinamide (2.103 mg, 5.88 μmol) and CuSO$_4$.5H$_2$O (5.88 mg, 0.02 mmol) in t-BuOH (5 mL)/H$_2$O (10 mL) under N$_2$ atmosphere. The solution turned milky. After 4 hours the reaction was quenched with aqueous Na$_2$CO$_3$ (10%, 0.050 mL, 0.05 mmol) and filtered. The filtrate was lyophilized and the residue was purified by preparative RP-HPLC (Column: Waters XSelect CSH C18 ODB 5 μm 150×19 mm; mobile phase: A—H$_2$O/TFA 100/0.15 and B—MeCN with a gradient 5% B for 0.5 min, 5-36% B in 1.5 min, 36-41% B in 14 min; flow 30 mL/min at rt, detection 230 nm) to give the title compound (6.8 mg, 9%). HRMS: calculated for $(C_{305}H_{432}F_3N_{81}O_{72}S_9+4H)^{4+}$ 1682.5096; found (ESI [M+4H]$^{4+}$) 1682.5154, purity 97%.

Preparation of Example 251

Figure 3:
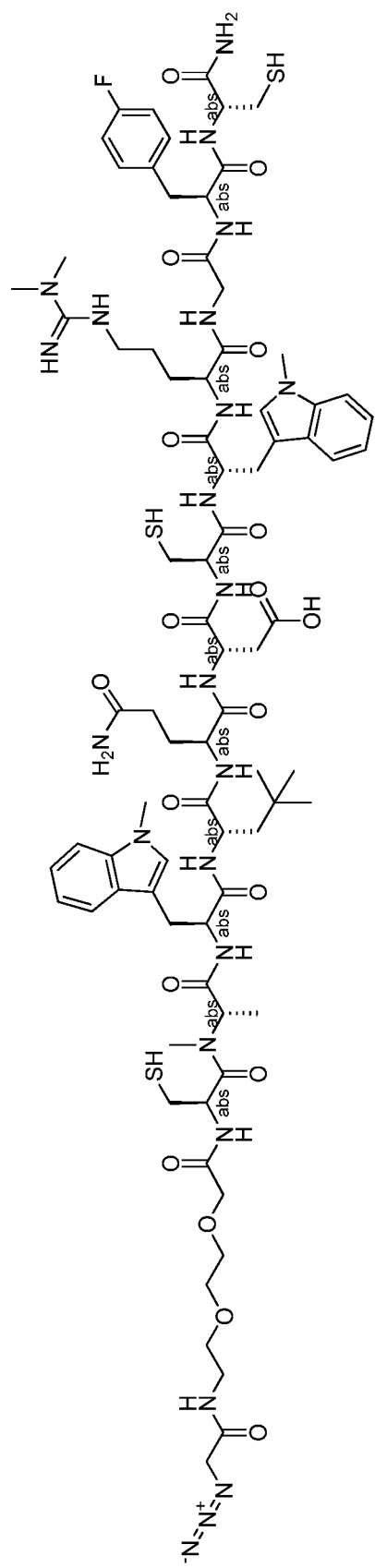
FIG. 3 depicts the structure of $N_3CH_2C(O)NH(CH_2CH_2O)_2CH_2C(O)$-Cys-NMeAla-1MeW-Ala(tBu)-Gln-Asp-Cys-1MeW-ADMA-Gly-4Fphe-Cys-$NH_2$.
Figure 4:
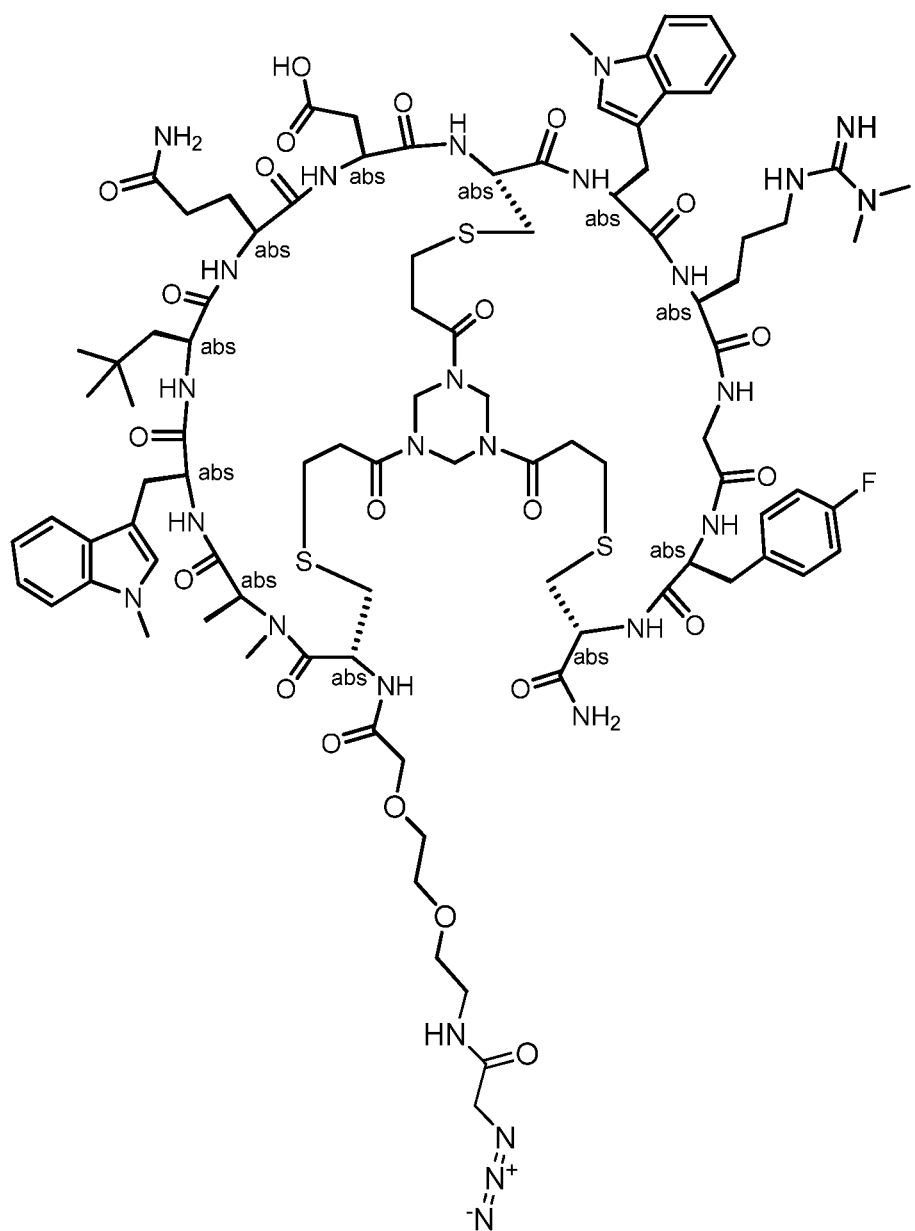
FIG. 4 depicts the structure of the TATA-cyclized intermediate of Example 251.

Step 1: Preparation of $N_3CH_2C(O)NH(CH_2CH_2O)_2CH_2C(O)$-Cys-NMeAla-1MeW-Ala(tBu)-Gln-Asp-Cys-1MeW-ADMA-Gly-4Fphe-Cys-NH$_2$ (as Depicted in FIG. 3)

The title compound was prepared as described in Example 250, step 4 on a 0.1 mmol scale, using Fmoc-NH—(CH$_2$CH$_2$O)$_2$—CH$_2$COOH in the penultimate coupling step. 98 mg (54%) of the title compound were obtained. LCMS (Acquity CSH C18 1.7 μm, pH 3, rt 6.26 min, 20 to 60% MeCN in 10 min): ES$^+$ m/z [M+2H]$^{2+}$=909.4, purity 78%.

Step 2: TATA Cyclization

The structure of TATA-cyclized intermediate is depicted in FIG. 2.

The foregoing linear peptide (98 mg, 0.04 mmol) was cyclized with TATA for 18 hours according to the TATA cyclization procedure to yield 105 mg of the crude product, which was used without further purification in the next step. LCMS (Acquity CSH C18 1.7 μm, pH 3, rt 2.47 min, 20 to 60% MeCN in 4 min): ES$^+$ m/z=1033.8 [M+2H]$^{2+}$, purity 91%.

Step 3: Preparation of Example 251

Figure 5:
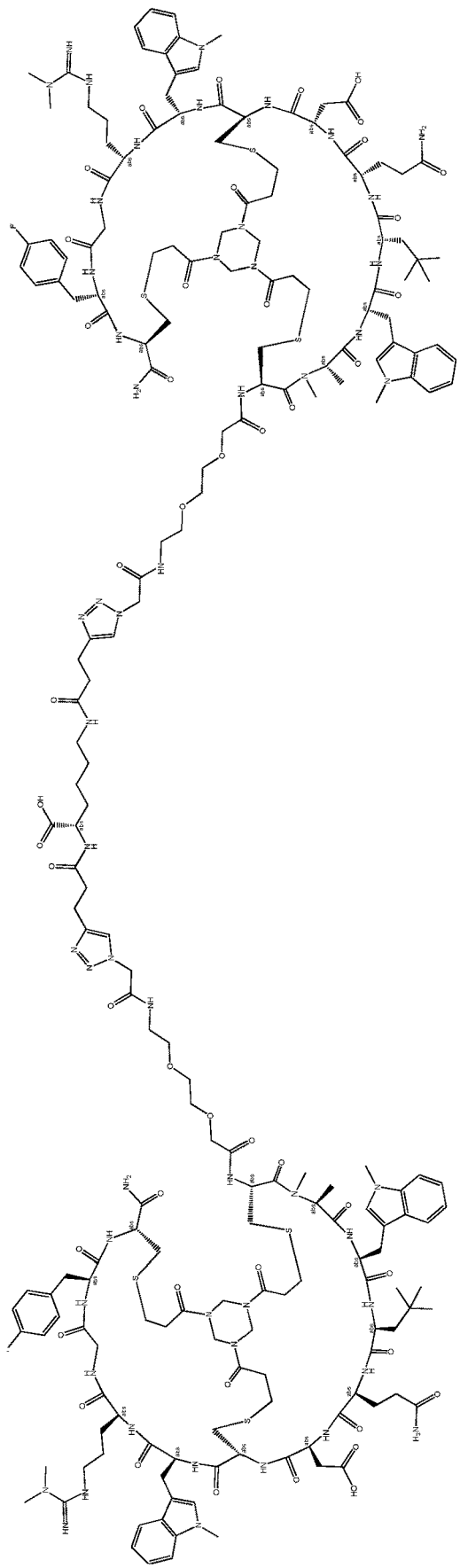
FIG. 5 depicts the structure of the title compound of Example 251.

The structure of the compound of Example 251 is depicted in FIG. 5.

(+)-Sodium L-ascorbate (16 mg, 0.08 mmol) was added to a solution of the foregoing compound (105 mg, 0.05 mmol), N$^2$,N$^6$-dipent-4-ynoyl-L-lysine (6 mg, 0.02 mmol) and CuSO$_4$.5H$_2$O (20 mg, 0.08 mmol) in t-BuOH (10 mL)/H$_2$O (20 mL) under N$_2$ atmosphere. The solution turned milky. The reaction was stirred at rt for 6.5 h and more N$^2$,N$^6$-dipent-4-ynoyl-L-lysine (6 mg, 0.02 mmol) was added. After 23 h the reaction was quenched with aqueous Na$_2$CO$_3$ (0.166 mL, 0.16 mmol) and filtered. The filtrate was freeze dried, and the crude product purified by preparative HPLC (Column: Waters Atlantis T3 ODB 5 μm 150×19 mm; mobile phase: A—H$_2$O/TFA 100/0.15 and B—MeCN with a gradient 5% B for 0.5 min, 5-38% B in 1.5 min, 38-43% B in 14 min; flow 30 mL/min at rt, detection 230 nm) to give the title compound obtained (5.5 mg, 3%). HRMS: calculated for $(C_{200}H_{280}F_2N_{34}O_{48}S_6+3H)^{3+}$ 1479.6552; found (ESI [M+3H]$^{3+}$) 1479.6583, purity 82%.

Preparation of Bridged 5×4 Bicyclic Peptides

Preparation of Example 234 (Isomer 1) and Example 235 (Isomer 2)

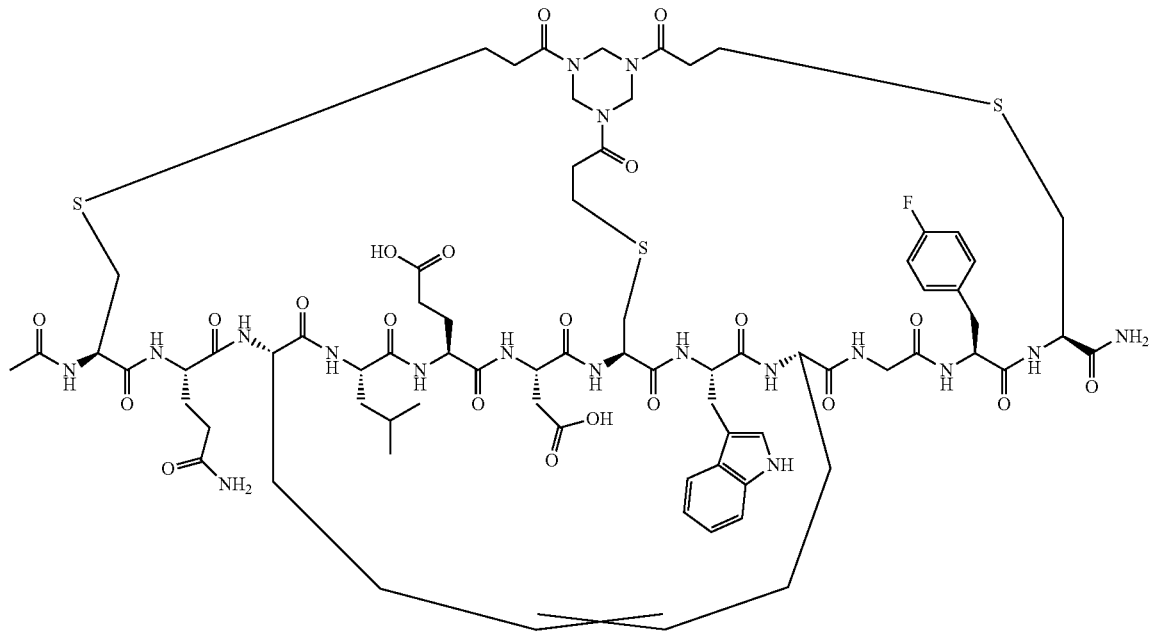 [SMILES: CC(=O)N[C@H]1CSCCC(=O)N2CN3CN(C2)C(=O)CCSC[C@@H]2NC(=O)[C@H](CC(=O)O)NC(=O)[C@H](CCC(=O)O)NC(=O)[C@H](CC(C)C)NC(=O)[C@H](CCC=CCC[C@H](NC(=O)[C@H](Cc4c[nH]c5ccccc45)NC2=O)C(=O)NCC(=O)N[C@@H](Cc2ccc(F)cc2)C(=O)N[C@H](C(N)=O)CSCCC3=O)NC(=O)[C@H](CCC(N)=O)NC1=O]

Step 1: Preparation of the Linear Precursor on the Resin

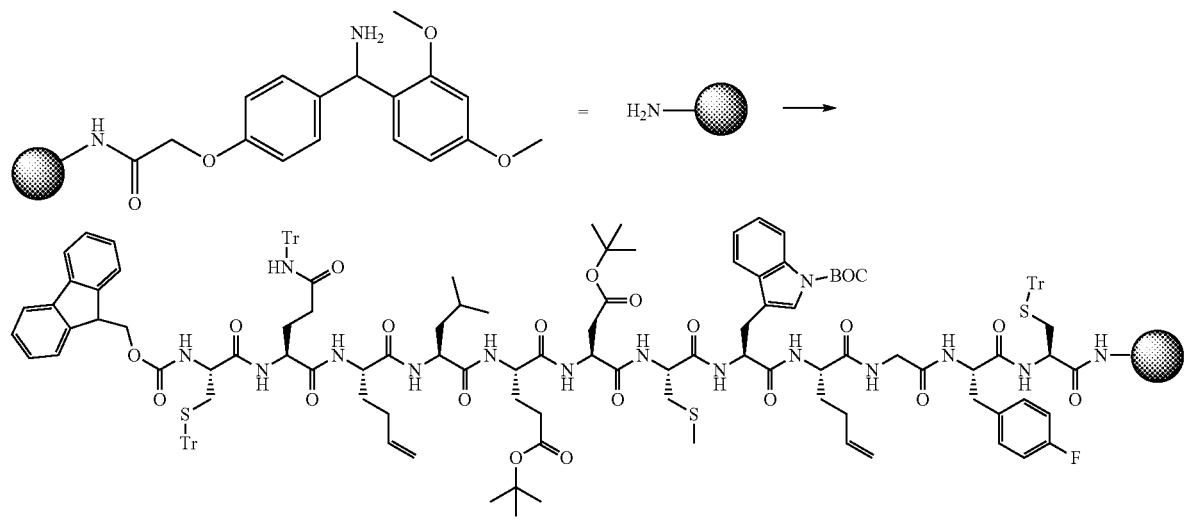

The resin-bound peptide was prepared manually using TGR R resin (NovaSyn, 2 g, 0.48 mmol, loading: 0.24 mmol/g), which was treated with DCM (40 mL) prior to the synthesis and left for 30 min. The appropriate Fmoc-protected amino acid (1.5 eq) and HATU (1.5 eq) were dissolved in DMF (10 mL) and the solution was added to the resin, followed by DIPEA (3 eq.). The reaction was agitated at rt for 45 min. After each coupling, the resin was washed with DMF (3×5 mL), DCM (3×5 mL) and MeOH (3×5 mL). The Fmoc protecting group was removed by agitating the resin in a solution of 20% piperidine in DMF (5 mL, v/v) for 10 min and washed with DMF (3×5 mL). This procedure was repeated another two times. After the last coupling step, the Fmoc protective group was not removed. The resin was then washed with DMF (3×5 mL), DCM (3×10 min) and MeOH (3×5 mL) and dried under vacuum at rt to yield 2.13 g of the functionalized resin.

Step 2: Ring-Closing Metathesis

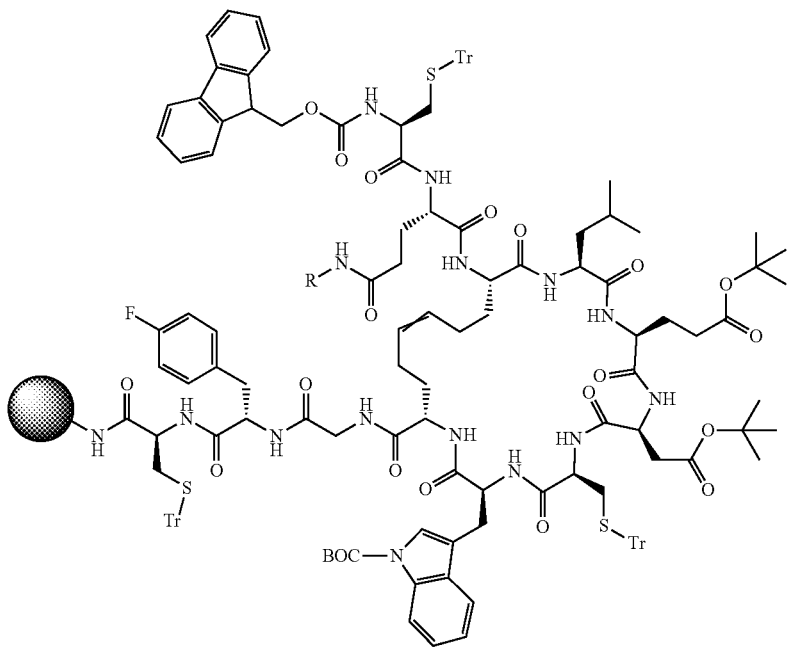

The dried resin from step 1 (2.13 g, 0.24 mmol/g, theoretical loading of peptide 0.48 mmol) was mixed with anhydrous DCM (130 mL), and nitrogen was bubbled through the solution for 5 minutes. To the resulting mixture was added benzylidenbis(tricyclohexylphosphin)-dichlororuthenium (Grubbs catalyst $1^{st}$ generation, 107 mg, 0.128 mmol) dissolved in DCM (5 mL) and the reaction mixture was stirred at 40° C. under nitrogen for 72 h. At this point cleavage of reaction mixture from the resin and analysis by LCMS (Acquity CSH, Fluorophenyl column, 2.1×50 mm, 1.8 µm, pH 3, 30 to 70% MeCN in 10 min) indicated the formation of two regioisomeric products (RT 4.54 and 4.71 min, 35% and 42% respectively) and about 11% of remaining linear peptide (RT 6.95 min). The resin was isolated by filtration, washed with DMF, DCM and MeOH (3×5 mL each) and dried.

Step 3: N-Acetylation and Cleavage

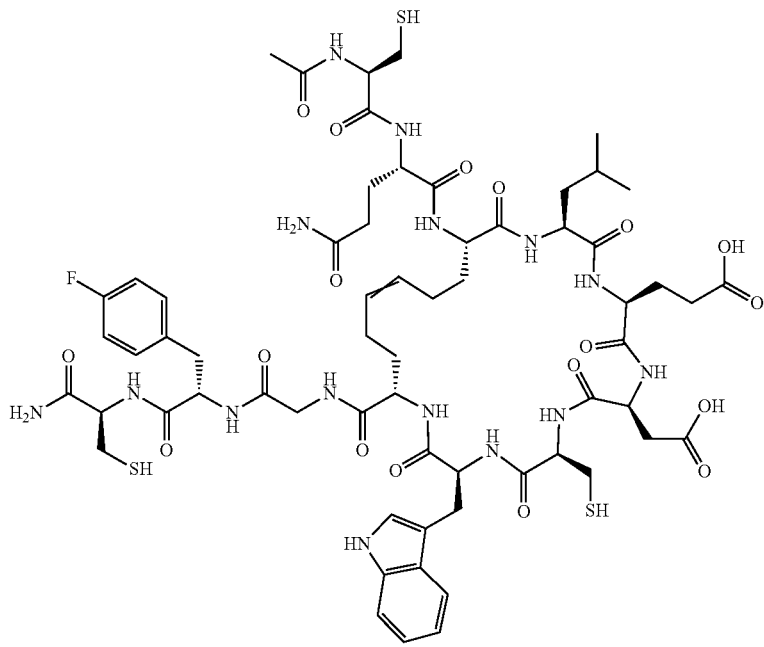 [SMILES: CC(=O)N[C@@H](CS)C(=O)N[C@@H](CCC(N)=O)C(=O)N[C@H]1CCC=CCC[C@@H](C(=O)NCC(=O)N[C@@H](Cc2ccc(F)cc2)C(=O)N[C@@H](CS)C(N)=O)NC(=O)[C@H](Cc2c[nH]c3ccccc23)NC(=O)[C@H](CS)NC(=O)[C@H](CC(=O)O)NC(=O)[C@H](CCC(=O)O)NC(=O)[C@H](CC(C)C)NC1=O]

The Fmoc group was removed by agitating the resin in a solution of 20% piperidine in DMF (5 mL, v/v) for 10 min and washed with DMF (3×5 mL). The deprotection procedure was repeated another two times. The resin was then washed with DMF (3×5 mL), DCM (3×10 min) and MeOH (3×5 mL) and dried under vacuum. Treatment with Ac$_2$O (10 eq), dissolved in 5 mL DMF and i-Pr$_2$NEt at rt for 20 min was used to install the N-terminal acetyl group. The resin was then washed with DMF (3×5 mL), DCM (3×5 mL) and MeOH (3×5 mL) and Et$_2$O (3×5 mL) and dried under vacuum. The bound peptide was cleaved from the resin and deprotected by gentle agitation in a mixture of TFA/TIS/H$_2$O/DODT (92.5/2.5/2.5/2.5, v/v, 20 mL) for 2.5 h. Precipitation from cold ether, centrifugation and drying under high vacuum yielded the desired crude peptide (284 mg, 41%), which was used without further purification.

Step 4: TATA Cyclization

The crude peptide (146 mg, 0.1 mmol) obtained in step 3 was dissolved in a mixture of MeCN/H$_2$O (10 mL, 1:1, v/v) and aqueous NH$_4$CO$_3$ buffer (0.06 M, 20 mL) was added, followed by dropwise addition of a solution of TATA (20 mg, 0.08 mmol) in MeCN (5 mL) over 35 min. The mixture was stirred at rt for 1 h. Then formic acid (0.5 mL) was added, and the resulting mixture was freeze dried. The crude product was purified by preparative HPLC (Column: Waters Atlantis T3 ODB 5 μm 150×19 mm; mobile phase: A—H$_2$O/TFA 100/0.1 and B—MeCN with a gradient 5% B for 0.5 min, 5-23% B in 2 min, 23-33% B in 30 min; flow 30 mL/min at rt, detection 210 nm) to give isomer 1 of the title compound (8.2 mg, 4.8%) as the first fraction and isomer 2 (9.5 mg, 5.6%) as the second fraction.

Isomer 1: HRMS: calculated for $(C_{75}H_{101}FN_{18}O_{21}S_3+2H)^{2+}$ 853.3345; found (ESI [M+2H]$^{2+}$) 853.3354, purity 92%.

Isomer 2: HRMS: calculated for $(C_{75}H_{101}FN_{18}O_{21}S_3+2H)^{2+}$ 853.3345; found (ESI [M+2H]$^{2+}$) 853.3353, purity 86%.

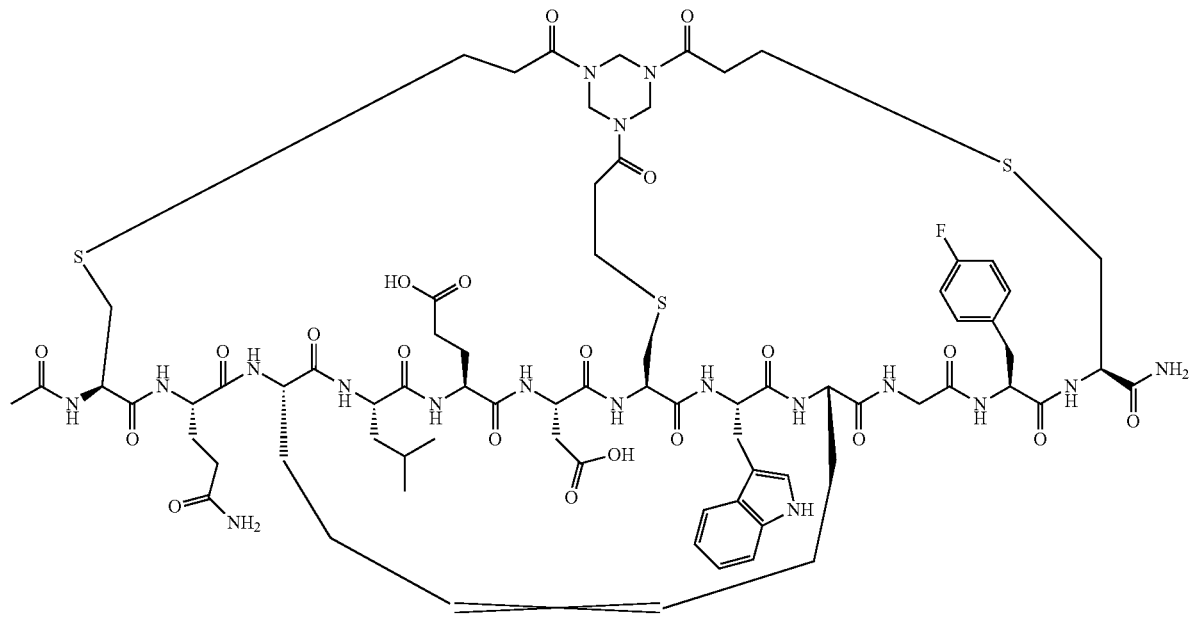 [SMILES: CCC[C@@H]1NC(=O)[C@H](Cc2c[nH]c3ccccc23)NC(=O)[C@@H]2CSCCC(=O)N3CN(CN(C3)C(=O)CCSC[C@H](NC(C)=O)C(=O)N[C@@H](CCC(N)=O)C(=O)N[C@@H](CCC)C(=O)N[C@@H](CC(C)C)C(=O)N[C@@H](CCC(=O)O)C(=O)N[C@@H](CC(=O)O)C(=O)N2)C(=O)CCSC[C@@H](C(N)=O)NC(=O)[C@H](Cc2ccc(F)cc2)NC(=O)CNC1=O]

Preparation of Example 236

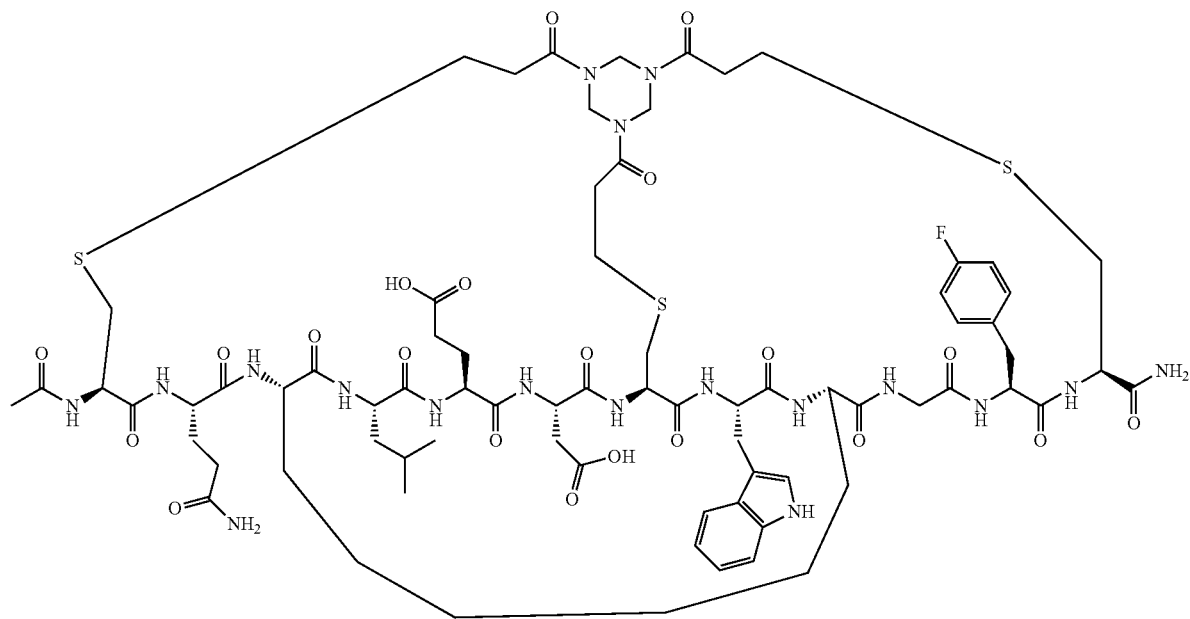 [SMILES: CC(=O)N[C@H]1CSCCC(=O)N2CN3CN(C2)C(=O)CCSC[C@@H]2NC(=O)[C@H](CC(=O)O)NC(=O)[C@H](CCC(=O)O)NC(=O)[C@H](CC(C)C)NC(=O)[C@H](CCCCCC[C@H](NC(=O)[C@H](Cc4c[nH]c5ccccc45)NC2=O)C(=O)NCC(=O)N[C@@H](Cc2ccc(F)cc2)C(=O)N[C@H](C(N)=O)CSCCC3=O)NC(=O)[C@H](CCC(N)=O)NC1=O]

Step 1: Hydrogenation and Cleavage from the Resin

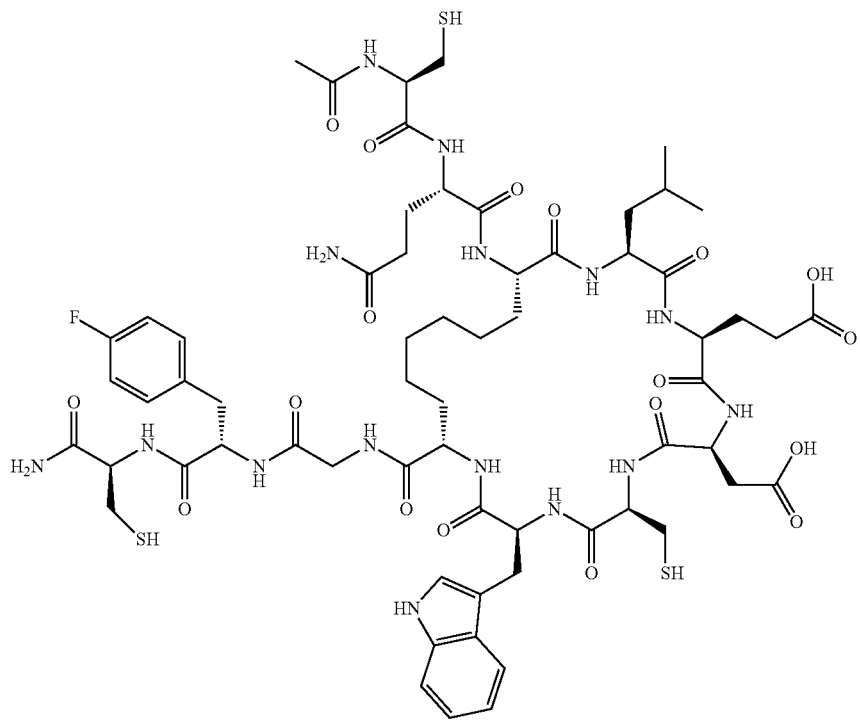 [SMILES: CC(=O)N[C@@H](CS)C(=O)N[C@@H](CCC(N)=O)C(=O)N[C@H]1CCCCCC[C@@H](C(=O)NCC(=O)N[C@@H](Cc2ccc(F)cc2)C(=O)N[C@@H](CS)C(N)=O)NC(=O)[C@H](Cc2c[nH]c3ccccc23)NC(=O)[C@H](CS)NC(=O)[C@H](CC(=O)O)NC(=O)[C@H](CCC(=O)O)NC(=O)[C@H](CC(C)C)NC1=O]

1.5 g of resin (theoretical peptide load 0.25 mmol), prepared as described in step 2 of Examples 234/235 was suspended in a mixture of DCM/MeOH (10 mL, v/v) in an autoclave. Wilkinson's catalyst (100 mg, 0.11 mmol) was added, and the reaction was stirred under hydrogen pressure (4 bar) at 40° C. for 24 h. The resin was isolated by filtration and washed with DMF (3×5 mL), DCM (3×5 mL) and MeOH (3×5 mL). Fmoc-cleavage, acetylation and cleavage of the peptide from the resin was performed as described in step 3 for examples 234/235 gave 57 mg (16%) of a crude product, which was used without further purification.

Step 3: TATA Cyclization

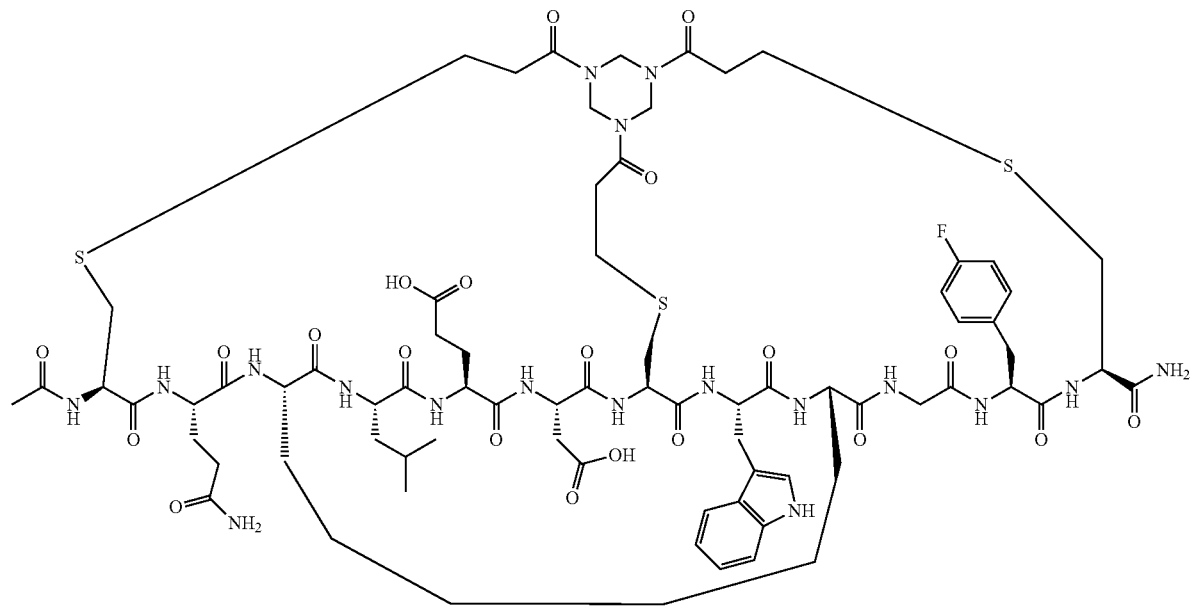 [SMILES: CC(=O)N[C@H]1CSCCC(=O)N2CN3CN(C2)C(=O)CCSC[C@@H]2NC(=O)[C@H](CC(=O)O)NC(=O)[C@H](CCC(=O)O)NC(=O)[C@H](CC(C)C)NC(=O)[C@H](CCCCCC[C@H](NC(=O)[C@H](Cc4c[nH]c5ccccc45)NC2=O)C(=O)NCC(=O)N[C@@H](Cc2ccc(F)cc2)C(=O)N[C@H](C(N)=O)CSCCC3=O)NC(=O)[C@H](CCC(N)=O)NC1=O]

The crude peptide (57 mg, 0.04 mmol) from the foregoing step was cyclized with TATA as described in Examples 23/235 step 4. The crude product was purified by preparative HPLC (Column: Waters Xselect® CSH Prep, C18 5 μm OBD™, 19×150 mm; mobile phase: A—H₂O+TFA (0.1%) and B—MeCN+TFA (0.1%) with a gradient 5% B for 0.5 min, 5-20% B in 2 min, 20-30% B in 20 min; flow 30 mL/min at rt, detection 210 nm) to give the title compound (3.3 mg, 3.9%). HRMS: calculated for $(C_{75}H_{103}FN_{18}O_{21}S_3+2H)^{2+}$ 854.3424; found (ESI [M+2H]$^{2+}$ 854.3429, purity 99%.

Using the methods described in Examples 234 to 236, the compounds shown in Tables 5 and 6 were prepared.

TABLE 5

Stapled 5 × 4 Bicycles

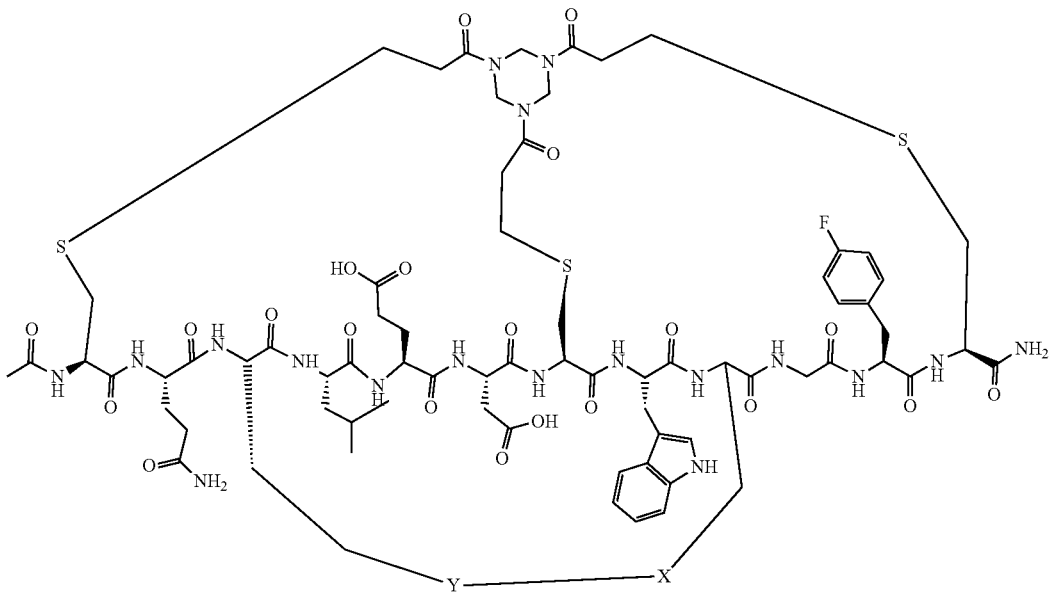

TABLE 5-continued

| Example Number | X—Y | Mw | HRMS calc. for [M + 2H]$^{2+}$ | HRMS found [M + 2H]$^{2+}$ | Purity (%) |
|---|---|---|---|---|---|
| 237 | CH$_2$—CH—CH—CH$_2$—CH$_2$— | 1736.0 | 868.3580 | 868.3590 | 98 |
| 238 | CH$_2$—CH—CH—CH$_2$— | 1722.0 | 861.3502 | 861.3512 | 98 |
| 239 (isomer 1) | CH$_2$—CH=CH—CH$_2$— | 1719.9 | 860.3424 | 860.3452 | 87 |
| 240 (isomer 2) | CH$_2$—CH=CH—CH$_2$— | 1719.9 | 860.3424 | 860.3433 | 90 |
| 241 (isomer 1) | CH$_2$=CH—CH—CH$_2$— | 1719.9 | 860.3424 | 860.3436 | 79 |
| 242 | CH$_2$—CH=CH—CH$_2$—CH$_2$— | 1734.0 | 867.3502 | 867.3511 | 97 |
| 243 (isomer 2) | CH$_2$=CH—CH—CH$_2$— | 1719.9 | 860.3424 | 860.3447 | 87 |

TABLE 6

Stapled 5 × 4 Bicycles

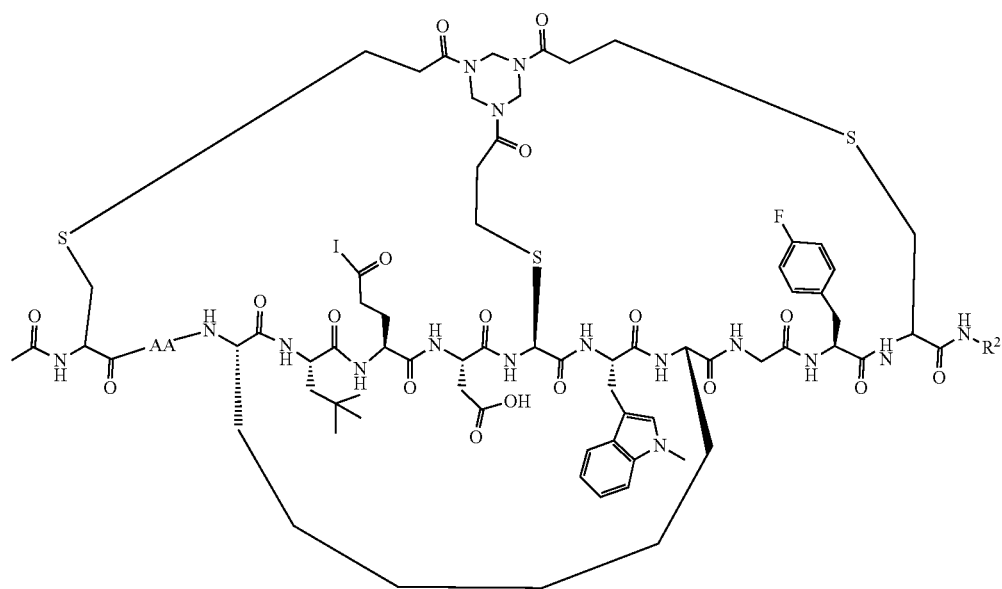

| Example Number | AA | R$^1$ | R$^2$ | Mw | HRMS calc. for [M + 2H]$^{2+}$ | HRMS found [M + 2H]$^{2+}$ | Purity (%) |
|---|---|---|---|---|---|---|---|
| 244 | Gln | OH | NH$_2$ | 1736.0 | 868.3580 | 868.3574 | 95 |
| 245 | Gln | NH$_2$ | NH$_2$ | 1735.0 | 867.8660 | 867.8679 | 90 |
| 246 | Gln | OH | ala | 1807 | 903.8766 | 903.8766 | 91 |
| 247 | NMeAla | NH$_2$ | NH$_2$ | 1692 | 846.3631 | 846.3660 | 91 |

Preparation of Example 248

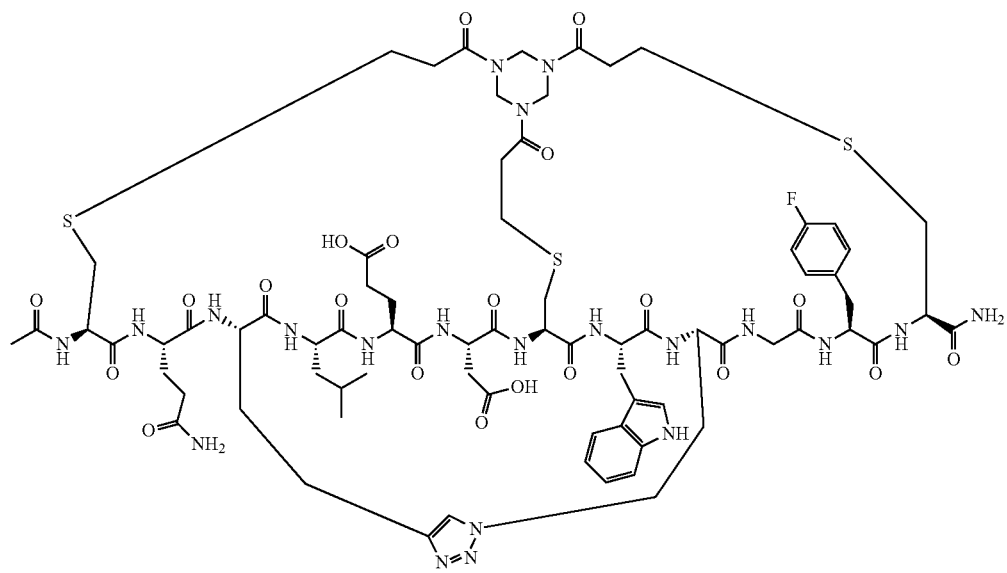 [SMILES: CC(=O)N[C@H]1CSCCC(=O)N2CN3CN(C2)C(=O)CCSC[C@@H]2NC(=O)[C@H](CC(=O)O)NC(=O)[C@H](CCC(=O)O)NC(=O)[C@H](CC(C)C)NC(=O)[C@H](CCc4cn(nn4)CC[C@H](NC(=O)[C@H](Cc4c[nH]c5ccccc45)NC2=O)C(=O)NCC(=O)N[C@@H](Cc2ccc(F)cc2)C(=O)N[C@H](C(N)=O)CSCCC3=O)NC(=O)[C@H](CCC(N)=O)NC1=O]

Step 1. Preparation of Ac-Cys-Gln-X$_2$-Leu-Glu-Asp-Cys-Trp-X$_1$-G-Phe(4-F)-CysNH$_2$ (X$_1$=L-2-amino-azidobutanoic acid, X2=L-2-aminohept-6-ynoic acid)

The resin-bound peptide was prepared manually using Chemmatrix Rink amide resin (Biotage, 531 mg, 0.25 mmol, loading: 0.48 mmol/g), which was treated with DCM (20 mL) prior to the synthesis and left for 30 min. The appropriate Fmoc-protected amino acid (1.5 eq) and HATU (1.5 eq) were dissolved in DMF (10 mL) and the solution was added to the resin, followed by DIPEA (3 eq.). The reaction was agitated at rt for 45 min. After each coupling, the resin was washed with DMF (3×5 mL), DCM (3×5 mL) and MeOH (3×5 mL). The Fmoc protecting group was removed by agitating the resin in a solution of 20% piperidine in DMF (5 mL, v/v) for 10 min and washed with DMF (3×5 mL). This procedure was repeated another two times. After the last coupling and removal of the Fmoc protective group, the resin was treated with Ac$_2$O (10 eq) and DIPEA (10 eq) in DMF (5 mL) for 60 min. After filtration, the resin was washed with DMF (3×5 mL), DCM (3×10 min) and Et$_2$O (3×5 mL) and dried under vacuum. The bound peptide was cleaved from the resin and deprotected by gentle agitation in a mixture of TFA/TIS/H$_2$O/DODT (92.5/2.5/2.5/2.5, v/v, 27 mL) for 2.5 h. Precipitation from cold ether, centrifugation and drying under high vacuum yielded the desired crude peptide (353 mg, 92%), which was used without further purification.

Step 2: TATA Cyclization

The crude peptide (353 mg, 0.24 mmol, 70% purity) from the foregoing step was dissolved in MeCN/H$_2$O (20 mL, 1:1, v/v) and aqueous NH$_4$CO$_3$ buffer (0.06 M, 40 mL) was added, followed by dropwise addition of a solution of TATA (48 mg, 0.192 mmol) in MeCN (10 mL) over 20 min. The mixture was stirred at rt for 1 h. Then formic acid (2 mL) was added, and the resulting mixture was freeze dried to give 210 mg of a crude product.

Step 3: Click Reaction

The crude product (100 mg, 0.06 mmol) obtained in step 2 and CuSO$_4$ pentahydrate (66 mg, 0.26 mmol) were solubilized in a mixture of water and tert-butanol (2:1, v/v, 100 mL). To this mixture was added slowly a solution of sodium ascorbate (52 mg, 0.26 mmol) in water (2 mL). The resulting mixture was stirred for 2 h at rt. The alcohol was evaporated in vacuo, and the residue lyophilized. The crude product was purified by preparative HPLC (Column: Waters Xselect® CSH Prep, C18 5 μm OBD™, 19×150 mm; mobile phase: A—H$_2$O+TFA (0.1%) and B—MeCN+TFA (0.1%) with a gradient 5% B for 0.5 min, 5-25% B in 2 min, 25-30% B in 20 min; flow 30 mL/min at rt, detection 210 nm) to give the title compound (1.2 mg, 1%). HRMS: calculated for (C$_{75}$H$_{100}$FN$_{21}$O$_{21}$S$_3$+2H)$^{2+}$ 873.8353; found (ESI [M+2H]$^{2+}$ 873.8361, purity 99%.

Preparation of Example 249

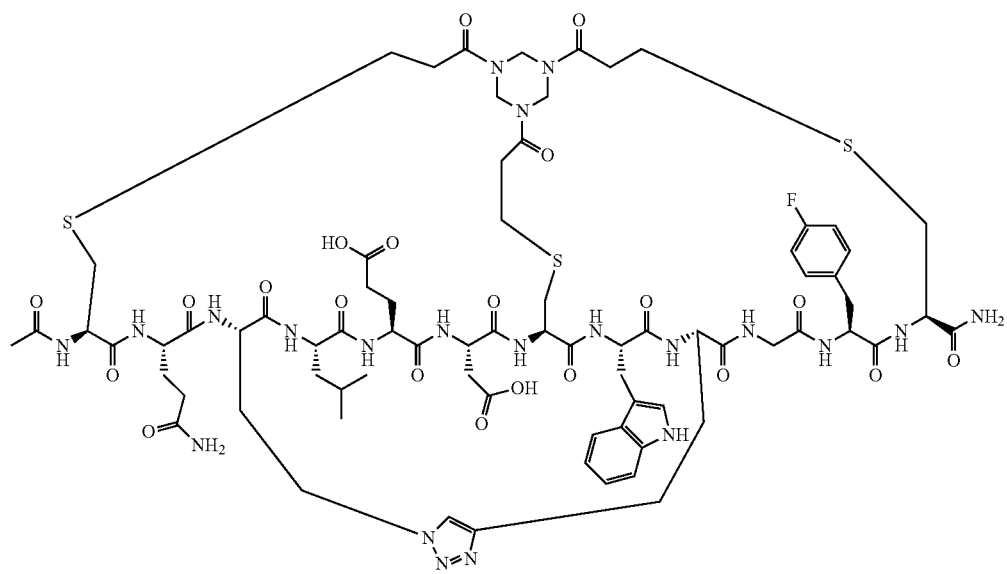 [SMILES: CC(=O)N[C@H]1CSCCC(=O)N2CN3CN(C2)C(=O)CCSC[C@@H]2NC(=O)[C@H](CC(=O)O)NC(=O)[C@H](CCC(=O)O)NC(=O)[C@H](CC(C)C)NC(=O)[C@H](CCn4cc(nn4)CC[C@H](NC(=O)[C@H](Cc4c[nH]c5ccccc45)NC2=O)C(=O)NCC(=O)N[C@@H](Cc2ccc(F)cc2)C(=O)N[C@H](C(N)=O)CSCCC3=O)NC(=O)[C@H](CCC(N)=O)NC1=O]

Following the procedures described in Example 248 gave the title compound (0.6 mg, 0.5%). LCMS: calculated for $(C_{75}H_{100}FN_{21}O_{21}S_3+2H)^{2+}$ 874.5; found ESI $[M+2H]^{2+}$ 874.4, purity 95%.

Biological Data

Human TSLP Surface Plasmon Resonance (SPR) Binding Assay

Biotinylated human TSLP, was immobilized on a streptavidin-coated biosensor chip (GE Helathcare or XanTec bioanalytics GmbH). Typical capture levels were 500-2000 response units (RU). Buffer conditions were 50 mM HEPES pH 7.4, 150 mM NaCl, 0.005% (v/v) Tween20 and 1% DMSO. Peptides were injected at a flow rate of 30 µL/min and binding was determined in 7 or 10 concentration-response series, with maximum concentrations of 10 or 100 µM and 1/3 dilution steps. Typical contact times were 60 seconds followed by 180-600 seconds dissociation. Sensorgrams were fit either with a steady-state or kinetic 1:1 binding model to obtain $K_D$ values. Experiments were conducted at 20° C.

The compounds of Examples 1 to 252 were tested in the above mentioned human TSLP SPR assay and the results are shown in Table 7 below.

TABLE 7

Human TSLP SPR Data for Peptide Ligands of the Invention

| Example Number | hTSLP SPR Kd (µM) | n |
|---|---|---|
| 1 | 0.002 | 2 |
| 2 | 0.0024 | 4 |
| 3 | 0.0025 | 4 |
| 4 | 0.0027 | 3 |
| 5 | 0.0027 | 4 |
| 6 | 0.0028 | 4 |
| 7 | 0.0031 | 4 |
| 8 | 0.004 | 3 |
| 9 | 0.0048 | 2 |
| 10 | 0.0056 | 3 |
| 11 | 0.0058 | 7 |

TABLE 7-continued

Human TSLP SPR Data for Peptide Ligands of the Invention

| Example Number | hTSLP SPR Kd (µM) | n |
|---|---|---|
| 12 | 0.0059 | 2 |
| 13 | 0.006 | 4 |
| 14 | 0.006 | 3 |
| 15 | 0.0062 | 2 |
| 16 | 0.0063 | 3 |
| 17 | 0.0063 | 15 |
| 18 | 0.0063 | 4 |
| 19 | 0.0067 | 2 |
| 20 | 0.0086 | 4 |
| 21 | 0.0092 | 3 |
| 22 | 0.0097 | 4 |
| 23 | 0.0099 | 2 |
| 24 | 0.01 | 2 |
| 25 | 0.01 | 4 |
| 26 | 0.011 | 2 |
| 27 | 0.012 | 3 |
| 28 | 0.012 | 2 |
| 29 | 0.013 | 3 |
| 30 | 0.013 | 4 |
| 31 | 0.014 | 4 |
| 32 | 0.014 | 6 |
| 33 | 0.014 | 2 |
| 34 | 0.015 | 3 |
| 35 | 0.015 | 2 |
| 36 | 0.016 | 2 |
| 37 | 0.019 | 2 |
| 38 | 0.02 | 3 |
| 39 | 0.021 | 2 |
| 40 | 0.022 | 2 |
| 41 | 0.024 | 2 |
| 42 | 0.029 | 2 |
| 43 | 0.03 | 4 |
| 44 | 0.031 | 3 |
| 45 | 0.033 | 2 |
| 46 | 0.033 | 2 |
| 47 | 0.033 | 4 |
| 48 | 0.033 | 2 |
| 49 | 0.036 | 2 |
| 50 | 0.037 | 5 |
| 51 | 0.038 | 2 |
| 52 | 0.038 | 2 |

TABLE 7-continued

Human TSLP SPR Data for Peptide Ligands of the Invention

| Example Number | hTSLP SPR Kd (μM) | n |
|---|---|---|
| 53 | 0.043 | 2 |
| 54 | 0.046 | 4 |
| 55 | 0.047 | 4 |
| 56 | 0.048 | 2 |
| 57 | 0.051 | 2 |
| 58 | 0.052 | 2 |
| 59 | 0.052 | 2 |
| 60 | 0.062 | 2 |
| 61 | 0.062 | 2 |
| 62 | 0.063 | 2 |
| 63 | 0.065 | 2 |
| 64 | 0.069 | 2 |
| 65 | 0.07 | 2 |
| 66 | 0.071 | 4 |
| 67 | 0.075 | 2 |
| 68 | 0.075 | 10 |
| 69 | 0.077 | 2 |
| 70 | 0.08 | 4 |
| 71 | 0.082 | 4 |
| 72 | 0.084 | 2 |
| 73 | 0.085 | 2 |
| 74 | 0.091 | 3 |
| 75 | 0.092 | 2 |
| 76 | 0.093 | 10 |
| 77 | 0.093 | 2 |
| 78 | 0.094 | 4 |
| 79 | 0.098 | 6 |
| 80 | 0.1 | 2 |
| 81 | 0.1 | 4 |
| 82 | 0.11 | 4 |
| 83 | 0.11 | 2 |
| 84 | 0.11 | 5 |
| 85 | 0.12 | 2 |
| 86 | 0.12 | 2 |
| 87 | 0.12 | 4 |
| 88 | 0.13 | 4 |
| 89 | 0.13 | 6 |
| 90 | 0.13 | 2 |
| 91 | 0.13 | 2 |
| 92 | 0.13 | 2 |
| 93 | 0.14 | 6 |
| 94 | 0.14 | 2 |
| 95 | 0.14 | 2 |
| 96 | 0.15 | 3 |
| 97 | 0.15 | 2 |
| 98 | 0.15 | 2 |
| 99 | 0.16 | 6 |
| 100 | 0.16 | 4 |
| 101 | 0.16 | 6 |
| 102 | 0.17 | 3 |
| 103 | 0.18 | 6 |
| 104 | 0.18 | 3 |
| 105 | 0.18 | 2 |
| 106 | 0.19 | 2 |
| 107 | 0.19 | 3 |
| 108 | 0.19 | 2 |
| 109 | 0.19 | 6 |
| 110 | 0.19 | 4 |
| 111 | 0.2 | 2 |
| 112 | 0.21 | 3 |
| 113 | 0.22 | 2 |
| 114 | 0.23 | 2 |
| 115 | 0.23 | 15 |
| 116 | 0.25 | 3 |
| 117 | 0.25 | 2 |
| 118 | 0.25 | 2 |
| 119 | 0.26 | 3 |
| 120 | 0.28 | 4 |
| 121 | 0.29 | 4 |
| 122 | 0.29 | 6 |
| 123 | 0.29 | 3 |
| 124 | 0.29 | 6 |
| 125 | 0.3 | 2 |
| 126 | 0.31 | 3 |
| 127 | 0.32 | 4 |
| 128 | 0.38 | 2 |
| 129 | 0.4 | 3 |
| 130 | 0.4 | 4 |
| 131 | 0.4 | 3 |
| 132 | 0.41 | 2 |
| 133 | 0.47 | 3 |
| 134 | 0.47 | 4 |
| 135 | 0.49 | 3 |
| 136 | 0.52 | 2 |
| 137 | 0.52 | 4 |
| 138 | 0.52 | 2 |
| 139 | 0.53 | 4 |
| 140 | 0.55 | 2 |
| 141 | 0.6 | 3 |
| 142 | 0.71 | 4 |
| 143 | 0.75 | 2 |
| 144 | 0.86 | 2 |
| 145 | 0.9 | 2 |
| 146 | 0.91 | 3 |
| 147 | 0.94 | 2 |
| 148 | 1.1 | 4 |
| 149 | 1.1 | 3 |
| 150 | 1.5 | 4 |
| 151 | 1.5 | 2 |
| 152 | 1.7 | 6 |
| 153 | 2.7 | 3 |
| 154 | 2.9 | 2 |
| 155 | 3.2 | 3 |
| 156 | 3.3 | 3 |
| 157 | 3.9 | 3 |
| 158 | 5.4 | 3 |
| 159 | 5.6 | 6 |
| 160 | 10 | 4 |
| 161 | 0.89 | 4 |
| 162 | 1.5 | 3 |
| 163 | 0.23 | 6 |
| 164 | 0.098 | 6 |
| 165 | 0.03 | 2 |
| 166 | 0.12 | 2 |
| 167 | 0.17 | 2 |
| 168 | 0.29 | 2 |
| 169 | 0.29 | 2 |
| 170 | 0.17 | 2 |
| 171 | 0.048 | 2 |
| 172 | 0.14 | 2 |
| 173 | 0.077 | 2 |
| 174 | 0.13 | 2 |
| 175 | 0.24 | 2 |
| 176 | 0.3 | 2 |
| 177 | 0.58 | 2 |
| 178 | 0.19 | 4 |
| 179 | 0.36 | 4 |
| 180 | 0.3 | 4 |
| 181 | 0.31 | 4 |
| 182 | 1.3 | 2 |
| 183 | 0.33 | 6 |
| 184 | 0.13 | 6 |
| 185 | 0.26 | 3 |
| 186 | 0.066 | 2 |
| 187 | 0.086 | 2 |
| 188 | 0.072 | 2 |
| 189 | 0.31 | 2 |
| 190 | 0.081 | 2 |
| 191 | 0.11 | 2 |
| 192 | 0.084 | 2 |
| 193 | 0.05 | 2 |
| 194 | 0.29 | 2 |
| 195 | 15 | 2 |
| 196 | 6.1 | 2 |
| 197 | 0.46 | 4 |
| 198 | 0.29 | 6 |
| 199 | 0.081 | 6 |
| 200 | 0.068 | 6 |
| 201 | 0.17 | 2 |
| 202 | 0.19 | 2 |

TABLE 7-continued

Human TSLP SPR Data for Peptide Ligands of the Invention

| Example Number | hTSLP SPR Kd (µM) | n |
|---|---|---|
| 203 | 0.32 | 2 |
| 204 | 0.1 | 2 |
| 205 | 0.15 | 2 |
| 206 | 0.43 | 2 |
| 207 | 0.14 | 2 |
| 208 | 0.34 | 2 |
| 209 | 0.91 | 2 |
| 210 | 0.18 | 2 |
| 211 | 0.14 | 2 |
| 212 | 0.25 | 2 |
| 213 | 0.12 | 2 |
| 214 | 0.071 | 2 |
| 215 | 0.24 | 4 |
| 216 | 0.32 | 4 |
| 217 | 0.86 | 2 |
| 218 | 2 | 2 |
| 219 | 0.55 | 4 |
| 220 | 0.34 | 6 |
| 221 | 0.089 | 2 |
| 222 | 0.45 | 2 |
| 223 | 3 | 4 |
| 224 | 0.066 | 4 |
| 225 | 0.071 | 4 |
| 226 | 0.076 | 6 |
| 227 | 0.74 | 2 |
| 228 | 2.3 | 2 |
| 229 | 9.9 | 2 |
| 230 | 0.96 | 3 |
| 231 | 1.8 | 3 |
| 232 | 8.3 | 3 |
| 233 | 2.7 | 3 |
| 234 | 0.097 | 8 |
| 235 | 0.052 | 10 |
| 236 | 0.077 | 2 |
| 237 | 0.082 | 2 |
| 238 | 0.66 | 2 |
| 239 | 0.18 | 2 |
| 240 | 0.16 | 2 |
| 241 | 1.8 | 2 |
| 242 | 0.11 | 2 |
| 243 | 0.24 | 2 |
| 244 | 0.016 | 4 |
| 245 | 0.053 | 2 |
| 246 | 0.025 | 2 |
| 247 | 0.025 | 4 |
| 248 | 0.19 | 2 |
| 249 | 1.2 | 2 |
| 250 | 0.000027 | 2 |
| 251 | 0.00014 | 4 |
| 252 | 0.56 | 2 |

Human Peripheral Blood Mononuclear Cell Assay

Human peripheral blood mononuclear cells (PMBCs) were obtained from heparinized whole blood (healthy donors) by density gradient centrifugation using Lymphoprep (StemCell Technologies, Vancouver, BC) according to the manufacturers instructions. The PBMCs were washed twice with PBS containing 2 mM EDTA and 2% fetal calf serum (FCS) and reconstituted in RPMI containing 10% FCS and 2% PenStrep at a final concentration of 3 million cells/mL. This cell suspension (100 µL) was aliquoted into the wells of a 96-well flat bottom tissue culture plate. 5 µL of bicycle peptide or vehicle (0.1% DMSO in complete medium) was then added and mixed with 5 µL of TSLPvehicle (complete medium). The final concentration of TSLP (100 ng/mL) in the assay was 50, 400 or 666 µM. The plate was incubated for 30 minutes are rt. 10 µL of this mixture was added to cells and the plate was incubated for 24 hours in a 10% $CO_2$, humidified incubator at 37° C. The plate was centrifuged at 300×g for 5 min and the collected supernatants frozen at −20° C. for subsequent CCL17/TARC analysis.

CCL17/TARC was determined by MSD (MesoScale Discovery, Maryland, USA) according to the manufacturer's instructions.

The compound inhibition effect for the tested compounds was calculated using GraphPad Prism software using the following calculation method;

Compound % effect=100*[(X−min)/(max−min)], where X represents the normalized value for the compound based on the Min (DMSO) and Max (TSLP at 50, 400 or 666 µM).

Certain compounds of the invention were tested in the above mentioned CCL17 binding assay and the results are shown in Table 8 below.

TABLE 8

CCL17 Binding Data for Peptide Ligands of the Invention

| Example Number | CCL17 % Inhibition @ 10 µM | | |
|---|---|---|---|
| | 50 pM TSLP | 400 pM TSLP | 666 pM TSLP |
| 4 | 47 | | |
| 8 | 71 | | |
| 10 | 58 | | 56 |
| 11 | | | 43 |
| 14 | | | 14 |
| 15 | 58 | 64 | |
| 16 | | | 52 |
| 17 | 1 | | |
| 18 | 89 | | |
| 22 | 41 | | |
| 25 | 71 | | |
| 27 | | | 33 |
| 29 | 61 | 62 | |
| 32 | | | 14 |
| 36 | 58 | | |
| 42 | <20 | | 47 |
| 44 | | | 52 |
| 45 | | | 0 |
| 47 | | | −7 |
| 50 | | | 33 |
| 53 | | | −2 |
| 56 | | | 40 |
| 59 | | | 2 |
| 63 | | | 24 |
| 68 | | | 33 |
| 73 | | | −11 |
| 74 | | | 43 |
| 75 | | | −2 |
| 76 | | | 0 |
| 79 | | | −18 |
| 164 | | | 0 |
| 165 | | | 33 |
| 171 | | | 36 |
| 186 | | | −1 |
| 187 | | | 11 |
| 188 | | | −4 |
| 193 | | | 47 |
| 199 | | | −3 |
| 200 | | | −42 |
| 221 | | | −10 |
| 250 | 83 | 59 | |
| 251 | 87 | 85 | |

The invention claimed is:
1. A peptide ligand specific for thymic stromal lymphopoietin (TSLP) comprising a polypeptide comprising at least three cysteine residues, separated by at least two loop sequences, and a molecular scaffold which forms covalent bonds with the cysteine residues of the polypeptide such that at least two polypeptide loops are formed on the molecular scaffold, wherein said peptide ligand comprises an amino acid sequence selected from:

```
                                          (SEQ ID NO: 1)
CQ[TrpMe][tBuA]QDC[TrpMe][ADMA]G[4F3ClPhe]C;

(SEQ ID NO: 2)
CQ[TrpMe][tBuA]QDC[TrpMe]ADMA]G[4-FPhe]C;

(SEQ ID NO: 3)
CQ[TrpMe][tBuA]EDC[TrpMe][ADMA]G[4-FPhe]C;

(SEQ ID NO: 4)
CQW[tBuA]EDCWRG[4-FPhe]C;

(SEQ ID NO: 5)
C[AMe][TrpMe][tBuA]Q[MeD]C[TrpMe][ADMA]G[4-FPhe]C;

(SEQ ID NO: 6)
CQWLEDCWRG[4F3ClPhe]C;

(SEQ ID NO: 7)
C[AMe][TrpMe][tBuA]QDC[TrpMe][LysMe3]G[4-FPhe]C;

(SEQ ID NO: 8)
CQWLQDCWRG[4-FPhe]C;

(SEQ ID NO: 9)
CQWLEDCWRG[3,4diClPhe]C;

(SEQ ID NO: 10)
C[AMe][TrpMe][tBuA]QDC[TrpMe][ChMeA]G[4-FPhe]C;

(SEQ ID NO: 11)
CQ[TrpMe]LEDC[TrpMe][ADMA]G[4-FPhe]C;

(SEQ ID NO: 12)
CQWLEDCWRG[4-ClPhe]C;

(SEQ ID NO: 13)
C[AMe][TrpMe][tBuA]QDC[TrpMe][ADMA]G[4-FPhe]C;

(SEQ ID NO: 14)
CQ[TrpMe]LEDC[TrpMe]RG[4-FPhe]C;

(SEQ ID NO: 15)
CQWLEDCWRG[4-FPhe]C;

(SEQ ID NO: 16)
C[AMe][TrpMe][tBuA]QDC[TrpMe][ADMA]G[4-FPhe]C;

(SEQ ID NO: 17)
CHWLEDCWRG[4-FPhe]C;

(SEQ ID NO: 18)
CQWLQDCW[ADMA]G[4-FPhe]C;

(SEQ ID NO: 19)
CQ[5FTrp]LEDC[5FTrp]RG[4-FPhe]C;

(SEQ ID NO: 20)
CQWLEDCWRG[3,4diFPhe]C;

(SEQ ID NO: 21)
CQWLENCWRG[4-FPhe]C;

(SEQ ID NO: 22)
C[AMe][TrpMe][tBuA]QDC[TrpMe][AcK]G[4-FPhe]C;

(SEQ ID NO: 23)
C[AMe][Nal1][tBuA]QDC[TrpMe][ADMA]G[4-FPhe]C;

(SEQ ID NO: 24)
CQWLEDCWRG[4-BrPhe]C;

(SEQ ID NO: 25)
CQ[Nal1]LEDCWRG[4-FPhe]C;

(SEQ ID NO: 26)
CWWLQDCW[ADMA]G[4-FPhe]C;

(SEQ ID NO: 27)
C[AMe]WLEDCW[ADMA]G[4-FPhe]C;

(SEQ ID NO: 28)
CQW[iPrMeA]EDCWRG[4-FPhe]C;

(SEQ ID NO: 29)
CQWLEDCWRG[3-ClPhe]C;

(SEQ ID NO: 30)
C[AMe][TrpMe][tBuA]QDC[TrpMe][NeopentA]G[4-FPhe]C;

(SEQ ID NO: 31)
C[AMe][TrpMe][tBuA]QDC[TrpMe][Cha]G[4-FPhe]C;

(SEQ ID NO: 32)
C[AMe][Nal1]LQDC[TrpMe][ADMA]G[4-FPhe]C;

(SEQ ID NO: 33)
CQWLEDCWRG[3,4,5triFPhe]C;

(SEQ ID NO: 34)
CQ[Nal1]LEDCW[ADMA]G[4-FPhe]C;

(SEQ ID NO: 35)
CQWLFDCWRG[4-FPhe]C;

(SEQ ID NO: 36)
C[AMe][TrpMe][tBuA]QDC[5FTrp]RG[4-FPhe]C;

(SEQ ID NO: 37)
CQWLEDCWRG[3-F,4-ClPhe]C;

(SEQ ID NO: 38)
CQWLEDCWRGFC;

(SEQ ID NO: 39)
CQW[tBuA]EDCWRGFC;

(SEQ ID NO: 40)
C[AMe][TrpMe][tBuA]QDC[TrpMe][BnA]G[4-FPhe]C;

(SEQ ID NO: 41)
CQWLEDCWRG[Nal1]C;

(SEQ ID NO: 42)
CQWLEDCWRG[Nal2]C;

(SEQ ID NO: 43)
CQWMEDCWRG[4-FPhe]C;

(SEQ ID NO: 44)
C[AMe][TrpMe][tBuA][Aib]DC[TrpMe][ADMA]G[4-FPhe]C;

(SEQ ID NO: 45)
CQWIEDCWRG[4-FPhe]C;

(SEQ ID NO: 46)
CQWLEDCWRG[3,5diF, 4ClPhe]C;

(SEQ ID NO: 47)
CQWLEDC[4-ClNal]RG[4-FPhe]C;

(SEQ ID NO: 48)
CA[Nal1]LEDCW[Harg]G[4-FPhe]C;

(SEQ ID NO: 49)
CTWLEDCWRGFC;

(SEQ ID NO: 50)
CQW[CpentA]EDCWRGFC;
```

CAWLEDC[Nal1]RG[4-FPhe]C; (SEQ ID NO: 51)

CQWLEDCW[4-PipA]G[4-FPhe]C; (SEQ ID NO: 52)

C[AMe][TrpMe][tBuA]QDC[TrpMe][ADMA]G[4-ClNal]C; (SEQ ID NO: 53)

CVWLDDCWRGFC; (SEQ ID NO: 54)

CQWLEDCWRG[3-MePhe]C; (SEQ ID NO: 55)

CHWLEDCWRGFC; (SEQ ID NO: 56)

CTWLDDCWRGFC; (SEQ ID NO: 57)

CQWLEDCWRG[4-CF3Phe]C; (SEQ ID NO: 58)

CQWLEDCWRa[4-FPhe]C; (SEQ ID NO: 59)

CQW[CproA]EDCWRGFC; (SEQ ID NO: 60)

CQWLEDCW[TriMeK]GFC; (SEQ ID NO: 61)

CQWLEDCW[ADMA]GFC; (SEQ ID NO: 62)

CQW[Cha]EDCWRGFC; (SEQ ID NO: 63)

CHWLENCWRGFC; (SEQ ID NO: 64)

CLWLDDCWRGFC; (SEQ ID NO: 65)

C[AMe][TrpMe[tBuA]QDC[TrpMe][ADMA]G[3AcNH4ClPhe]C; (SEQ ID NO: 66)

CTWLEDCWHGFC; (SEQ ID NO: 67)

CQW[Nva]EDCWRGFC; (SEQ ID NO: 68)

CQWLEDCWRG[3-FPhe]C; (SEQ ID NO: 69)

CQWLEDCWRG[4-MePhe]C; (SEQ ID NO: 70)

CQW[ChMeA]EDCWRGFC; (SEQ ID NO: 71)

CHWLDDCWRGFC; (SEQ ID NO: 72)

CDWLDDCWRGFC; (SEQ ID NO: 73)

CDWLEDCWRGFC; (SEQ ID NO: 74)

CEWLEDCWRGFC; (SEQ ID NO: 75)

CQWLEDCW[Cit]GFC; (SEQ ID NO: 76)

CQWL[3-ClPhe]DCWRG[4-FPhe]C; (SEQ ID NO: 77)

CAWLTDCWRGFC; (SEQ ID NO: 78)

CQWLEDC[7-OMeTrp]RG[4-FPhe]C; (SEQ ID NO: 79)

CQW[Nle]EDCWRGFC; (SEQ ID NO: 80)

CQWLEDCWRG[2-FPhe]C; (SEQ ID NO: 81)

CQW[TriFMeA]EDCWRGFC; (SEQ ID NO: 82)

CQWLEDCW[HArg]GFC; (SEQ ID NO: 83)

CQWLEDCWRG[Cha]C; (SEQ ID NO: 84)

CA[Nal1]LEDC[Nal1][HArg]G[4-FPhe]C; (SEQ ID NO: 85)

CRWLDDCWQGFC; (SEQ ID NO: 86)

CQWLQDCFRG[4-FPhe]C; (SEQ ID NO: 87)

CQWLEDCWRG[4-CNPhe]C; (SEQ ID NO: 88)

CNWLEDCWHGFC; (SEQ ID NO: 89)

C[dA]WLEDCWRG[4-FPhe]C; (SEQ ID NO: 90)

CQWLEDCWRG[3-CNPhe]C; (SEQ ID NO: 91)

CQWLEDCW[Can]GFC; (SEQ ID NO: 92)

CQWLEDCWRG[3-ThienylA]C; (SEQ ID NO: 93)

CQWLEDCW[Agb]GFC; (SEQ ID NO: 94)

C[dA]WLEDCW[ADMA]G[4-FPhe]C; (SEQ ID NO: 95)

CQWLEDCWRG[2ThienylA]C; (SEQ ID NO: 96)

CEWLEDCWKGFC; (SEQ ID NO: 97)

CFWLEDCWRGYC; (SEQ ID NO: 98)

CQWLEDCWRGWC; (SEQ ID NO: 99)

CDWLDDCWKGFC; (SEQ ID NO: 100)

CQWLEDCWRG[4-MeOPhe]C; (SEQ ID NO: 101)

CQWLEDCWRG[3-BrPhe]C; (SEQ ID NO: 102)

CWWL[3-ClPhe]DCWRG[4-FPhe]C; (SEQ ID NO: 103)

CQ[ButG]LEDCW[ButG]G[4-FPhe]C; (SEQ ID NO: 104)

CQWLEDCWRG[2PyrA]C; (SEQ ID NO: 105)

CQW[M(O)]EDCWRGFC; (SEQ ID NO: 106)

CQWLEDCWRG[BnA]C; (SEQ ID NO: 107)

CQWLEDCWAGFC; (SEQ ID NO: 108)

CTILEDCWMGFC; (SEQ ID NO: 109)

CQW[Abu]EDCWRGFC; (SEQ ID NO: 110)

CHWLENCWAGFC; (SEQ ID NO: 111)

CQWLEDCWRG[PentFPhe]C; (SEQ ID NO: 112)

CQW[LMe]EDCWRG[4-FPhe]C; (SEQ ID NO: 113)

CQWLEDCW[Dap]GFC; (SEQ ID NO: 114)

CQWLEDCWRG[4-PyrA]C; (SEQ ID NO: 115)

CQWLEDCWRG[3-PyrA]C; (SEQ ID NO: 116)

CHWLENCW[Dap]GFC; (SEQ ID NO: 117)

CQW[4-MenL]EDCWRG[4-FPhe]C; (SEQ ID NO: 118)

CESLDPWSCPVWWRC; (SEQ ID NO: 119)

CPSLDPWTCQSWYEC; (SEQ ID NO: 120)

CTELDPWTCETWWLC; (SEQ ID NO: 121)

CRDLDPWTCSSWWLC; (SEQ ID NO: 122)

CADLDPWTCPNWWLC; (SEQ ID NO: 123)

CVDLDPWTCEQWWLC; (SEQ ID NO: 124)

CKDLDPWTCSSWWEC; (SEQ ID NO: 125)

CRDLDPWTCPTWWTC; (SEQ ID NO: 126)

CTDLDPWTCNSWWLC; (SEQ ID NO: 127)

CRDLDPWTCEEWWLC; (SEQ ID NO: 128)

CRELDPWTCETWWLC; (SEQ ID NO: 129)

CKELDPWTCETWWLC; (SEQ ID NO: 130)

C[Orn]ELDPWTCETWWLC; (SEQ ID NO: 131)

CQELDPWTCETWWLC; (SEQ ID NO: 132)

CTELD[diF-P]WTCETWWLC; (SEQ ID NO: 133)

CVDLDPWSCEDWWLC; (SEQ ID NO: 134)

CPDLDPWTCPLWWTC; (SEQ ID NO: 135)

CPDLDPWTCSDWWLC; (SEQ ID NO: 136)

CRDLDPWTCDSWWLC; (SEQ ID NO: 137)

CTDLDPWTCPDWWLC; (SEQ ID NO: 138)

CTELD[5-Ph-P]WTCETWWLC; (SEQ ID NO: 139)

CTELD[Chx-P]WTCETWWLC; (SEQ ID NO: 140)

CDWQWSYDCWLPC; (SEQ ID NO: 141)

CDWVWEYDCWLPC; (SEQ ID NO: 142)

CDWDWEYDCWLHC; (SEQ ID NO: 143)

CDWHWEYDCWLSC; (SEQ ID NO: 144)

CTWNWEYDCWLDC; (SEQ ID NO: 145)

CEWNWAYDCWLGC; (SEQ ID NO: 146)

CEWNWEYDCWLDC; (SEQ ID NO: 147)

CQWNWTYDCWLGC; (SEQ ID NO: 148)

CKWMWEYDCWLSC; (SEQ ID NO: 149)

CDWQWEYDCWLSC; (SEQ ID NO: 150)

CDWNWTYDCWLDC; (SEQ ID NO: 151)

CDWNWSYDCWLPC; (SEQ ID NO: 152)

CDWDWDYDCWLPC; (SEQ ID NO: 153)

CVWHWEYDCWLDC; (SEQ ID NO: 154)

CIWDWKYDCWLGC; (SEQ ID NO: 155)

CSLDPWSCHNWWTC;  (SEQ ID NO: 156)

CALDPWVCPQWWDC;  (SEQ ID NO: 157)

CQEHDWYCLLYQPEC;  (SEQ ID NO: 158)
and

CDELDIPCWIFKTLC;  (SEQ ID NO: 159)

of a pharmaceutically acceptable salt thereof.

2. The peptide ligand as defined in claim 1, wherein said peptide ligand comprises an amino acid sequence selected from:

Ac-(SEQ ID NO: 1) (hereinafter referred to as Example 1);
Ac-(SEQ ID NO: 2) (hereinafter referred to as Example 2);
Ac-(SEQ ID NO: 3) (hereinafter referred to as Example 3);
tertBuCO-(SEQ ID NO: 3) (hereinafter referred to as Example 6);
R$^1$-(SEQ ID NO: 3) (hereinafter referred to as Example 7);
Ac-(SEQ ID NO: 4) (hereinafter referred to as Example 4);
Ac-(SEQ ID NO: 5) (hereinafter referred to as Example 5);
Ac-(SEQ ID NO: 6) (hereinafter referred to as Example 8);
Ac-(SEQ ID NO: 7) (hereinafter referred to as Example 9);
Ac-(SEQ ID NO: 8) (hereinafter referred to as Example 10);
Ac-(SEQ ID NO: 9) (hereinafter referred to as Example 11);
Ac-(SEQ ID NO: 10) (hereinafter referred to as Example 12);
Ac-(SEQ ID NO: 11) (hereinafter referred to as Example 13);
Ac-(SEQ ID NO: 12) (hereinafter referred to as Example 14);
Octanoyl-(SEQ ID NO: 13) (hereinafter referred to as Example 15);
Ac-(SEQ ID NO: 14) (hereinafter referred to as Example 16);
Ac-(SEQ ID NO: 15) (hereinafter referred to as Example 17);
Ac-(SEQ ID NO: 15)-[dA] (hereinafter referred to as Example 33);
(SEQ ID NO: 15)-COOH (hereinafter referred to as Example 48);
Ac-(SEQ ID NO: 16) (hereinafter referred to as Example 18);
Ac-(SEQ ID NO: 17) (hereinafter referred to as Example 19);
Ac-(SEQ ID NO: 18) (hereinafter referred to as Example 20);
Ac-(SEQ ID NO: 19) (hereinafter referred to as Example 21);
Ac-(SEQ ID NO: 20) (hereinafter referred to as Example 22);
Ac-(SEQ ID NO: 21) (hereinafter referred to as Example 23);
Ac-(SEQ ID NO: 22) (hereinafter referred to as Example 24);
(SEQ ID NO: 23) (hereinafter referred to as Example 252);
Ac-(SEQ ID NO: 23) (hereinafter referred to as Example 25);
Ac-(SEQ ID NO: 23)-[dA] (hereinafter referred to as Example 29);
Ac-(SEQ ID NO: 24) (hereinafter referred to as Example 26);
Ac-(SEQ ID NO: 25) (hereinafter referred to as Example 27);
Ac-(SEQ ID NO: 26) (hereinafter referred to as Example 28);
Ac-(SEQ ID NO: 27) (hereinafter referred to as Example 30);
Ac-(SEQ ID NO: 28) (hereinafter referred to as Example 31);
Ac-(SEQ ID NO: 29) (hereinafter referred to as Example 32);
Ac-(SEQ ID NO: 30) (hereinafter referred to as Example 34);
Ac-(SEQ ID NO: 31) (hereinafter referred to as Example 35);
Ac-(SEQ ID NO: 32) (hereinafter referred to as Example 36);
Ac-(SEQ ID NO: 33) (hereinafter referred to as Example 37);
Ac-(SEQ ID NO: 34) (hereinafter referred to as Example 38);
Ac-(SEQ ID NO: 34)-[dA] (hereinafter referred to as Example 49);
Ac-(SEQ ID NO: 34)-COOH (hereinafter referred to as Example 69);
Ac-(SEQ ID NO: 35) (hereinafter referred to as Example 43);
Ac-(SEQ ID NO: 35)-COOH (hereinafter referred to as Example 39);
Ac-(SEQ ID NO: 36) (hereinafter referred to as Example 40);
Ac-(SEQ ID NO: 37) (hereinafter referred to as Example 41);
A-(SEQ ID NO: 38)-ADGDML (hereinafter referred to as Example 42);
GTDSAE-(SEQ ID NO: 38)-A (hereinafter referred to as Example 45);
Ac-A-(SEQ ID NO: 38)-PLD (hereinafter referred to as Example 53);
Ac-(SEQ ID NO: 38)-APDERD (hereinafter referred to as Example 54);
A-(SEQ ID NO: 38)-DDAHAP (hereinafter referred to as Example 55);
TMEYRD-(SEQ ID NO: 38)-A (hereinafter referred to as Example 56);
A-(SEQ ID NO: 38)-SSSDQS (hereinafter referred to as Example 59);
SDEQRT-(SEQ ID NO: 38)-A (hereinafter referred to as Example 61);
DDEITQ-(SEQ ID NO: 38)-A (hereinafter referred to as Example 64);
RTDETG-(SEQ ID NO: 38)-A (hereinafter referred to as Example 67);
A-(SEQ ID NO: 38)-A (hereinafter referred to as Example 68);
ETNNLE-(SEQ ID NO: 38)-A (hereinafter referred to as Example 71);

Ac-(SEQ ID NO: 38) (hereinafter referred to as Example 79);
DPPKPR-(SEQ ID NO: 38)-A (hereinafter referred to as Example 87);
(SEQ ID NO: 38)-DTSTHS (hereinafter referred to as Example 128);
Ac-(SEQ ID NO: 39) (hereinafter referred to as Example 44);
Ac-(SEQ ID NO: 40) (hereinafter referred to as Example 46);
Ac-(SEQ ID NO: 41) (hereinafter referred to as Example 47);
Ac-(SEQ ID NO: 42) (hereinafter referred to as Example 50);
Ac-(SEQ ID NO: 43) (hereinafter referred to as Example 51);
Ac-(SEQ ID NO: 44) (hereinafter referred to as Example 52);
Ac-(SEQ ID NO: 45) (hereinafter referred to as Example 57);
Ac-(SEQ ID NO: 46) (hereinafter referred to as Example 58);
Ac-(SEQ ID NO: 47) (hereinafter referred to as Example 60);
Ac-(SEQ ID NO: 48) (hereinafter referred to as Example 62);
A-(SEQ ID NO: 49)-ADS (hereinafter referred to as Example 63);
Ac-(SEQ ID NO: 50) (hereinafter referred to as Example 65);
Ac-(SEQ ID NO: 51) (hereinafter referred to as Example 66);
Ac-(SEQ ID NO: 52) (hereinafter referred to as Example 70);
Ac-(SEQ ID NO: 53) (hereinafter referred to as Example 72);
SPP-(SEQ ID NO: 54)-A (hereinafter referred to as Example 73);
Ac-(SEQ ID NO: 55) (hereinafter referred to as Example 74);
A-(SEQ ID NO: 56)-HLE (hereinafter referred to as Example 75);
A-(SEQ ID NO: 57)-A (hereinafter referred to as Example 76);
Ac-(SEQ ID NO: 58) (hereinafter referred to as Example 77);
Ac-(SEQ ID NO: 59) (hereinafter referred to as Example 78);
Ac-(SEQ ID NO: 60) (hereinafter referred to as Example 80);
Ac-(SEQ ID NO: 61) (hereinafter referred to as Example 81);
Ac-(SEQ ID NO: 62) (hereinafter referred to as Example 82);
Ac-(SEQ ID NO: 63) (hereinafter referred to as Example 83);
tertBuCO-(SEQ ID NO: 64) (hereinafter referred to as Example 84);
$R^1$-(SEQ ID NO: 64) (hereinafter referred to as Example 89);
$R^2$-(SEQ ID NO: 64) (hereinafter referred to as Example 95);
Benzyl-(SEQ ID NO: 64) (hereinafter referred to as Example 93);
Ac-(SEQ ID NO: 64)-[N-phenethylamide] (hereinafter referred to as Example 96);
$R^3$-(SEQ ID NO: 64) (hereinafter referred to as Example 99);
$R^4$-(SEQ ID NO: 64) (hereinafter referred to as Example 103);
Ac-(SEQ ID NO: 64)-[N-benzylamide] (hereinafter referred to as Example 109);
A-(SEQ ID NO: 64)-A (hereinafter referred to as Example 115);
Benzoyl-(SEQ ID NO: 64) (hereinafter referred to as Example 116);
Ac-(SEQ ID NO: 64)-$R^5$ (hereinafter referred to as Example 120);
Succinyl-(SEQ ID NO: 64) (hereinafter referred to as Example 121);
Ac-(SEQ ID NO: 64)-[N-octylamide] (hereinafter referred to as Example 122);
Ac-(SEQ ID NO: 64)-[N-pentylamide] (hereinafter referred to as Example 123);
Ac-(SEQ ID NO: 64) (hereinafter referred to as Example 124);
Ac-(SEQ ID NO: 64)-$R^6$ (hereinafter referred to as Example 127);
(SEQ ID NO: 64) (hereinafter referred to as Example 129);
Decanoyl-(SEQ ID NO: 64) (hereinafter referred to as Example 137);
Hexanoyl-(SEQ ID NO: 64) (hereinafter referred to as Example 139);
SPT-(SEQ ID NO: 65)-A (hereinafter referred to as Example 85);
Ac-(SEQ ID NO: 66) (hereinafter referred to as Example 86);
TIK-(SEQ ID NO: 67)-A (hereinafter referred to as Example 88);
Ac-(SEQ ID NO: 68) (hereinafter referred to as Example 90);
Ac-(SEQ ID NO: 69) (hereinafter referred to as Example 91);
Ac-(SEQ ID NO: 70) (hereinafter referred to as Example 92);
Ac-(SEQ ID NO: 71) (hereinafter referred to as Example 94);
DNH-(SEQ ID NO: 72)-A (hereinafter referred to as Example 97);
HPN-(SEQ ID NO: 73)-A (hereinafter referred to as Example 98);
Ac-(SEQ ID NO: 74)-TTS (hereinafter referred to as Example 100);
A-(SEQ ID NO: 75)-A (hereinafter referred to as Example 101);
(SEQ ID NO: 76) (hereinafter referred to as Example 102);
Ac-(SEQ ID NO: 76) (hereinafter referred to as Example 104);
Ac-(SEQ ID NO: 77) (hereinafter referred to as Example 105);
DQD-(SEQ ID NO: 78)-A (hereinafter referred to as Example 106);
Ac-(SEQ ID NO: 79) (hereinafter referred to as Example 107);
Ac-(SEQ ID NO: 80) (hereinafter referred to as Example 108);
Ac-(SEQ ID NO: 81) (hereinafter referred to as Example 110);
Ac-(SEQ ID NO: 82) (hereinafter referred to as Example 111);

Ac-(SEQ ID NO: 83) (hereinafter referred to as Example 112);
Ac-(SEQ ID NO: 84) (hereinafter referred to as Example 113);
Ac-(SEQ ID NO: 85) (hereinafter referred to as Example 114);
REN-(SEQ ID NO: 86)-A (hereinafter referred to as Example 117);
Ac-(SEQ ID NO: 87) (hereinafter referred to as Example 118);
Ac-(SEQ ID NO: 88) (hereinafter referred to as Example 119);
A-(SEQ ID NO: 89)-HEE (hereinafter referred to as Example 125);
Ac-(SEQ ID NO: 90) (hereinafter referred to as Example 126);
Ac-(SEQ ID NO: 91) (hereinafter referred to as Example 130);
Ac-(SEQ ID NO: 92) (hereinafter referred to as Example 131);
Ac-(SEQ ID NO: 93) (hereinafter referred to as Example 132);
Ac-(SEQ ID NO: 94) (hereinafter referred to as Example 133);
Ac-(SEQ ID NO: 95) (hereinafter referred to as Example 134);
Ac-(SEQ ID NO: 96) (hereinafter referred to as Example 135);
A-(SEQ ID NO: 97)-HSE (hereinafter referred to as Example 136);
A-(SEQ ID NO: 98)-ETA (hereinafter referred to as Example 138);
Ac-(SEQ ID NO: 99) (hereinafter referred to as Example 140);
A-(SEQ ID NO: 100)-A (hereinafter referred to as Example 141);
Ac-(SEQ ID NO: 101) (hereinafter referred to as Example 142);
Ac-(SEQ ID NO: 102) (hereinafter referred to as Example 143);
Ac-(SEQ ID NO: 103) (hereinafter referred to as Example 144);
Ac-(SEQ ID NO: 104) (hereinafter referred to as Example 145);
Ac-(SEQ ID NO: 105) (hereinafter referred to as Example 146);
Ac-(SEQ ID NO: 106) (hereinafter referred to as Example 147);
Ac-(SEQ ID NO: 107) (hereinafter referred to as Example 148);
Ac-(SEQ ID NO: 108) (hereinafter referred to as Example 149);
A-(SEQ ID NO: 109)-A (hereinafter referred to as Example 150);
Ac-(SEQ ID NO: 110) (hereinafter referred to as Example 151);
Ac-(SEQ ID NO: 111) (hereinafter referred to as Example 152);
Ac-(SEQ ID NO: 112) (hereinafter referred to as Example 153);
Ac-(SEQ ID NO: 113) (hereinafter referred to as Example 154);
Ac-(SEQ ID NO: 114) (hereinafter referred to as Example 155);
(SEQ ID NO: 114) (hereinafter referred to as Example 156);
Ac-(SEQ ID NO: 115) (hereinafter referred to as Example 157);
Ac-(SEQ ID NO: 116) (hereinafter referred to as Example 158);
Ac-(SEQ ID NO: 117) (hereinafter referred to as Example 159); and
Ac-(SEQ ID NO: 118) (hereinafter referred to as Example 160);

wherein Ac represents acetyl, tertBuCO represents

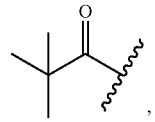, $R^1$ represents:

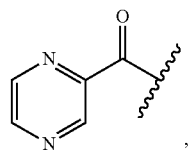 [SMILES: *C(=O)c1cnccn1], $R^2$ represents:

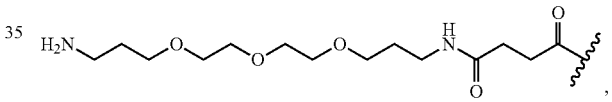, $R^3$ represents:

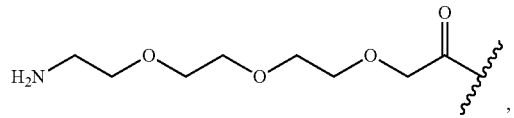 [SMILES: *C(=O)COCCOCCOCCN], $R^4$ represents:

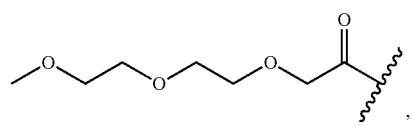 [SMILES: *C(=O)COCCOCCOC], $R^5$ represents:

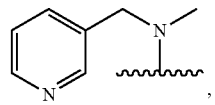 [SMILES: *N(C)Cc1cccnc1], and
R⁶ represents:

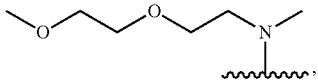

or a pharmaceutically acceptable salt thereof.

3. The peptide ligand as defined in claim 1, wherein said peptide ligand comprises an amino acid sequence selected from:
- A-(SEQ ID NO: 119)-A (hereinafter referred to as Example 161);
- A-(SEQ ID NO: 120)-A (hereinafter referred to as Example 162);
- A-(SEQ ID NO: 121)-A (hereinafter referred to as Example 163);
- (SEQ ID NO: 121) (hereinafter referred to as Example 185);
- A-(SEQ ID NO: 122)-A (hereinafter referred to as Example 164);
- YATTQV-(SEQ ID NO: 122)-A (hereinafter referred to as Example 171);
- KDNRVD-(SEQ ID NO: 122)-A (hereinafter referred to as Example 172);
- EYQRDV-(SEQ ID NO: 122)-A (hereinafter referred to as Example 173);
- A-(SEQ ID NO: 122)-SNSYDMA (hereinafter referred to as Example 174);
- A-(SEQ ID NO: 122)-SESVHTA (hereinafter referred to as Example 175);
- A-(SEQ ID NO: 122)-SSDTHDA (hereinafter referred to as Example 176);
- A-(SEQ ID NO: 122)-KPDHVDA (hereinafter referred to as Example 177);
- A-(SEQ ID NO: 122)-ANY (hereinafter referred to as Example 186);
- RVNTHQ-(SEQ ID NO: 122)-A (hereinafter referred to as Example 190);
- YDRDFT-(SEQ ID NO: 122)-A (hereinafter referred to as Example 191);
- EVDTYP-(SEQ ID NO: 122)-A (hereinafter referred to as Example 192);
- A-(SEQ ID NO: 122)-ADGLYDA (hereinafter referred to as Example 193);
- AHP-(SEQ ID NO: 123)-A (hereinafter referred to as Example 165);
- YGA-(SEQ ID NO: 124)-A (hereinafter referred to as Example 166);
- A-(SEQ ID NO: 125)-APN (hereinafter referred to as Example 167);
- A-(SEQ ID NO: 126)-YDE (hereinafter referred to as Example 168);
- A-(SEQ ID NO: 127)-AGD (hereinafter referred to as Example 169);
- A-(SEQ ID NO: 128)-AHP (hereinafter referred to as Example 170);
- (SEQ ID NO: 129) (hereinafter referred to as Example 178);
- (SEQ ID NO: 130) (hereinafter referred to as Example 179);
- (SEQ ID NO: 131) (hereinafter referred to as Example 180);
- (SEQ ID NO: 132) (hereinafter referred to as Example 181);
- (SEQ ID NO: 133) (hereinafter referred to as Example 182);
- A-(SEQ ID NO: 134)-A (hereinafter referred to as Example 183);
- A-(SEQ ID NO: 135)-A (hereinafter referred to as Example 184);
- RAP-(SEQ ID NO: 136)-A (hereinafter referred to as Example 187);
- SHV-(SEQ ID NO: 137)-A (hereinafter referred to as Example 188);
- RDL-(SEQ ID NO: 138)-A (hereinafter referred to as Example 189);
- (SEQ ID NO: 139) (hereinafter referred to as Example 194); and
- (SEQ ID NO: 140) (hereinafter referred to as Example 195);

or a pharmaceutically acceptable salt thereof.

4. The peptide ligand as defined in claim 1, wherein said peptide ligand comprises an amino acid sequence selected from:
- A-(SEQ ID NO: 141)-A (hereinafter referred to as Example 196);
- A-(SEQ ID NO: 142)-A (hereinafter referred to as Example 197);
- A-(SEQ ID NO: 143)-A (hereinafter referred to as Example 198);
- A-(SEQ ID NO: 144)-A (hereinafter referred to as Example 199);
- DEQHHE-(SEQ ID NO: 144)-A (hereinafter referred to as Example 209);
- SNATKQ-(SEQ ID NO: 144)-A (hereinafter referred to as Example 210);
- GNIKKS-(SEQ ID NO: 144)-A (hereinafter referred to as Example 211);
- A-(SEQ ID NO: 144)-DPSSKQA (hereinafter referred to as Example 212);
- A-(SEQ ID NO: 144)-YDNEMSA (hereinafter referred to as Example 213);
- SEAQET-(SEQ ID NO: 144) (hereinafter referred to as Example 214);
- SPTEPP-(SEQ ID NO: 144) (hereinafter referred to as Example 215);
- (SEQ ID NO: 144)-EPETGQ (hereinafter referred to as Example 216);
- NRSPSE-(SEQ ID NO: 144) (hereinafter referred to as Example 217);
- Ac-(SEQ ID NO: 144) (hereinafter referred to as Example 218);
- R⁷-(SEQ ID NO: 144) (hereinafter referred to as Example 219);
- A-(SEQ ID NO: 144)-EPETGQA (hereinafter referred to as Example 221);
- (SEQ ID NO: 144)-GDMSVS (hereinafter referred to as Example 222);
- (SEQ ID NO: 144)-YDNEMS (hereinafter referred to as Example 223);
- (SEQ ID NO: 144)-APDHLP (hereinafter referred to as Example 224);
- (SEQ ID NO: 144)-DPSSKQ (hereinafter referred to as Example 226);
- (SEQ ID NO: 144)-ANSEFE (hereinafter referred to as Example 227);
- (SEQ ID NO: 144)-GAGESS (hereinafter referred to as Example 228);
- DHD-(SEQ ID NO: 145)-A (hereinafter referred to as Example 200);

ADG-(SEQ ID NO: 146)-A (hereinafter referred to as Example 201);
TLP-(SEQ ID NO: 147)-A (hereinafter referred to as Example 202);
SQE-(SEQ ID NO: 148)-A (hereinafter referred to as Example 203);
AET-(SEQ ID NO: 149)-A (hereinafter referred to as Example 204);
A-(SEQ ID NO: 150)-DPN (hereinafter referred to as Example 205);
A-(SEQ ID NO: 151)-API (hereinafter referred to as Example 206);
A-(SEQ ID NO: 152)-ANT (hereinafter referred to as Example 207);
A-(SEQ ID NO: 153)-FAE (hereinafter referred to as Example 208);
AND-(SEQ ID NO: 154)-A (hereinafter referred to as Example 220); and
ERN-(SEQ ID NO: 155)-A (hereinafter referred to as Example 225);
wherein R⁷ represents

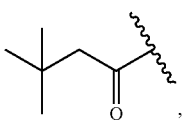 [SMILES: *C(=O)CC(C)(C)C]

or a pharmaceutically acceptable salt thereof.

5. The peptide ligand as defined in claim 1, wherein said peptide ligand comprises an amino acid sequence selected from:
A-(SEQ ID NO: 156)-A (hereinafter referred to as Example 229); and
A-(SEQ ID NO: 157)-A (hereinafter referred to as Example 230);
or a pharmaceutically acceptable salt thereof.

6. The peptide ligand as defined in claim 1, wherein said peptide ligand comprises an amino acid sequence selected from:
A-(SEQ ID NO: 158)-A (hereinafter referred to as Example 231); and
A-(SEQ ID NO: 159)-A (hereinafter referred to as Example 232);
or a pharmaceutically acceptable salt thereof.

7. A peptide ligand specific for thymic stromal lymphopoietin (TSLP) comprising a polypeptide comprising at least three cysteine residues, separated by at least two loop sequences, and a molecular scaffold which forms covalent bonds with the cysteine residues of the polypeptide such that at least two polypeptide loops are formed on the molecular scaffold, wherein said peptide ligand comprises an amino acid sequence selected from:

```
                                           (SEQ ID NO: 1)
CQ[TrpMe][tBuA]QDC[TrpMe][ADMA]G[4F3ClPhe]C;

(SEQ ID NO: 2)
CQ[TrpMe][tBuA]QDC[TrpMe]ADMA]G[4-FPhe]C;

(SEQ ID NO: 3)
CQ[TrpMe][tBuA]EDC[TrpMe][ADMA]G[4-FPhe]C;

(SEQ ID NO: 4)
CQW[tBuA]EDCWRG[4-FPhe]C;

(SEQ ID NO: 5)
C[AMe][TrpMe][tBuA]Q[MeD]C[TrpMe][ADMA]G[4-FPhe]C;

(SEQ ID NO: 6)
CQWLEDCWRG[4F3ClPhe]C;

(SEQ ID NO: 7)
C[AMe][TrpMe][tBuA]QDC[TrpMe][LysMe3]G[4-FPhe]C;

(SEQ ID NO: 8)
CQWLQDCWRG[4-FPhe]C;

(SEQ ID NO: 9)
CQWLEDCWRG[3,4diClPhe]C;

(SEQ ID NO: 10)
C[AMe][TrpMe][tBuA]QDC[TrpMe][ChMeA]G[4-FPhe]C;

(SEQ ID NO: 11)
CQ[TrpMe]LEDC[TrpMe][ADMA]G[4-FPhe]C;

(SEQ ID NO: 12)
CQWLEDCWRG[4-ClPhe]C;

(SEQ ID NO: 13)
C[AMe][TrpMe][tBuA]QDC[TrpMe][ADMA]G[4-FPhe]C;

(SEQ ID NO: 14)
CQ[TrpMe]LEDC[TrpMe]RG[4-FPhe]C;

(SEQ ID NO: 15)
CQWLEDCWRG[4-FPhe]C;

(SEQ ID NO: 16)
C[AMe][TrpMe][tBuA]QDC[TrpMe][ADMA]G[4-FPhe]C;

(SEQ ID NO: 17)
CHWLEDCWRG[4-FPhe]C;

(SEQ ID NO: 18)
CQWLQDCW[ADMA]G[4-FPhe]C;

(SEQ ID NO: 19)
CQ[5FTrp]LEDC[5FTrp]RG[4-FPhe]C;

(SEQ ID NO: 20)
CQWLEDCWRG[3,4diFPhe]C;

(SEQ ID NO: 21)
CQWLENCWRG[4-FPhe]C;

(SEQ ID NO: 22)
C[AMe][TrpMe][tBuA]QDC[TrpMe][AcK]G[4-FPhe]C;

(SEQ ID NO: 23)
C[AMe][Nal1][tBuA]QDC[TrpMe][ADMA]G[4-FPhe]C;

(SEQ ID NO: 24)
CQWLEDCWRG[4-BrPhe]C;

(SEQ ID NO: 25)
CQ[Nal1]LEDCWRG[4-FPhe]C;

(SEQ ID NO: 26)
CWWLQDCW[ADMA]G[4-FPhe]C;

(SEQ ID NO: 27)
C[AMe]WLEDCW[ADMA]G[4-FPhe]C;

(SEQ ID NO: 28)
CQW[iPrMeA]EDCWRG[4-FPhe]C;

(SEQ ID NO: 29)
CQWLEDCWRG[3-ClPhe]C;

(SEQ ID NO: 30)
C[AMe][TrpMe][tBuA]QDC[TrpMe][NeopentA]G[4-FPhe]C;

(SEQ ID NO: 31)
C[AMe][TrpMe][tBuA]QDC[TrpMe][Cha]G[4-FPhe]C;
```

C[AMe][Nal1]LQDC[TrpMe][ADMA]G[4-FPhe]C; (SEQ ID NO: 32)

CQWLEDCWRG[3,4,5triFPhe]C; (SEQ ID NO: 33)

CQ[Nal1]LEDCW[ADMA]G[4-FPhe]C; (SEQ ID NO: 34)

CQWLFDCWRG[4-FPhe]C; (SEQ ID NO: 35)

C[AMe][TrpMe][tBuA]QDC[5FTrp]RG[4-FPhe]C; (SEQ ID NO: 36)

CQWLEDCWRG[3-F,4-ClPhe]C; (SEQ ID NO: 37)

CQWLEDCWRGFC; (SEQ ID NO: 38)

CQW[tBuA]EDCWRGFC; (SEQ ID NO: 39)

C[AMe][TrpMe][tBuA]QDC[TrpMe][BnA]G[4-FPhe]C; (SEQ ID NO: 40)

CQWLEDCWRG[Nal1]C; (SEQ ID NO: 41)

CQWLEDCWRG[Nal2]C; (SEQ ID NO: 42)

CQWMEDCWRG[4-FPhe]C; (SEQ ID NO: 43)

C[AMe][TrpMe][tBuA][Aib]DC[TrpMe][ADMA]G[4-FPhe]C; (SEQ ID NO: 44)

CQWIEDCWRG[4-FPhe]C; (SEQ ID NO: 45)

CQWLEDCWRG[3,5diF,4ClPhe]C; (SEQ ID NO: 46)

CQWLEDC[4-ClNal]RG[4-FPhe]C; (SEQ ID NO: 47)

CA[Nal1]LEDCW[Harg]G[4-FPhe]C; (SEQ ID NO: 48)

CTWLEDCWRGFC; (SEQ ID NO: 49)

CQW[CpentA]EDCWRGFC; (SEQ ID NO: 50)

CAWLEDC[Nal1]RG[4-FPhe]C; (SEQ ID NO: 51)

CQWLEDCW[4-PipA]G[4-FPhe]C; (SEQ ID NO: 52)

C[AMe][TrpMe][tBuA]QDC[TrpMe][ADMA]G[4-ClNal]C; (SEQ ID NO: 53)

CVWLDDCWRGFC; (SEQ ID NO: 54)

CQWLEDCWRG[3-MePhe]C; (SEQ ID NO: 55)

CHWLEDCWRGFC; (SEQ ID NO: 56)

CTWLDDCWRGFC; (SEQ ID NO: 57)

CQWLEDCWRG[4-CF3Phe]C; (SEQ ID NO: 58)

CQWLEDCWRa[4-FPhe]C; (SEQ ID NO: 59)

CQW[CproA]EDCWRGFC; (SEQ ID NO: 60)

CQWLEDCW[TriMeK]GFC; (SEQ ID NO: 61)

CQWLEDCW[ADMA]GFC; (SEQ ID NO: 62)

CQW[Cha]EDCWRGFC; (SEQ ID NO: 63)

CHWLENCWRGFC; (SEQ ID NO: 64)

CLWLDDCWRGFC; (SEQ ID NO: 65)

C[AMe][TrpMe[tBuA]QDC[TrpMe][ADMA]G[3AcNH4ClPhe]C; (SEQ ID NO: 66)

CTWLEDCWHGFC; (SEQ ID NO: 67)

CQW[Nva]EDCWRGFC; (SEQ ID NO: 68)

CQWLEDCWRG[3-FPhe]C; (SEQ ID NO: 69)

CQWLEDCWRG[4-MePhe]C; (SEQ ID NO: 70)

CQW[ChMeA]EDCWRGFC; (SEQ ID NO: 71)

CHWLDDCWRGFC; (SEQ ID NO: 72)

CDWLDDCWRGFC; (SEQ ID NO: 73)

CDWLEDCWRGFC; (SEQ ID NO: 74)

CEWLEDCWRGFC; (SEQ ID NO: 75)

CQWLEDCW[Cit]GFC; (SEQ ID NO: 76)

CQWL[3-ClPhe]DCWRG[4-FPhe]C; (SEQ ID NO: 77)

CAWLTDCWRGFC; (SEQ ID NO: 78)

CQWLEDC[7-OMeTrp]RG[4-FPhe]C; (SEQ ID NO: 79)

CQW[Nle]EDCWRGFC; (SEQ ID NO: 80)

CQWLEDCWRG[2-FPhe]C; (SEQ ID NO: 81)

CQW[TriFMeA]EDCWRGFC; (SEQ ID NO: 82)

CQWLEDCW[HArg]GFC; (SEQ ID NO: 83)

CQWLEDCWRG[Cha]C; (SEQ ID NO: 84)

CA[Nal1]LEDC[Nal1][HArg]G[4-FPhe]C; (SEQ ID NO: 85)

CRWLDDCWQGFC; (SEQ ID NO: 86)

CQWLQDCFRG[4-FPhe]C; (SEQ ID NO: 87)

CQWLEDCWRG[4-CNPhe]C; (SEQ ID NO: 88)

CNWLEDCWHGFC; (SEQ ID NO: 89)

C[dA]WLEDCWRG[4-FPhe]C; (SEQ ID NO: 90)

CQWLEDCWRG[3-CNPhe]C; (SEQ ID NO: 91)

CQWLEDCW[Can]GFC; (SEQ ID NO: 92)

CQWLEDCWRG[3-ThienylA]C; (SEQ ID NO: 93)

CQWLEDCW[Agb]GFC; (SEQ ID NO: 94)

C[dA]WLEDCW[ADMA]G[4-FPhe]C; (SEQ ID NO: 95)

CQWLEDCWRG[2ThienylA]C; (SEQ ID NO: 96)

CEWLEDCWKGFC; (SEQ ID NO: 97)

CFWLEDCWRGYC; (SEQ ID NO: 98)

CQWLEDCWRGWC; (SEQ ID NO: 99)

CDWLDDCWKGFC; (SEQ ID NO: 100)

CQWLEDCWRG[4-MeOPhe]C; (SEQ ID NO: 101)

CQWLEDCWRG[3-BrPhe]C; (SEQ ID NO: 102)

CWWL[3-ClPhe]DCWRG[4-FPhe]C; (SEQ ID NO: 103)

CQ[ButG]LEDCW[ButG]G[4-FPhe]C; (SEQ ID NO: 104)

CQWLEDCWRG[2PyrA]C; (SEQ ID NO: 105)

CQW[M(O)]EDCWRGFC; (SEQ ID NO: 106)

CQWLEDCWRG[BnA]C; (SEQ ID NO: 107)

CQWLEDCWAGFC; (SEQ ID NO: 108)

CTILEDCWMGFC; (SEQ ID NO: 109)

CQW[Abu]EDCWRGFC; (SEQ ID NO: 110)

CHWLENCWAGFC; (SEQ ID NO: 111)

CQWLEDCWRG[PentFPhe]C; (SEQ ID NO: 112)

CQW[LMe]EDCWRG[4-FPhe]C; (SEQ ID NO: 113)

CQWLEDCW[Dap]GFC; (SEQ ID NO: 114)

CQWLEDCWRG[4-PyrA]C; (SEQ ID NO: 115)

CQWLEDCWRG[3-PyrA]C; (SEQ ID NO: 116)

CHWLENCW[Dap]GFC; (SEQ ID NO: 117)

CQW[4-MenL]EDCWRG[4-FPhe]C; (SEQ ID NO: 118)

CESLDPWSCPVWWRC; (SEQ ID NO: 119)

CPSLDPWTCQSWYEC; (SEQ ID NO: 120)

CTELDPWTCETWWLC; (SEQ ID NO: 121)

CRDLDPWTCSSWWLC; (SEQ ID NO: 122)

CADLDPWTCPNWWLC; (SEQ ID NO: 123)

CVDLDPWTCEQWWLC; (SEQ ID NO: 124)

CKDLDPWTCSSWWEC; (SEQ ID NO: 125)

CRDLDPWTCPTWWTC; (SEQ ID NO: 126)

CTDLDPWTCNSWWLC; (SEQ ID NO: 127)

CRDLDPWTCEEWWLC; (SEQ ID NO: 128)

CRELDPWTCETWWLC; (SEQ ID NO: 129)

CKELDPWTCETWWLC; (SEQ ID NO: 130)

C[Orn]ELDPWTCETWWLC; (SEQ ID NO: 131)

CQELDPWTCETWWLC; (SEQ ID NO: 132)

CTELD[diF-P]WTCETWWLC; (SEQ ID NO: 133)

CVDLDPWSCEDWWLC; (SEQ ID NO: 134)

CPDLDPWTCPLWWTC; (SEQ ID NO: 135)

CPDLDPWTCSDWWLC; (SEQ ID NO: 136)

CRDLDPWTCDSWWLC; (SEQ ID NO: 137)

CTDLDPWTCPDWWLC; (SEQ ID NO: 138)

CTELD[5-Ph-P]WTCETWWLC; (SEQ ID NO: 139)

CTELD[Chx-P]WTCETWWLC; (SEQ ID NO: 140)

CDWQWSYDCWLPC; (SEQ ID NO: 141)

CDWVWEYDCWLPC; (SEQ ID NO: 142)

CDWDWEYDCWLHC; (SEQ ID NO: 143)

CDWHWEYDCWLSC; (SEQ ID NO: 144)

CTWNWEYDCWLDC; (SEQ ID NO: 145)

CEWNWAYDCWLGC; (SEQ ID NO: 146)

CEWNWEYDCWLDC; (SEQ ID NO: 147)

CQWNWTYDCWLGC; (SEQ ID NO: 148)

CKWMWEYDCWLSC; (SEQ ID NO: 149)

CDWQWEYDCWLSC; (SEQ ID NO: 150)

CDWNWTYDCWLDC; (SEQ ID NO: 151)

CDWNWSYDCWLPC; (SEQ ID NO: 152)

CDWDWDYDCWLPC; (SEQ ID NO: 153)

CVWHWEYDCWLDC; (SEQ ID NO: 154)

CIWDWKYDCWLGC; (SEQ ID NO: 155)

CSLDPWSCHNWWTC; (SEQ ID NO: 156)

CALDPWVCPQWWDC; (SEQ ID NO: 157)

CQEHDWYCLLYQPEC; (SEQ ID NO: 158)

CDELDIPCWIFKTLC; (SEQ ID NO: 159)

CQ[modG]LEDCW[modG]G[4-FPhe]C; (SEQ ID NO: 160)

CQ[modG][tBuA]EDC[TrpMe][modG]G[4-FPhe]C; (SEQ ID NO: 161)

CQ[modG][tBuA]QDC[TrpMe][modG]G[4-FPhe]C; (SEQ ID NO: 162)

C[NMeA][modG][tBuA]QDC[TrpMe][modG]G[4-FPhe]C; (SEQ ID NO: 163)

Ac-(SEQ ID NO: 160);
Ac-(SEQ ID NO: 161);
Ac-(SEQ ID NO: 161)-A;
Ac-(SEQ ID NO: 162); and
Ac-(SEQ ID NO: 163);

wherein Ac represents acetyl, and modG represents a modified glycine residue, wherein two modG in an amino acid sequence are linked by a linker moiety, or a pharmaceutically acceptable salt thereof.

8. A multimeric binding complex comprising at least two peptide ligands, wherein each of said at least two peptide ligands is as defined in claim 1, and wherein said at least two peptide ligands may be the same or different.

9. The multimeric binding complex as defined in claim 8, wherein said multimeric binding complex comprises a dimeric or trimeric moiety selected from

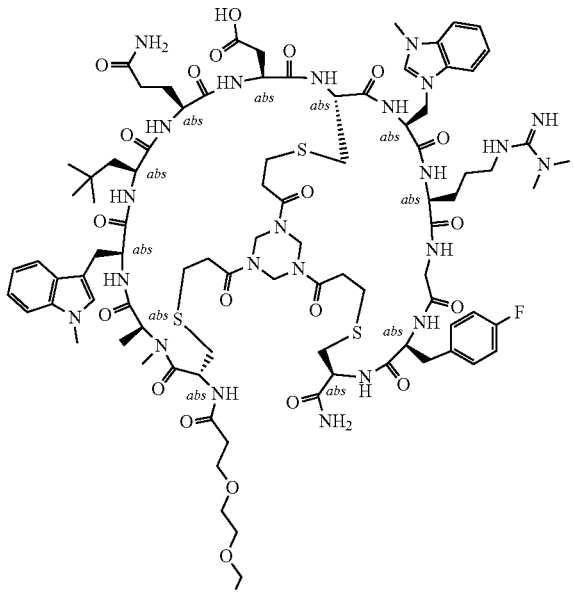

-continued
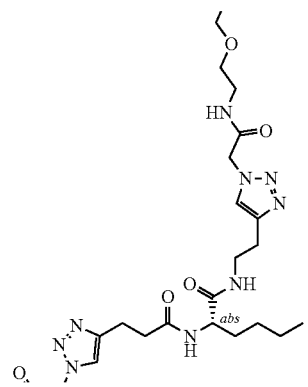
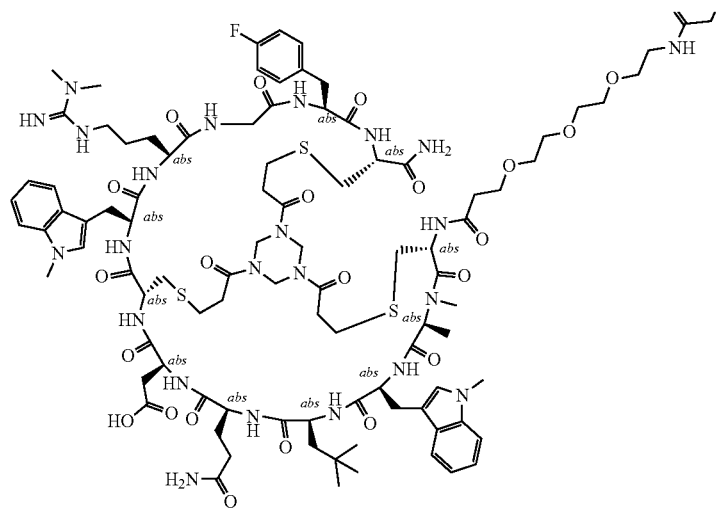
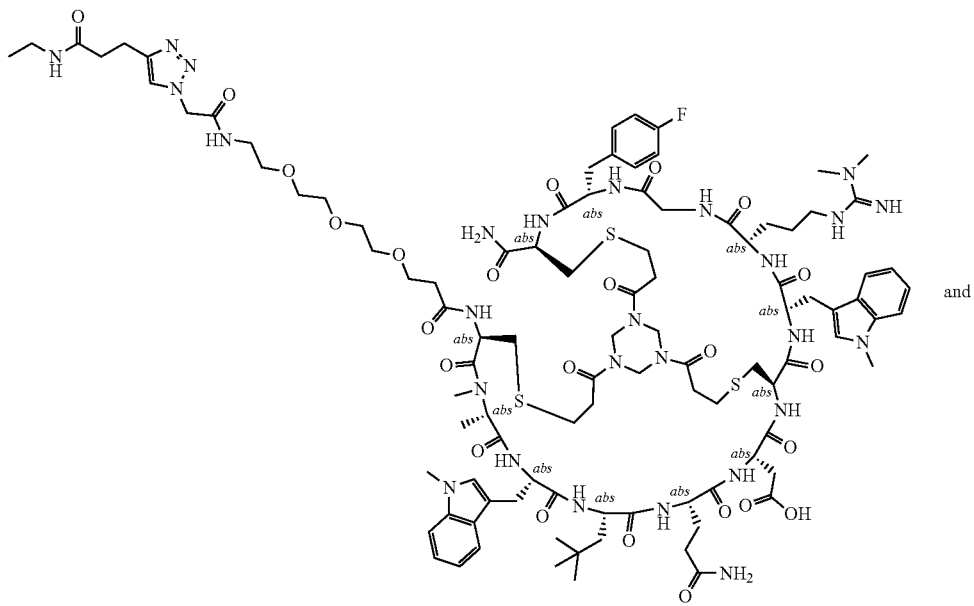
and

-continued

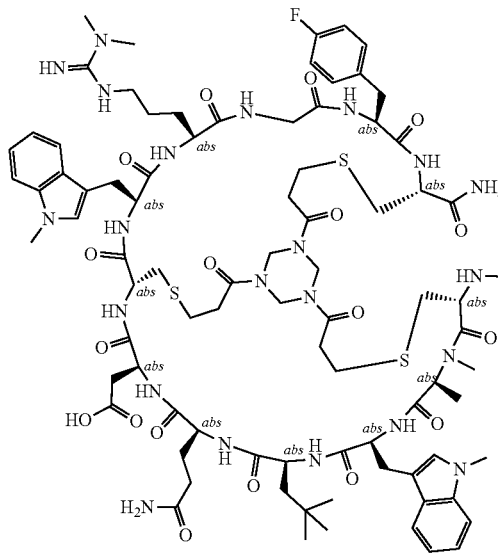

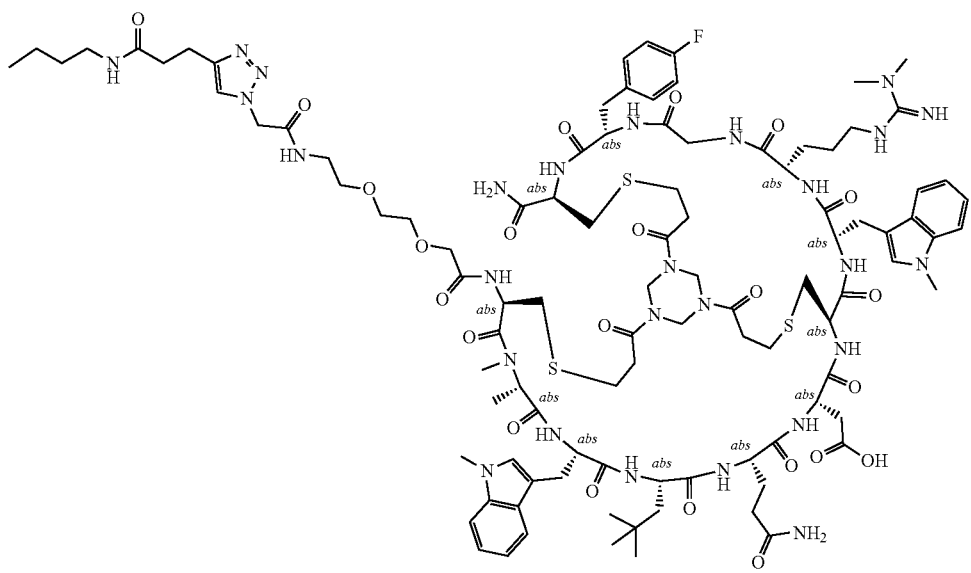

10. The peptide ligand as defined in claim 1, wherein the molecular scaffold is 1,1',1''-(1,3,5-triazinane-1,3,5-triyl)triprop-2-en-1-one (TATA).

11. The peptide ligand as defined in claim 1, wherein the peptide ligand is a free acid, or a pharmaceutically acceptable salt selected from sodium, potassium, calcium, and ammonium salt.

12. A pharmaceutical composition comprising the peptide ligand of claim 1, or a pharmaceutically acceptable salt thereof, in combination with one or more pharmaceutically acceptable excipients.

13. The peptide ligand as defined in claim 7, wherein the linker moiety comprises a —(CH$_2$)$_{2-10}$— linker.

14. The peptide ligand as defined in claim 13, wherein the linker moiety comprises a —(CH$_2$)$_{3-9}$— linker.

15. The peptide ligand as defined in claim 13, wherein the linker moiety comprises a double bond or a triazinyl ring.

16. The peptide ligand as defined in claim 15, wherein the triazinyl ring is a 1,2,3 triazinyl ring.

17. The peptide ligand as defined in claim 13, wherein the linker moiety is selected from:
—CH$_2$—CH$_2$—CH$_2$—CH=CH—CH$_2$—CH$_2$—CH$_2$—CH$_2$—;
—CH$_2$—CH$_2$—CH$_2$—CH=CH—CH$_2$—CH$_2$—,
—CH$_2$—CH$_2$—CH$_2$—CH=CH—CH$_2$—CH$_2$—CH$_2$—;
—CH$_2$—CH$_2$—CH$_2$—CH=CH—CH$_2$—;
—CH$_2$—CH=CH—; and

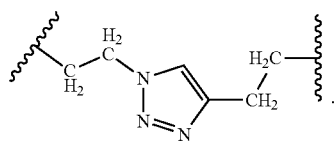 [SMILES: *CCc1cn(CC*)nn1]

18. The peptide ligand as defined in claim 7, wherein the molecular scaffold is 1,1',1''-(1,3,5-triazinane-1,3,5-triyl)triprop-2-en-1-one (TATA).

19. A multimeric binding complex comprising at least two peptide ligands, wherein each of said peptide ligands is as defined in claim 7, and wherein said peptide ligands may be the same or different.

* * * * *